US010876110B2

(12) United States Patent
Staehler et al.

(10) Patent No.: US 10,876,110 B2
(45) Date of Patent: *Dec. 29, 2020

(54) SYNTHESIS OF SEQUENCE-VERIFIED NUCLEIC ACIDS

(71) Applicant: CODEX DNA, INC., San Diego, CA (US)

(72) Inventors: Peer F. Staehler, Mannheim (DE); Raphael Carapito, Strasbourg (FR); Cord F. Staehler, Weinheim (DE); Mark Matzas, Heidelberg (DE); Jack T. Leonard, South Hamilton, MA (US); Joachim Jaeger, Bruchsal (DE); Markus Beier, Weinheim (DE)

(73) Assignee: Codex DNA, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/465,532

(22) Filed: Mar. 21, 2017

(65) Prior Publication Data

US 2017/0267999 A1 Sep. 21, 2017

Related U.S. Application Data

(63) Continuation of application No. 12/708,783, filed on Feb. 19, 2010, now abandoned.

(60) Provisional application No. 61/154,091, filed on Feb. 20, 2009.

(51) Int. Cl.
*C12Q 1/68* (2018.01)
*C12N 15/10* (2006.01)
*C12Q 1/6869* (2018.01)

(52) U.S. Cl.
CPC ....... *C12N 15/1093* (2013.01); *C12Q 1/6869* (2013.01)

(58) Field of Classification Search
CPC ............ C12Q 1/6869; C12Q 2563/149; C12Q 2565/501; C12Q 2565/518; C12N 15/1093
See application file for complete search history.

(56) References Cited

U.S. PATENT DOCUMENTS

| | | | | |
|---|---|---|---|---|
| 2007/0087349 | A1* | 4/2007 | Staehler | C12N 15/10 435/6.11 |
| 2008/0032301 | A1* | 2/2008 | Rank | B01J 19/0046 435/6.11 |
| 2010/0009872 | A1* | 1/2010 | Eid | G01N 33/54313 506/26 |

OTHER PUBLICATIONS

Droege et al. The genome sequencer FLX(TM) system-longer reads, more applications, straight forward bioinformatics and more complete data sets. J. Biotech., vol. 136 (1-2), p. 3-10, 2008.*
Calvet, J. P.: "*Molecular Approaches for Analyzing Differential Gene Expression: Differential Cdna Library Construction and Screening*"; Ediatric Nephrology, Springer Verlag, Berlin, DE LNKD-D01:10.1007/BF00857891, vol. 5, No. 6, Jan. 1, 1991, pp. 751-757.
Droege, M. et al.: "*The Genome Sequencer FLX(TM) System-Longer reads, more applications, straight forward bioinformatics and more complete data sets*" Journal of Biotechnology, Elsevier Science Publishers, Amsterdam, NL LNKD-D01:10.1016/J.JBIOTEC. 2008.03.021, vol. 136, No. 1-2, Aug. 31, 2008, pp. 3-10.
Bau, S. et al.: "*Targeted next-generation sequencing by specific capture of multiple genomic loci using low-volume microfluidic DNA arrays*"; Analytical and Bioanalytical Chemistry, Springer, DE LNKD D01:10.1007/ S00216-008-2460-7, vol. 393, No. 1, Jan. 1, 2009, pp. 171-175.
Margulies, Marcel et al.: "*Genome sequencing in microfabricated high-density picolitre reactors*" Nature, Nature Publishing Group, London, GB, vol. 437, No. 7057, Sep. 15, 2005, pp. 376-380.
Mitra et al.: "*In situ localized amplification and contact replication of many individual DNA molecules*"; Nucleic Acids Res. Dec. 15, 1999 27(24):e34).
Summerer, D. et al.: "*Targeted high throughput sequencing of a cancer-related exome subset by specific sequence capture with a fully automated microarray platform*" Genomics, Academic Press, San Diego, US, vol. 95, No. 4, Apr. 1, 2010, pp. 241-246.

* cited by examiner

*Primary Examiner* — David C Thomas
(74) *Attorney, Agent, or Firm* — DLA Piper LLP (US)

(57) ABSTRACT

The invention relates to methods and devices for preparing synthetic nucleic acids.

20 Claims, 32 Drawing Sheets

Specification includes a Sequence Listing.

| Bead number | x-position | y-position |
|---|---|---|
| 1 | 887 | 170 |
| 2 | 970 | 401 |
| 3 | 701 | 1039 |
| 4 | 917 | 1182 |
| 5 | 1293 | 75 |
| 6 | 2976 | 478 |
| 7 | 2852 | 689 |
| 8 | 3414 | 462 |
| 9 | 3243 | 545 |
| 10 | 3410 | 881 |
| 11 | 3662 | 523 |
| 12 | 3672 | 569 |
| 13 | 3668 | 609 |
| 14 | 3800 | 664 |
| 15 | 3915 | 921 |

```
Alignments
                               SEQ ID NO: 1
DNA_#1_from_x=887,y=170        CGCCATCAGACTTACTTCAATTATGAAGCCCAACAAGACAAATCAGGGCT
454_sequence_@_x=887,y=170     ----------ACTTACTTCAATTATGAAGCCCAACAAGACAAATCAGGGCT
                               SEQ ID NO: 2    **************************************

DNA_#1_from_x=887,y=170        GCCCAATGATCGGTTCTCTGCAGAGAGGCCTGAGGGATCCATCTCCACTC
454_sequence_@_x=887,y=170     GCCCAATGATCGGTTCTCTGCAGAGAGGCCTGAGGGATCCATCTCCACTC
                                               **************************************

DNA_#1_from_x=887,y=170        TGAAGATCCAGCCCTCAGAACCCAGGGACTCAGCTGTGTACTTCTGTGCC
454_sequence_@_x=887,y=170     TGAAGATCCAGCCCTCAGAACCCAGGGACTCAGCTGTGTACTTCTGTGCC
                                               **************************************

DNA_#1_from_x=887,y=170        AGCAGTCACCGGGACGGTCCCCAGCATTTTGGTGATGGGACTCGACTCTC
454_sequence_@_x=887,y=170     AGCAGTCACCGGGACGGTCCCCAGCATTTTGGTGATGGGACTCGACTCTC
                                               **************************************

DNA_#1_from_x=887,y=170        CATCCTAGAGGACCTGAACAAGGT
454_sequence_@_x=887,y=170     CATCCTAGAGGACCTGAACAAGGTGTTCCCACCCGAGGTCGCTGTGTTTG
                                               ************************

DNA_#1_from_x=887,y=170
454_sequence_@_x=887,y=170     AGCCA

------------------------------------------------------------------
                               SEQ ID NO: 3
DNA_#2_from_x=970,y=401        TCTGCCTCCCTCGCGCCATCAGGCAGATTTTACTCAAGGACGGTTTTCTG
454_sequence_@_x=970,y=401     ------------------------GCAGATTTTACTCAAGGACGGTTTTCTG
                               SEQ ID NO: 4    **************************

DNA_#2_from_x=970,y=401        TGAAACACATTCTGACCCAGAAAGCCCTTCACTTGGTGATCTCTCCAGTA
454_sequence_@_x=970,y=401     TGAAACACATTCTGACCCAGAAAGCCCTTCACTTGGTGATCTCTCCAGTA
                                               **************************************

DNA_#2_from_x=970,y=401        AGGACTGAAGACAGTGCCACTTACTACTGTGCCTTTTCCTGGAGGACGAT
454_sequence_@_x=970,y=401     AGGACTGAAGACAGTGCCACTTACTACTGTGCCTTTTCCTGGAGGACGAT
                                               **************************************

DNA_#2_from_x=970,y=401        AAACTCATCTTTGGAAAAGGAACCCGTGTGACTG----------
454_sequence_@_x=970,y=401     AAACTCATCTTTGGAAAAGGAACCCGTGTGACTGTGGAACCAAGAAGTCA
                                               **********************************

DNA_#2_from_x=970,y=401        ------------------
454_sequence_@_x=970,y=401     GCCTCATACCAAACCAT ------------------------------------------------------------------
                               SEQ ID NO: 5
DNA_#3_from_x=701,y=1039       TGCAGCCTCCCTTCCGCCATCAGGGAGCTCATGTTTGTCTACAACTTTAA
454_sequence_@_x=701,y=1039    -       ----          --------GGAGCTCATGTTTGTCTACAACTTTAA
                               SEQ ID NO: 6    **************************

DNA_#3_from_x=701,y=1039       AGAACAGACTGAAAACAACAGTGTGCCAAGTCGCTTCTCACCTGAATGCC
454_sequence_@_x=701,y=1039    AGAACAGACTGAAAACAACAGTGTGCCAAGTCGCTTCTCACCTGAATGCC
                                               **************************************

DNA_#3_from_x=701,y=1039       CCAACAGCTCTCACTTATTCCTTCACCTACACACCCTGCAGCCAGAAGAC
454_sequence_@_x=701,y=1039    CCAACAGCTCTCACTTATTCCTTCACCTACACACCCTGCAGCCAGAAGAC
                                               **************************************

DNA_#3_from_x=701,y=1039       TCGGCCCTGTATCTCTGTGCCAGCAGCCAAGATGGAGTAAATCAGCCTCA
454_sequence_@_x=701,y=1039    TCGGCCCTGTATCTCTGTGCCAGCAGCCAAGATGGAGTAAATCAGCCTCA
                                               **************************************

DNA_#3_from_x=701,y=1039       GCATTTTGGTGATGGGACTCGACTCTCCATCCTA----------------
454_sequence_@_x=701,y=1039    GCATTTTGGTGATGGGACTCGACTCTCCATCCTAGAGGACCTGAACAAGG
                                               **********************************

DNA_#3_from_x=701,y=1039       --------------
454_sequence_@_x=701,y=1039    TGTTCCCACCCGAGGTCG
```

Figure 2 (continued)

SEQ ID NO: 7

```
DNA_#4_from_x=917,y=1182      TATGCCTCCCTCGCGCCATCAGGGCTTTGAGGCTGAATTTAACAAGAGTC
454_sequence_@_x=917,y=1182   ------------------GGCTTTGAGGCTGAATTTAACAAGAGTC
                                   SEQ ID NO: 8       ******************************

DNA_#4_from_x=917,y=1182      AAACTTCCTTCCACTTGAGGAAACCCTCAGTCCATATAAGCGACACGGCT
454_sequence_@_x=917,y=1182   AAACTTCCTTCCACTTGAGGAAACCCTCAGTCCATATAAGCGACACGGCT
                              **************************************************

DNA_#4_from_x=917,y=1182      GAGTACTTCTGTGCTGTGAGTTACAGCACCCTCACCTTTGGGAAGGGGAC
454_sequence_@_x=917,y=1182   GAGTACTTCTGTGCTGTGAGTTACAGCACCCTCACCTTTGGGAAGGGGAC
                              **************************************************

DNA_#4_from_x=917,y=1182      TATGCTTCTAGTCTCTCCAGATATCCAGAACCC-----------------
454_sequence_@_x=917,y=1182   TATGCTTCTAGTCTCTCCAGATATCCAGAACCCTGACCCTGCCGTGTACC
                              *********************************

DNA_#4_from_x=917,y=1182      ----------
454_sequence_@_x=917,y=1182   AGCTGAGAGA
```

SEQ ID NO: 9

```
DNA_#5_from_x=1293,y=75       TCCCTCGCGCCATCAGGCTCTTCTGTCTACCATTGGTCTGGGTTAACCGC
454_sequence_@_x=1293,y=75    ------------------GCTCTTCTGTCTACCATTGGTCTGGGTTAACCGC
                                   SEQ ID NO: 10      ********************************

DNA_#5_from_x=1293,y=75       TGGTGCAGACGGTAAGAGAAATGCTGGTGTCAGGTTGGTGCTGTGGATGT
454_sequence_@_x=1293,y=75    TGGTGCAGACGGTAAGAGAAATGCTGGTGTCAGGTTGGTGCTGTGGATGT
                              **************************************************

DNA_#5_from_x=1293,y=75       TCAACAACGTCCCGAACATGCCTGAGAGGTTCACCAA-------------
454_sequence_@_x=1293,y=75    TCAACAACGTCCCGAACATGCCTGAGAGGTTCACCAAGTTCAACGCACGA
                              *************************************

DNA_#5_from_x=1293,y=75       -------------------------
454_sequence_@_x=1293,y=75    CAGTCAGACGAAGCACTCAAGCGAAGA
```

SEQ ID NO: 11

```
DNA_#6_from_x=2976,y=478      TCCCTCGCGCCATCAGGCCAGGTTCAGTGGCAGTGGATCTGGGACAGACT
454_sequence_@_x=2976,y=478   ------------------GCCAGGTTCAGTGGCAGTGGATCTGGGACAGACT
                                   SEQ ID NO: 12      ********************************

DNA_#6_from_x=2976,y=478      TCACTCTCACCATCAGCAGTCTGCAACCTGAAGATTTTGCTACTTACTAC
454_sequence_@_x=2976,y=478   TCACTCTCACCATCAGCAGTCTGCAACCTGAAGATTTTGCTACTTACTAC
                              **************************************************

DNA_#6_from_x=2976,y=478      TGTCAACAGAGTTACAGTGTC-CCCCGGG---------------------
454_sequence_@_x=2976,y=478   TGTCAACAGAGTTACAGTGTCCCCCCGGGCGTTCGGCCAAGGGACCAAGG
                              ********************* *******

DNA_#6_from_x=2976,y=478      ---------------------------------------
454_sequence_@_x=2976,y=478   TGGAAATCAAACGAACTGTGGCTGCACCATCTGTCTTCA
```

SEQ ID NO: 13

```
DNA_#7_from_x=2852,y=689      GCCTCCCTCGCGCCATCAGGCCAGGTTCAGTGGCAGTGGGTCTGGGACAG
454_sequence_@_x=2852,y=689   --------------------GCCAGGTTCAGTGGCAGTGGGTCTGGGACAG
                                   SEQ ID NO: 14       ******************************

DNA_#7_from_x=2852,y=689      AGTTCACTCTCACCATCAGCAGCCTGCAGTCTGAAGATTTTGCAGTTTAT
454_sequence_@_x=2852,y=689   AGTTCACTCTCACCATCAGCAGCCTGCAGTCTGAAGATTTTGCAGTTTAT
                              **************************************************

DNA_#7_from_x=2852,y=689      TACTGTCAGCAGTATAATAACTGGCCGTGGACGTTCGGCCAAGGGACCAA
454_sequence_@_x=2852,y=689   TACTGTCAGCAGTATAATAACTGGCCGTGGACGTTCGGCCAAGGGACCAA
                              **************************************************

DNA_#7_from_x=2852,y=689      GG-----------------------------------------
454_sequence_@_x=2852,y=689   GGTGGAAATCAAACGAACTGTGGCTGCACCATCTGTCTTCA
                              **
```

Figure 2 (continued)

SEQ ID NO: 15

```
DNA_#8_from_x=3414,y=462        TGCCTCCCTCGCGCCATCAGAACCACTTCTTTCCACTTGGAGAAAGGCTC
454_sequence_@_x=3414,y=462     ------------------AACCACTTCTTTCCACTTGGAGAAAGGCTC
                                         SEQ ID NO: 16 **************************

DNA_#8_from_x=3414,y=462        AGTTCAAGTGTCAGACTCAGCGGTGTACTTCTGTGCTCTGAGTGATATCG
454_sequence_@_x=3414,y=462     AGTTCAAGTGTCAGACTCAGCGGTGTACTTCTGTGCTCTGAGTGATATCG
                                **************************************************

DNA_#8_from_x=3414,y=462        ATGACATGCGCTTTGGAGCAGGGACCAGACTGACAGTAAAACCAAATATC
454_sequence_@_x=3414,y=462     ATGACATGCGCTTTGGAGCAGGGACCAGACTGACAGTAAAACCAAATATC
                                **************************************************

DNA_#8_from_x=3414,y=462        CAG-----------------------------
454_sequence_@_x=3414,y=462     CAGAACCCTGACCCTGCCGTGTACCAGCTGAGAGA
                                ***
```

SEQ ID NO: 17

```
DNA_#9_from_x=3243,y=545        TCCCTCGCGCCATCAGGAAGGGGCTGGAGTGGGTTGGCCGTATTAGAAAC
454_sequence_@_x=3243,y=545     ---------------GAAGGGGCTGGAGTGGGTTGGCCGTATTAGAAAC
                                         SEQ ID NO: 18 *****************************

DNA_#9_from_x=3243,y=545        AAAGCTAACAGTTACACCACAGAATATGCCGCGTCTGTGAAAGGCAGATT
454_sequence_@_x=3243,y=545     AAAGCTAACAGTTACACCACAGAATATGCCGCGTCTGTGAAAGGCAGATT
                                **************************************************

DNA_#9_from_x=3243,y=545        CACCATCTCAAGAGATGATTCAAAGAACTCACTGTATCTGCAAATGAACA
454_sequence_@_x=3243,y=545     CACCATCTCAAGAGATGATTCAAAGAACTCACTGTATCTGCAAATGAACA
                                **************************************************

DNA_#9_from_x=3243,y=545        GCCTGAAATCCGAGGACACGGCCGTGTATTACTGTGCTAGA---------
454_sequence_@_x=3243,y=545     GCCTGAAATCCGAGGACACGGCCGTGTATTACTGTGCTAGACCCTTAAGC
                                *****************************************

DNA_#9_from_x=3243,y=545        ---------------
454_sequence_@_x=3243,y=545     TACTTTGACTACT
```

SEQ ID NO: 19

```
DNA_#10_from_x=3410,y=881       TCCCTCCCGCCATCAGCAAGTGGAAGACTTAATGCCTCGCTGGATAAATC
454_sequence_@_x=3410,y=881     ----------------CAAGTGGAAGACTTAATGCCTCGCTGGATAAATC
                                         SEQ ID NO: 20 *********************************

DNA_#10_from_x=3410,y=881       ATCAGGACGTAGTACTTTATACATTGCAGCTTCTCAGCCTGGTGACTCAG
454_sequence_@_x=3410,y=881     ATCAGGACGTAGTACTTTATACATTGCAGCTTCTCAGCCTGGTGACTCAG
                                **************************************************

DNA_#10_from_x=3410,y=881       CCACCTACCTCTGTGCTCCCGAAGCGATGGGCGGATCTGAAAAGCTGGTC
454_sequence_@_x=3410,y=881     CCACCTACCTCTGTGCTCCCGAAGCGATGGGCGGATCTGAAAAGCTGGTC
                                **************************************************

DNA_#10_from_x=3410,y=881       TTTGGAAAGGGAACGAAACTGACAGTAAACCCATATA-------------
454_sequence_@_x=3410,y=881     TTTGGAAAGGGAACGAAACTGACAGTAAACCCATATATCCAGAACCCTGA
                                *************************************

DNA_#10_from_x=3410,y=881       -------------------------
454_sequence_@_x=3410,y=881     CCCTGCCGTGTACCAGCTGAGAGA
```

SEQ ID NO: 21

```
DNA_#11_from_x=3662,y=523       CCTCCCTCGCGCCATCAGACTCTCAAGATCCAGCCTGCAGAGCTTGGGGA
454_sequence_@_x=3662,y=523     ------------------ACTCTCAAGATCCAGCCTGCAGAGCTTGGGGA
                                         SEQ ID NO: 22 ********************************

DNA_#11_from_x=3662,y=523       CTCGGCCGTGTATCTCTGTGCCAGCAGCTTAGAAACAGGGGCTCCGGCTT
454_sequence_@_x=3662,y=523     CTCGGCCGTGTATCTCTGTGCCAGCAGCTTAGAAACAGGGGCTCCGGCTT
                                **************************************************

DNA_#11_from_x=3662,y=523       TCTTTGGACAAGGCACCAGACTCACAGTTGTAGAGGACC-----------
454_sequence_@_x=3662,y=523     TCTTTGGACAAGGCACCAGACTCACAGTTGTAGAGGACCTGAACAAGGTG
                                *************************************

DNA_#11_from_x=3662,y=523       ---------------------------------
454_sequence_@_x=3662,y=523     TTCCCACCCGAGGTCGCTGTGTTTCAGCCATCA
```

Figure 2 (continued)

```
                              SEQ ID NO: 23
DNA_#12_from_x=3672,y=569       CGCCATCAGAGGAGGGGAAGACCCCACAGCGTCTTCTGTACTATGACTCC
454_sequence_@_x=3672,y=569     ---------AGGAGGGGAAGACCCCACAGCGTCTTCTGTACTATGACTCC
                              SEQ ID NO: 24    *****************************************

DNA_#12_from_x=3672,y=569       TACAACTCCAAGGTTGTGTTGGAATCAGGAGTCAGTCCAGGGAAGCATTA
454_sequence_@_x=3672,y=569     TACAACTCCAAGGTTGTGTTGGAATCAGGAGTCAGTCCAGGGAAGCATTA
                                **************************************************

DNA_#12_from_x=3672,y=569       TACTTACGCAAGCACAAGGAACAACTTGAGATTGATACTGCGAAATCTAA
454_sequence_@_x=3672,y=569     TACTTACGCAAGCACAAGGAACAACTTGAGATTGATACTGCGAAATCTAA
                                **************************************************

DNA_#12_from_x=3672,y=569       GTGAAAATGACTCTGGGTCTATTACTGTGCCACCTGGGACGGGCAATAAG
454_sequence_@_x=3672,y=569     GTGAAAATGACTCTGGGTCTATTACTGTGCCACCTGGGACGGGCAATAAG
                                **************************************************

DNA_#12_from_x=3672,y=569       AAACTCTTTGGCAGTGGAACAACACTTGTTGTCACAGATAAACAACTTGA
454_sequence_@_x=3672,y=569     AAACTCTTTGGCAGTGGAACAACACTTGTTGTCACAGATAAACAACTTGA
                                **************************************************

DNA_#12_from_x=3672,y=569       TGCAGATGTTTCCCCCAGGCCCACTATTT
454_sequence_@_x=3672,y=569     TGCAGATGTTTCCCCCAGG----------
                                *******************

---------------------------------------------------------------
                              SEQ ID NO: 25
DNA_#13_from_x=3668,y=609       GCCATCAGTGAGGTGACTGATAAGGGAGATGTTCCTGAAGGGTACAAAGT
454_sequence_@_x=3668,y=609     ---------TGAGGTGACTGATAAGGGAGATGTTCCTGAAGGGTACAAAGT
                              SEQ ID NO: 26    *****************************************

DNA_#13_from_x=3668,y=609       CTCTCGAAAAGAGAAGAGGAATTTCCCC-CTGATCCTGGAGTCGCCCAGC
454_sequence_@_x=3668,y=609     CTCTCGAAAAGAGAAGAGGAATTTCCCCCCTGATCCTGGAGTCGCCCAGC
                                ****************************  ********************

DNA_#13_from_x=3668,y=609       CCCAACCAGACCTCTCTGTACTTCTGTGCCAGCAGTTTAAGGAGACAGGG
454_sequence_@_x=3668,y=609     CCCAACCAGACCTCTCTGTACTTCTGTGCCAGCAGTTTAAGGAGACAGGG
                                **************************************************

DNA_#13_from_x=3668,y=609       TGGTGAAAAACTGTTTTTTGGCAGTGGAACCCAGCTCTCTGTCTTGGAGG
454_sequence_@_x=3668,y=609     TGGTGAAAAACTGTTTTTTGGCAGTGGAACCCAGCTCTCTGTCTTGGAGG
                                **************************************************

DNA_#13_from_x=3668,y=609       ACC-----------------------------------------------
454_sequence_@_x=3668,y=609     ACCTGAACAAGGTGTTCCCACCCGAGGTCGCTGTGTTTGAGCCATCA
                                ***

---------------------------------------------------------------
                              SEQ ID NO: 27
DNA_#14_from_x=3800,y=664       CTCCCTCGCGCCATCAGGCCAGGTTCAGTGGCAGTGGATCTGGGACAGAA
454_sequence_@_x=3800,y=664     ---------------GCCAGGTTCAGTGGCAGTGGATCTGGGACAGAA
                                SEQ ID NO: 28    *****************************************

DNA_#14_from_x=3800,y=664       TTCACTCTCACAATCAGCAGCCTGCAGCCTGAAGATTTTGCAACTTATTA
454_sequence_@_x=3800,y=664     TTCACTCTCACAATCAGCAGCCTGCAGCCTGAAGATTTTGCAACTTATTA
                                **************************************************

DNA_#14_from_x=3800,y=664       CTGTCTACAGCATAATAGTTACCCTCGGGGGTTCGGCCAA-----------
454_sequence_@_x=3800,y=664     CTGTCTACAGCATAATAGTTACCCTCGGGGGTTCGGCCAAGGGACCAAGG
                                ****************************************

DNA_#14_from_x=3800,y=664       ---------------------------------------
454_sequence_@_x=3800,y=664     TGGAAATCAAACGAACTGTGGCTGCACCATCAGTCTTCA ---------------------------------------------------------------
                              SEQ ID NO: 29
DNA_#15_from_x=3915,y=921       CGCGCCATCAGTCGAGGTTCAGTGGCAGTGGGTCTGGGACAGACTTCACT
454_sequence_@_x=3915,y=921     ---------TCGAGGTTCAGTGGCAGTGGGTCTGGGACAGACTTCACT
                                SEQ ID NO: 30    *****************************************

DNA_#15_from_x=3915,y=921       CTCACCATCAGCAGACTGGAGCCTGAAGATTTTGCAGTTTATTACTGTCA
454_sequence_@_x=3915,y=921     CTCACCATCAGCAGACTGGAGCCTGAAGATTTTGCAGTTTATTACTGTCA
                                **************************************************

DNA_#15_from_x=3915,y=921       ACAGTATGGTTATTGGTACGCTTTTGGC----------------------
454_sequence_@_x=3915,y=921     ACAGTATGGTTATTGGTACGCTTTTGGCCAGGGGACCAAGCTGGAGATCA
                                ****************************

DNA_#15_from_x=3915,y=921       ---------------------------------------
454_sequence_@_x=3915,y=921     AACGAACTGTGGCTGCACCATCTGTCTTCA
```

Primer sequences

SEQ ID NO: 31
    GCCTCCCTCGCGCCATCAG        GS-FLX-A

SEQ ID NO: 32
    GCCTTGCCAGCCCGCTCAG        GS-FLX-B

Figure 5A

Construction oligos
β-D-Glucuronidase (UidA)
odd numbers: sense strand
even numbers: antisense strand

| | | |
|---|---|---|
| SEQ ID NO: 33 | CGACTGCACGGTGACCAATGCTTCTGGCGTCAGGCAGCCA | uidA_1 |
| SEQ ID NO: 34 | AGCCATACCACAGCTTCCGATGGCTGCCTGACGCCAGAAG | uidA_2 |
| SEQ ID NO: 35 | TCGGAAGCTGTGGTATGGCTGTGCAGGTCGTAAATCACTG | uidA_3 |
| SEQ ID NO: 36 | CTTGAGCGACACGAATTATGCAGTGATTTACGACCTGCAC | uidA_4 |
| SEQ ID NO: 37 | CATAATTCGTGTCGCTCAAGGCGCACTCCCGTTCTGGATA | uidA_5 |
| SEQ ID NO: 38 | GATGTCGGCGCAAAAAACATTATCCAGAACGGGAGTGCGC | uidA_6 |
| SEQ ID NO: 39 | ATGTTTTTTGCGCCGACATCATAACGGTTCTGGCAAATAT | uidA_7 |
| SEQ ID NO: 40 | TGTCAACAGCTCATTTCAGAATATTTGCCAGAACCGTTAT | uidA_8 |
| SEQ ID NO: 41 | TCTGAAATGAGCTGTTGACAATTAATCATCGGCTCGTATA | uidA_9 |
| SEQ ID NO: 42 | CCGCTCACAATTCCACACATTATACGAGCCGATGATTAAT | uidA_10 |
| SEQ ID NO: 43 | ATGTGTGGAATTGTGAGCGGATAACAATTTCACACAGGAA | uidA_11 |
| SEQ ID NO: 44 | GGCGGAGCATTGAATTCTGTTTCCTGTGTGAAATTGTTAT | uidA_12 |
| SEQ ID NO: 45 | ACAGAATTCAATGCTCCGCCCAGTCGAAACCCCAACCCGA | uidA_13 |
| SEQ ID NO: 46 | CCATCCAGTTTTTTAATCTCTCGGGTTGGGGTTTCGACTG | uidA_14 |
| SEQ ID NO: 47 | GAGATTAAAAAACTGGATGGCCTGTGGGCATTTAGCCTGG | uidA_15 |
| SEQ ID NO: 48 | AATGCCGCAGTTTTCGCGATCCAGGCTAAATGCCCACAGG | uidA_16 |
| SEQ ID NO: 49 | ATCGCGAAAACTGCGGCATTGATCAACGTTGGTGGGAATC | uidA_17 |
| SEQ ID NO: 50 | CTCGACTTTCCTGTAGCGCAGATTCCCACCAACGTTGATC | uidA_18 |
| SEQ ID NO: 51 | TGCGCTACAGGAAAGTCGAGCGATTGCAGTACCGGGGAGC | uidA_19 |
| SEQ ID NO: 52 | TCCGCAAACTGATCGTTAAAGCTCCCCGGTACTGCAATCG | uidA_20 |
| SEQ ID NO: 53 | TTTAACGATCAGTTTGCGGATGCCGATATTCGCAACTATG | uidA_21 |
| SEQ ID NO: 54 | CTGATACCAAACGTTCCCCGCATAGTTGCGAATATCGGCA | uidA_22 |
| SEQ ID NO: 55 | CGGGGAACGTTTGGTATCAGCGGGAAGTGTTTATACCGAA | uidA_23 |
| SEQ ID NO: 56 | TGCGCTGTCCAGCCCAGCCTTTCGGTATAAACACTTCCCG | uidA_24 |
| SEQ ID NO: 57 | AGGCTGGGCTGGACAGCGCATAGTCTTACGCTTTGATGCC | uidA_25 |
| SEQ ID NO: 58 | ACTTTGCCATAGTGGGTCACGGCATCAAAGCGTAAGACTA | uidA_26 |
| SEQ ID NO: 59 | GTGACCCACTATGGCAAAGTGTGGGTGAACAACCAGGAAG | uidA_27 |
| SEQ ID NO: 60 | GCCTCCCTGATGTTCCATCACTTCCTGGTTGTTCACCCAC | uidA_28 |
| SEQ ID NO: 61 | TGATGGAACATCAGGGAGGCTACACTCCCTTTGAAGCAGA | uidA_29 |
| SEQ ID NO: 62 | CAATCACATACGGGGTCACATCTGCTTCAAAGGGAGTGTA | uidA_30 |
| SEQ ID NO: 63 | TGTGACCCCGTATGTGATTGCGGGCAAATCAGTGAGGATT | uidA_31 |
| SEQ ID NO: 64 | TCGTTGTTGACGCACACGGTAATCCTCACTGATTTGCCCG | uidA_32 |

Figure 5A (continued)

| SEQ ID NO | Sequence | Name |
|---|---|---|
| SEQ ID NO: 65 | ACCGTGTGCGTCAACAACGAACTGAACTGGCAGACAATAC | uidA_33 |
| SEQ ID NO: 66 | CGTGATAACCATACCGGGCGGTATTGTCTGCCAGTTCAGT | uidA_34 |
| SEQ ID NO: 67 | CGCCCGGTATGGTTATCACGGACGAGAACGGCAAAAAGAA | uidA_35 |
| SEQ ID NO: 68 | AGTCGTGAAAGTACGACTGTTTCTTTTTGCCGTTCTCGTC | uidA_36 |
| SEQ ID NO: 69 | ACAGTCGTACTTTCACGACTTTTTTAACTATGCCGGCATT | uidA_37 |
| SEQ ID NO: 70 | TACAGCATAACCGAGCGGTGAATGCCGGCATAGTTAAAAA | uidA_38 |
| SEQ ID NO: 71 | CACCGCTCGGTTATGCTGTATACGACCCGAATACCTGGG | uidA_39 |
| SEQ ID NO: 72 | CACTACGGTGATATCATCGACCCAGGTATTCGGGGTCGTA | uidA_40 |
| SEQ ID NO: 73 | TCGATGATATCACCGTAGTGACACGTGGCGCAAGATTG | uidA_41 |
| SEQ ID NO: 74 | AATCCACACTCGCATGATTGCAATCTTGCGCCACGTGTGT | uidA_42 |
| SEQ ID NO: 75 | CAATCATGCGAGTGTGGATTGGCAAGTCGTGGCGAATGGC | uidA_43 |
| SEQ ID NO: 76 | CTTAGTTCTACGCTTACATCGCCATTCGCCACGACTTGCC | uidA_44 |
| SEQ ID NO: 77 | GATGTAAGCGTAGAACTAAGGGATGCGGATCAGCAAGTGG | uidA_45 |
| SEQ ID NO: 78 | GGTACCCTGGCCGGTTGCTACCACTTGCTGATCCGCATCC | uidA_46 |
| SEQ ID NO: 79 | TAGCAACCGGCCAGGGTACCAGCGGTACCTTGCAAGTGGT | uidA_47 |
| SEQ ID NO: 80 | GTTGCCACAGATGAGGATTCACCACTTGCAAGGTACCGCT | uidA_48 |
| SEQ ID NO: 81 | GAATCCTCATCTGTGGCAACCTGGAGAAGGCTATCTGTAT | uidA_49 |
| SEQ ID NO: 82 | TTGGCCGTAACGCACAGCTCATACAGATAGCCTTCTCCAG | uidA_50 |
| SEQ ID NO: 83 | GAGCTGTGCGTTACGGCCAAATCTCAGACGGAATGCGACA | uidA_51 |
| SEQ ID NO: 84 | GCCCACGCGAAGAGGATAGATGTCGCATTCCGTCTGAGAT | uidA_52 |
| SEQ ID NO: 85 | TCTATCCTCTTCGCGTGGGCATTAGATCAGTAGCCGTGAA | uidA_53 |
| SEQ ID NO: 86 | TAATCAGGAACTGTTCGCCTTTCACGGCTACTGATCTAAT | uidA_54 |
| SEQ ID NO: 87 | AGGCGAACAGTTCCTGATTAACCACAAGCCGTTCTACTTT | uidA_55 |
| SEQ ID NO: 88 | TCATGGCGACCAAAACCGGTAAAGTAGAACGGCTTGTGGT | uidA_56 |
| SEQ ID NO: 89 | ACCGGTTTTGGTCGCCATGAAGACGCTGATCTGCGCGGCA | uidA_57 |
| SEQ ID NO: 90 | CAGGACGTTGTCAAAGCCTTTGCCGCGCAGATCAGCGTCT | uidA_58 |
| SEQ ID NO: 91 | AAGGCTTTGACAACGTCCTGATGGTGCATGATCATGCGCT | uidA_59 |
| SEQ ID NO: 92 | TGGCCCCTATCCAATCCATGAGCGCATGATCATGCACCAT | uidA_60 |
| SEQ ID NO: 93 | CATGGATTGGATAGGGGCCAACAGCTATCGTACTTCCAC | uidA_61 |
| SEQ ID NO: 94 | ATCTCTTCGGCATACGGGTAGTGGGAAGTACGATAGCTGT | uidA_62 |
| SEQ ID NO: 95 | TACCCGTATGCCGAAGAGATGTTAGATTGGGCGGACGAAC | uidA_63 |
| SEQ ID NO: 96 | ATCGATCACGACTATGCCATGTTCGTCCGCCCAATCTAAC | uidA_64 |
| SEQ ID NO: 97 | ATGGCATAGTCGTGATCGATGAAACAGCTGCCGTGGGGTT | uidA_65 |
| SEQ ID NO: 98 | CAATGCCTAGTGAAAGGTTAAACCCCACGGCAGCTGTTTC | uidA_66 |
| SEQ ID NO: 99 | TAACCTTTCACTAGGCATTGGGTTCGAAGCCGGCAACAAA | uidA_67 |
| SEQ ID NO: 100 | TCACTGTACAGTTCTTTCGGTTTGTTGCCGGCTTCGAACC | uidA_68 |
| SEQ ID NO: 101 | CCGAAAGAACTGTACAGTGAGGAAGCAGTCAACGGAGAAA | uidA_69 |
| SEQ ID NO: 102 | CTGCAGATGTGCCTGTTGAGTTTCTCCGTTGACTGCTTCC | uidA_70 |
| SEQ ID NO: 103 | CTCAACAGGCACATCTGCAGGCGATAAAGGAACTGATTGC | uidA_71 |
| SEQ ID NO: 104 | ACGGATGGTTCTTATCGCGCGCAATCAGTTCCTTTATCGC | uidA_72 |
| SEQ ID NO: 105 | GCGCGATAAGAACCATCCGTCCTCGTGATGTGGAGCATA | uidA_73 |
| SEQ ID NO: 106 | CGCGTATCTGGTTCATTCGCTATGCTCCACATCACGACGG | uidA_74 |
| SEQ ID NO: 107 | GCGAATGAACCAGATACGCGTCCTCAAGGAGCTAGGGAAT | uidA_75 |
| SEQ ID NO: 108 | TTCCGCGAGCGGAGCAAAATATTCCCTAGCTCCTTGAGGA | uidA_76 |
| SEQ ID NO: 109 | ATTTTGCTCCGCTCGCGGAAGCTACCAGAAAACTAGATCC | uidA_77 |
| SEQ ID NO: 110 | CGCAAGTAATCGGGCGAGTGGATCTAGTTTTCTGGTAGC | uidA_78 |
| SEQ ID NO: 111 | CACTCGCCCGATTACTTGCGTCAACGTGATGTTTTGCGAT | uidA_79 |
| SEQ ID NO: 112 | CTAATGGTGTCGGTATGCGCATCGCAAAACATCACGTTGA | uidA_80 |
| SEQ ID NO: 113 | GCGCATACCGACACCATTAGCGACCTGTTTGATGTGCTGT | uidA_81 |
| SEQ ID NO: 114 | ACCGTAATAGCGGTTCAGGCACAGCACATCAAACAGGTCG | uidA_82 |
| SEQ ID NO: 115 | GCCTGAACCGCTATTACGGTTGGTATGTACAGTCAGGGA | uidA_83 |
| SEQ ID NO: 116 | CTTTCTCCGCAGTTTCCAGATCCCCTGACTGTACATACCA | uidA_84 |

Figure 5A (continued)

| SEQ ID NO: 117 | TCTGGAAACTGCGGAGAAAGTACTGGAGAAAGAGCTGCTA | uidA_85 |
| SEQ ID NO: 118 | TGGAGTTTCTCCTGCCAAGCTAGCAGCTCTTTCTCCAGTA | uidA_86 |
| SEQ ID NO: 119 | GCTTGGCAGGAGAAACTCCATCAGCCGATTATTATCACGG | uidA_87 |
| SEQ ID NO: 120 | TAGGGTGTCTACCCCATATTCCGTGATAATAATCGGCTGA | uidA_88 |
| SEQ ID NO: 121 | AATATGGGGTAGACACCCTAGCAGGTCTCCATAGCATGTA | uidA_89 |
| SEQ ID NO: 122 | CCTCAGACCACATGTCCGTGTACATGCTATGGAGACCTGC | uidA_90 |
| SEQ ID NO: 123 | CACGGACATGTGGTCTGAGGAATACCAGTGTGCCTGGCTG | uidA_91 |
| SEQ ID NO: 124 | AACACGCGATGATACATATCCAGCCAGGCACACTGGTATT | uidA_92 |
| SEQ ID NO: 125 | GATATGTATCATCGCGTGTTTGATAGGGTCTCAGCCGTGG | uidA_93 |
| SEQ ID NO: 126 | GTTCCAAACCTGCTCACCCACCACGGCTGAGACCCTATCA | uidA_94 |
| SEQ ID NO: 127 | TGGGTGAGCAGGTTTGGAACTTTGCGGACTTTGCAACGTC | uidA_95 |
| SEQ ID NO: 128 | CCACACGCAAAATCCCTTGAGACGTTGCAAAGTCCGCAAA | uidA_96 |
| SEQ ID NO: 129 | TCAAGGGATTTTGCGTGTGGGCGGGAACAAGAAAGGCATT | uidA_97 |
| SEQ ID NO: 130 | GGCTTGCGATCTCTGGTGAAAATGCCTTTCTTGTTCCCGC | uidA_98 |
| SEQ ID NO: 131 | TTCACCAGAGATCGCAAGCCGAAAAGCGCCGCTTTTCTAT | uidA_99 |
| SEQ ID NO: 132 | CCCCGTCCAGCGCTTCTGCAATAGAAAGCGGCGCTTTTC | uidA_100 |
| SEQ ID NO: 133 | TGCAGAAGCGCTGGACGGGGATGAATTTTGGCGAAAAACC | uidA_101 |
| SEQ ID NO: 134 | GTTGTTTACCGCCCTGCTGGGGTTTTTCGCCAAAATTCAT | uidA_102 |
| SEQ ID NO: 135 | CCAGCAGGGCGGTAAACAACATCACCATCACCATCACTAA | uidA_103 |
| SEQ ID NO: 136 | TTAGTGATGGTGATGGTGAT | uidA_104 |

Figure 5B

***Biomphalaria glabrata* hemoglobin (BgHb)**
odd numbers: sense strand
even numbers: antisense strand

| | | |
|---|---|---|
| SEQ ID NO: 137 | GGGGACAAGTTTGTACAAAAAAGCAGGCTTCGAAGGAGAT | BgHb_1 |
| SEQ ID NO: 138 | AGGACGAACATCATGGTTCTATCTCCTTCGAAGCCTGCTT | BgHb_2 |
| SEQ ID NO: 139 | AGAACCATGATGTTCGTCCTTAAGGGATCCGTCGTCCAAG | BgHb_3 |
| SEQ ID NO: 140 | GATGCTCAACAGGACGAATGCTTGGACGACGGATCCCTTA | BgHb_4 |
| SEQ ID NO: 141 | CATTCGTCCTGTTGAGCATCGTCTGCCTCGAAATCACCAT | BgHb_5 |
| SEQ ID NO: 142 | ACCTGACACCGTCGTCTGCTATGGTGATTTCGAGGCAGAC | BgHb_6 |
| SEQ ID NO: 143 | AGCAGACGACGGTGTCAGGTATGTGAACGCTGAGTGGAAG | BgHb_7 |
| SEQ ID NO: 144 | TCTTGGGATTGTTCTGGACGCTTCCACTCAGCGTTCACAT | BgHb_8 |
| SEQ ID NO: 145 | CGTCCAGAACAATCCCAAGAAGGTAGGCACTCTAGAACGG | BgHb_9 |
| SEQ ID NO: 146 | GTTGTCCTCTAACCTCCTAGCCGTTCTAGAGTGCCTACCT | BgHb_10 |
| SEQ ID NO: 147 | CTAGGAGGTTAGAGGACAACTCTGAGGAAGTCGCATGCTC | BgHb_11 |
| SEQ ID NO: 148 | GTCGGAACTTCACTTCCGTAGAGCATGCGACTTCCTCAGA | BgHb_12 |
| SEQ ID NO: 149 | TACGGAAGTGAAGTTCCGACAGAGAGCTCCTGCCGAGTAC | BgHb_13 |
| SEQ ID NO: 150 | GCCTTCTTGATCTTGTTAGCGTACTCGGCAGGAGCTCTCT | BgHb_14 |
| SEQ ID NO: 151 | GCTAACAAGATCAAGAAGGCAAAGGACAAGCTGCGGAGAC | BgHb_15 |
| SEQ ID NO: 152 | ATCGTCGAACTGAGATTCCAGTCTCCGCAGCTTGTCCTTT | BgHb_16 |
| SEQ ID NO: 153 | TGGAATCTCAGTTCGACGATTGCCAGCAGGAAAACGACAG | BgHb_17 |
| SEQ ID NO: 154 | GTTGGATCAGCCTGTCCTTCCTGTCGTTTTCCTGCTGGCA | BgHb_18 |
| SEQ ID NO: 155 | GAAGGACAGGCTGATCCAACTCCAAGCAAACCTCACCGAT | BgHb_19 |
| SEQ ID NO: 156 | GTTACGAGCCTGTGGATGGTATCGGTGAGGTTTGCTTGGA | BgHb_20 |
| SEQ ID NO: 157 | ACCATCCACAGGCTCGTAACCGACTCTGACATTCAGGCAC | BgHb_21 |
| SEQ ID NO: 158 | AGTAGCCCAGGATGACCTAAGTGCCTGAATGTCAGAGTCG | BgHb_22 |
| SEQ ID NO: 159 | TTAGGTCATCCTGGGCTACTTTGACCGCTGGTGCTGATGG | BgHb_23 |
| SEQ ID NO: 160 | TGTTACCGAAGTTGTTCCGTCCATCAGCACCAGCGGTCAA | BgHb_24 |
| SEQ ID NO: 161 | ACGGAACAACTTCGGTAACAACTTCGTGCTGTGGCTACTG | BgHb_25 |
| SEQ ID NO: 162 | CTTATGTTCGGGATCGTGTTCAGTAGCCACAGCACGAAGT | BgHb_26 |

Figure 5B (continued)

| | | |
|---|---|---|
| SEQ ID NO: 163 | AACACGATCCCGAACATAAGGGAGCGTTTCGAGAAGTTCA | BgHb_27 |
| SEQ ID NO: 164 | TTCATCGCTCTGGTGAGCGTTGAACTTCTCGAAACGCTCC | BgHb_28 |
| SEQ ID NO: 165 | ACGCTCACCAGAGCGATGAAGCCCTCAAGAACGACAACGA | BgHb_29 |
| SEQ ID NO: 166 | GCTTCACCTGCTTCACGAATTCGTTGTCGTTCTTGAGGGC | BgHb_30 |
| SEQ ID NO: 167 | ATTCGTGAAGCAGGTGAAGCTGATCGTTGGTGGACTGCAG | BgHb_31 |
| SEQ ID NO: 168 | TCGAGGTTGTCGATGAAGCTCTGCAGTCCACCAACGATCA | BgHb_32 |
| SEQ ID NO: 169 | AGCTTCATCGACAACCTCGAAACCCTGGTCAGCTGCAAG | BgHb_33 |
| SEQ ID NO: 170 | AGCCAACCTTTCGATCGTAGCTTGCAGCTGACCAGGGTTT | BgHb_34 |
| SEQ ID NO: 171 | CTACGATCGAAAGGTTGGCTTCCGTACACCTCAAGATGAG | BgHb_35 |
| SEQ ID NO: 172 | ATTCCAGACCAATGGTAGGCCTCATCTTGAGGTGTACGGA | BgHb_36 |
| SEQ ID NO: 173 | GCCTACCATTGGTCTGGAATACTTCAGGCCTCTGCAAGAG | BgHb_37 |
| SEQ ID NO: 174 | GCAACGTACTGTGCAATGTTCTCTTGCAGAGGCCTGAAGT | BgHb_38 |
| SEQ ID NO: 175 | AACATTGCACAGTACGTTGCTAGCGCTCTGGGTGTGGGTG | BgHb_39 |
| SEQ ID NO: 176 | TTTAGGAGCTGCGTCATCTGCACCCACACCCAGAGCGCTA | BgHb_40 |
| SEQ ID NO: 177 | CAGATGACGCAGCTCCTAAAGCTTGGGAACGTCTCCTGAA | BgHb_41 |
| SEQ ID NO: 178 | TGAGGACCTCGTTGAAAGCGTTCAGGAGACGTTCCCAAGC | BgHb_42 |
| SEQ ID NO: 179 | CGCTTTCAACGAGGTCCTCAACAGCTTCGCCAACTACAAC | BgHb_43 |
| SEQ ID NO: 180 | TCCGTATCGCTCAGTCCGATGTTGTAGTTGGCGAAGCTGT | BgHb_44 |
| SEQ ID NO: 181 | ATCGGACTGAGCGATACGGACAAAGTAGCCCTTCAGAGCA | BgHb_45 |
| SEQ ID NO: 182 | AGCGGTTAACCTAGACCAACTGCTCTGAAGGGCTACTTTG | BgHb_46 |
| SEQ ID NO: 183 | GTTGGTCTAGGTTAACCGCTGGTGCAGACGGTAAGAGAAA | BgHb_47 |
| SEQ ID NO: 184 | GCACCAACCTGACACCAGCATTTCTCTTACCGTCTGCACC | BgHb_48 |
| SEQ ID NO: 185 | TGCTGGTGTCAGGTTGGTGCTGTGGATGTTCAACAACGTC | BgHb_49 |
| SEQ ID NO: 186 | AACCTCTCACGCATGTTCGGGACGTTGTTGAACATCCACA | BgHb_50 |
| SEQ ID NO: 187 | CCGAACATGCGTGAGAGGTTCACCAAGTTCAACGCACGAC | BgHb_51 |
| SEQ ID NO: 188 | CTTGAGTGCTTCGTCTGACTGTCGTGCGTTGAACTTGGTG | BgHb_52 |
| SEQ ID NO: 189 | AGTCAGACGAAGCACTCAAGACCGACGCAGAATTCCTGAA | BgHb_53 |
| SEQ ID NO: 190 | CGATGATTGCGTCTACCTGCTTCAGGAATTCTGCGTCGGT | BgHb_54 |
| SEQ ID NO: 191 | GCAGGTAGACGCAATCATCGGTGGTTTCGAGACCCTGATC | BgHb_55 |
| SEQ ID NO: 192 | TCTGCGTCGTTGAGGTTGTTGATCAGGGTCTCGAAACCAC | BgHb_56 |
| SEQ ID NO: 193 | AACAACCTCAACGACGCAGACCTCTTGCTGAACAGACTAG | BgHb_57 |
| SEQ ID NO: 194 | GTGTTCGTCAGCCAGACTCTCTAGTCTGTTCAGCAAGAGG | BgHb_58 |
| SEQ ID NO: 195 | AGAGTCTGGCTGACGAACACCTCGAAAAGAAGCCAGCGAT | BgHb_59 |
| SEQ ID NO: 196 | GACCGAAGTAGTTGCTGGAGATCGCTGGCTTCTTTTCGAG | BgHb_60 |
| SEQ ID NO: 197 | CTCCAGCAACTACTTCGGTCCTCTCCAGAAGAACATCCAC | BgHb_61 |
| SEQ ID NO: 198 | AGGGTACCCTCGATGAAGAGGTGGATGTTCTTCTGGAGAG | BgHb_62 |
| SEQ ID NO: 199 | CTCTTCATCGAGGGTACCCTCAACTTTGGGAGTGACTCAG | BgHb_63 |
| SEQ ID NO: 200 | AGTCCAAGCTCTAGCTTCGTCTGAGTCACTCCCAAAGTTG | BgHb_64 |
| SEQ ID NO: 201 | ACGAAGCTAGAGCTTGGACTCACTTGGTCGGAGCGTTGAA | BgHb_65 |
| SEQ ID NO: 202 | CGTGGTCCTTGATGACCTTGTTCAACGCTCCGACCAAGTG | BgHb_66 |
| SEQ ID NO: 203 | CAAGGTCATCAAGGACCACGCTATCCACAACCTGGGTTTG | BgHb_67 |
| SEQ ID NO: 204 | GCGTCTCTGTCTATGTCGGACAAACCCAGGTTGTGGATAG | BgHb_68 |
| SEQ ID NO: 205 | TCCGACATAGACAGAGACGCTCTGGTCTCGTCATGGAATC | BgHb_69 |
| SEQ ID NO: 206 | TCCTGCCCTACCGGTCAATTGATTCCATGACGAGACCAGA | BgHb_70 |
| SEQ ID NO: 207 | AATTGACCGGTAGGGCAGGAGGTAGTCGAAACGCAGGTAC | BgHb_71 |
| SEQ ID NO: 208 | GCATCCACAGCACGAGGTTAGTACCTGCGTTTCGACTACC | BgHb_72 |
| SEQ ID NO: 209 | TAACCTCGTGCTGTGGATGCTCGAAACGTGCCTAACATG | BgHb_73 |
| SEQ ID NO: 210 | AACTTCGAGAACTGGTCACGCATGTTAGGCACGTTTTCGA | BgHb_74 |
| SEQ ID NO: 211 | CGTGACCAGTTCTCGAAGTTAACGCTAGGCAGTCCGACG | BgHb_75 |
| SEQ ID NO: 212 | AGCGTCCTTTCTCAGGTTATCGTCGGACTGCCTAGCGTTG | BgHb_76 |
| SEQ ID NO: 213 | ATAACCTGAGAAAGGACGCTGAGTTCGTGCGACAAGTTGA | BgHb_77 |
| SEQ ID NO: 214 | CCAGACCTCCCGTAATCAGGTCAACTTGTCGCACGAACTC | BgHb_78 |

Figure 5B (continued)

| SEQ ID NO: 215 | CCTGATTACGGGAGGTCTGGAATCACTCGTCGACAACGTG | BgHb_79 |
| SEQ ID NO: 216 | TGCAGGAAGATTGGGTTGTTCACGTTGTCGACGAGTGATT | BgHb_80 |
| SEQ ID NO: 217 | AACAACCCAATCTTCCTGCAGGAAGCTCTGGTTAGACTCG | BgHb_81 |
| SEQ ID NO: 218 | CAGGTTAAGGTGAGCATCTGCGAGTCTAACCAGAGCTTCC | BgHb_82 |
| SEQ ID NO: 219 | CAGATGCTCACCTTAACCTGAAGCCTAGGGTGGGTCTTGA | BgHb_83 |
| SEQ ID NO: 220 | TCTGCAGTGGACCAAAGTACTCAAGACCCACCCTAGGCTT | BgHb_84 |
| SEQ ID NO: 221 | GTACTTTGGTCCACTGCAGAGGTACATACACGCCTACATC | BgHb_85 |
| SEQ ID NO: 222 | GATACTCCGAGTGCCTTTTCGATGTAGGCGTGTATGTACC | BgHb_86 |
| SEQ ID NO: 223 | GAAAAGGCACTCGGAGTATCGGCAGATTCCGCAGCTCCAA | BgHb_87 |
| SEQ ID NO: 224 | AAGCAAGTCGGTCCATGCTCTTGGAGCTGCGGAATCTGCC | BgHb_88 |
| SEQ ID NO: 225 | GAGCATGGACCGACTTGCTTACCGCTTTCAACAACGTCCT | BgHb_89 |
| SEQ ID NO: 226 | GATGGTGATGCCTGTCCTTCAGGACGTTGTTGAAAGCGGT | BgHb_90 |
| SEQ ID NO: 227 | GAAGGACAGGCATCACCATCACCATCACTAGGACCCAGCT | BgHb_91 |
| SEQ ID NO: 228 | GGGGACCACTTTGTACAAGAAAGCTGGGTCCTAGTGATGGT | BgHb_92 |

Figure 6A

Gene sequences
β-D-Glucuronidase (UidA)
SEQ ID NO: 229

CGACTGCACGGTGACCAATGCTTCTGGCGTCAGGCAGCCATCGGAAGCTGTGGTA
TGGCTGTGCAGGTCGTAAATCACTGCATAATTCGTGTCGCTCAAGGCGCACTCCC
GTTCTGGATAATGTTTTTTGCGCCGACATCATAACGGTTCTGGCAAATATTCTGA
AATGAGCTGTTGACAATTAATCATCGGCTCGTATAATGTGTGGAATTGTGAGCGG
ATAACAATTTCACACAGGAAACAGAATTCAATGCTCCGCCCAGTCGAAACCCCAA
CCCGAGAGATTAAAAAACTGGATGGCCTGTGGGCATTTAGCCTGGATCGCGAAAA
CTGCGGCATTGATCAACGTTGGTGGGAATCTGCGCTACAGGAAGTCGAGCGATT
GCAGTACCGGGGAGCTTTAACGATCAGTTTGCGGATGCCGATATTCGCAACTATG
CGGGGAACGTTTGGTATCAGCGGGAAGTGTTTATACCGAAAGGCTGGGCTGGACA
GCGCATAGTCTTACGCTTTGATGCCGTGACCCACTATGGCAAAGTGTGGGTGAAC
AACCAGGAAGTGATGGAACATCAGGGAGGCTACACTCCCTTTGAAGCAGATGTGA
CCCCGTATGTGATTGCGGGCAAATCAGTGAGGATTACCGTGTGCGTCAACAACGA
ACTGAACTGGCAGACAATACCGCCCGGTATGGTTATCACGGACGAGAACGGCAAA
AAGAAACAGTCGTACTTTCACGACTTTTTTAACTATGCCGGCATTCACCGCTCGG
TTATGCTGTATACGACCCCGAATACCTGGGTCGATGATATCACCGTAGTGACACA
CGTGGCGCAAGATTGCAATCATGCGAGTGTGGATTGGCAAGTCGTGGCGAATGGC
GATGTAAGCGTAGAACTAAGGGATGCGGATCAGCAAGTGGTAGCAACCGGCCAGG
GTACCAGCGGTACCTTGCAAGTGGTGAATCCTCATCTGTGGCAACCTGGAGAAGG
CTATCTGTATGAGCTGTGCGTTACGGCCAAATCTCAGACGGAATGCGACATCTAT
CCTCTTCGCGTGGGCATTAGATCAGTAGCCGTGAAAGGCGAACAGTTCCTGATTA
ACCACAAGCCGTTCTACTTTACCGGTTTTGGTCGCCATGAAGACGCTGATCTGCG
CGGCAAAGGCTTTGACAACGTCCTGATGGTGCATGATCATGCGCTCATGGATTGG
ATAGGGGCCAACAGCTATCGTACTTCCCACTACCCGTATGCCGAAGAGATGTTAG
ATTGGGCGGACGAACATGGCATAGTCGTGATCGATGAAACAGCTGCCGTGGGGTT
TAACCTTTCACTAGGCATTGGGTTCGAAGCCGGCAACAAACCGAAAGAACTGTAC
AGTGAGGAAGCAGTCAACGGAGAAACTCAACAGGCACATCTGCAGGCGATAAAGG
AACTGATTGCGCGCGATAAGAACCATCCGTCCGTCGTGATGTGGAGCATAGCGAA
TGAACCAGATACGCGTCCTCAAGGAGCTAGGGAATATTTTGCTCCGCTCGCGGAA
GCTACCAGAAAACTAGATCCCACTCGCCCGATTACTTGCGTCAACGTGATGTTTT
GCGATGCGCATACCGACACCATTAGCGACCTGTTTGATGTGCTGTGCCTGAACCG
CTATTACGGTTGGTATGTACAGTCAGGGATCTGGAAACTGCGGAGAAAGTACTG
GAGAAAGAGCTGCTAGCTTGGCAGGAGAAACTCCATCAGCCGATTATTATCACGG
AATATGGGGTAGACACCCTAGCAGGTCTCCATAGCATGTACACGGACATGTGGTC
TGAGGAATACCAGTGTGCCTGGCTGGATATGTATCATCGCGTGTTTGATAGGGTC
TCAGCCGTGGTGGGTGAGCAGGTTTGGAACTTTGCGGACTTTGCAACGTCTCAAG
GGATTTTGCGTGTGGGCGGGAACAAGAAAGGCATTTTCACCAGAGATCGCAAGCC
GAAAAGCGCCGCTTTTCTATTGCAGAAGCGCTGGACGGGGATGAATTTTGGCGAA
AAACCCCAGCAGGGCGGTAAACAACATCACCATCACCATCACTAA

Figure 6B

*Biomphalaria glabrata* hemoglobin (BgHb)

SEQ ID NO: 230

```
GGGGACAAGTTTGTACAAAAAAGCAGGCTTCGAAGGAGATAGAACCATGATGTTCGTCCTTAAGGG
ATCCGTCGTCCAAGCATTCGTCCTGTTGAGCATCGTCTGCCTCGAAATCACCATAGCAGACGACGG
TGTCAGGTATGTGAACGCTGAGTGGAAGCGTCCAGAACAATCCCAAGAAGGTAGGCACTCTAGAAC
GGCTAGGAGGTTAGAGGACAACTCTGAGGAAGTCGCATGCTCTACGGAAGTGAAGTTCCGACAGAG
AGCTCCTGCCGAGTACGCTAACAAGATCAAGAAGGCAAAGGACAAGCTGCGGAGACTGGAATCTCA
GTTCGACGATTGCCAGCAGGAAAACGACAGGAAGGACAGGCTGATCCAACTCCAAGCAAACCTCAC
CGATACCATCCACAGGCTCGTAACCGACTCTGACATTCAGGCACTTAGGTCATCCTGGGCTACTTT
GACCGCTGGTGCTGATGGACGGAACAACTTCGGTAACAACTTCGTGCTGTGGCTACTGAACACGAT
CCCGAACATAAGGGAGCGTTTCGAGAAGTTCAACGCTCACCAGAGCGATGAAGCCCTCAAGAACGA
CAACGAATTCGTGAAGCAGGTGAAGCTGATCGTTGGTGGACTGCAGAGCTTCATCGACAACCTCGA
AAACCCTGGTCAGCTGCAAGCTACGATCGAAAGGTTGGCTTCCGTACACCTCAAGATGAGGCCTAC
CATTGGTCTGGAATACTTCAGGCCTCTGCAAGAGAACATTGCACAGTACGTTGCTAGCGCTCTGGG
TGTGGGTGCAGATGACGCAGCTCCTAAAGCTTGGGAACGTCTCCTGAACGCTTTCAACGAGGTCCT
CAACAGCTTCGCCAACTACAACATCGGACTGAGCGATACGGACAAAGTAGCCCTTCAGAGCAGTTG
GTCTAGGTTAACCGCTGGTGCAGACGGTAAGAGAAATGCTGGTGTCAGGTTGGTGCTGTGGATGTT
CAACAACGTCCCGAACATGCGTGAGAGGTTCACCAAGTTCAACGCACGACAGTCAGACGAAGCACT
CAAGACCGACGCAGAATTCCTGAAGCAGGTAGACGCAATCATCGGTGGTTTCGAGACCCTGATCAA
CAACCTCAACGACGCAGACCTCTTGCTGAACAGACTAGAGAGTCTGGCTGACGAACACCTCGAAAA
GAAGCCAGCGATCTCCAGCAACTACTTCGGTCCTCTCCAGAAGAACATCCACCTCTTCATCGAGGG
TACCCTCAACTTTGGGAGTGACTCAGACGAAGCTAGAGCTTGGACTCACTTGGTCGGAGCGTTGAA
CAAGGTCATCAAGGACCACGCTATCCACAACCTGGGTTTGTCCGACATAGACAGAGACGCTCTGGT
CTCGTCATGGAATCAATTGACCGGTAGGGCAGGAGGTAGTCGAAACGCAGGTACTAACCTCGTGCT
GTGGATGCTCGAAAACGTGCCTAACATGCGTGACCAGTTCTCGAAGTTCAACGCTAGGCAGTCCGA
CGATAACCTGAGAAAGGACGCTGAGTTCGTGCGACAAGTTGACCTGATTACGGGAGGTCTGGAATC
ACTCGTCGACAACGTGAACAACCCAATCTTCCTGCAGGAAGCTCTGGTTAGACTCGCAGATGCTCA
CCTTAACCTGAAGCCTAGGGTGGGTCTTGAGTACTTTGGTCCACTGCAGAGGTACATACACGCCTA
CATCGAAAAGGCACTCGGAGTATCGGCAGATTCCGCAGCTCCAAGAGCATGGACCGACTTGCTTAC
CGCTTTCAACAACGTCCTGAAGGACAGGCATCACCATCACCATCACTAGGACCCAGCTTTCTTGTA
CAAAGTGGTCCCC
```

Figure 7

Gene fragments (including sequencing primer)

>BgHb_A 394 bp
SEQ ID NO: 231
GCCTCCCTCGCGCCATCAGGCTCTTCTGGGGACAAGTTTGTACAAAAAAGCAGGC
TTCGAAGGAGATAGAACCATGATGTTCGTCCTTAAGGGATCCGTCGTCCAAGCAT
TCGTCCTGTTGAGCATCGTCTGCCTCGAAATCACCATAGCAGACGACGGTGTCAG
GTATGTGAACGCTGAGTGGAAGCGTCCAGAACAATCCCAAGAAGGTAGGCACTCT
AGAACGGCTAGGAGGTTAGAGGACAACTCTGAGGAAGTCGCATGCTCTACGGAAG
TGAAGTTCCGACAGAGAGCTCCTGCCGAGTACGCTAACAAGATCAAGAAGGCAAA
GGACAAGCTGCGGAGACTGGAATCTCAGTTCGACGATCGAAGAGCCTGAGCGGGC
TGGCAAGGC

>BgHb_B 394 bp
SEQ ID NO: 232
GCCTCCCTCGCGCCATCAGGCTCTTCTTACGGAAGTGAAGTTCCGACAGAGAGCT
CCTGCCGAGTACGCTAACAAGATCAAGAAGGCAAAGGACAAGCTGCGGAGACTGG
AATCTCAGTTCGACGATTGCCAGCAGGAAAACGACAGGAAGGACAGGCTGATCCA
ACTCCAAGCAAACCTCACCGATACCATCCACAGGCTCGTAACCGACTCTGACATT
CAGGCACTTAGGTCATCCTGGGCTACTTTGACCGCTGGTGCTGATGGACGGAACA
ACTTCGGTAACAACTTCGTGCTGTGGCTACTGAACACGATCCCGAACATAAGGGA
GCGTTTCGAGAAGTTCAACGCTCACCAGAGCGATGAACGAAGAGCCTGAGCGGGC
TGGCAAGGC

>BgHb_C 394 bp
SEQ ID NO: 233
 GCCTCCCTCGCGCCATCAGGCTCTTCTACGGAACAACTTCGGTAACAACTTCGTG
CTGTGGCTACTGAACACGATCCCGAACATAAGGGAGCGTTTCGAGAAGTTCAACG
CTCACCAGAGCGATGAAGCCCTCAAGAACGACAACGAATTCGTGAAGCAGGTGAA
GCTGATCGTTGGTGGACTGCAGAGCTTCATCGACAACCTCGAAAACCCTGGTCAG
CTGCAAGCTACGATCGAAAGGTTGGCTTCCGTACACCTCAAGATGAGGCCTACCA
TTGGTCTGGAATACTTCAGGCCTCTGCAAGAGAACATTGCACAGTACGTTGCTAG
CGCTCTGGGTGTGGGTGCAGATGACGCAGCTCCTAAACGAAGAGCCTGAGCGGGC
TGGCAAGGC

>BgHb_D 394 bp
SEQ ID NO: 234
GCCTCCCTCGCGCCATCAGGCTCTTCTGCCTACCATTGGTCTGGAATACTTCAGG
CCTCTGCAAGAGAACATTGCACAGTACGTTGCTAGCGCTCTGGGTGTGGGTGCAG
ATGACGCAGCTCCTAAAGCTTGGGAACGTCTCCTGAACGCTTTCAACGAGGTCCT
CAACAGCTTCGCCAACTACAACATCGGACTGAGCGATACGGACAAAGTAGCCCTT
CAGAGCAGTTGGTCTAGGTTAACCGCTGGTGCAGACGGTAAGAGAAATGCTGGTG
TCAGGTTGGTGCTGTGGATGTTCAACAACGTCCCGAACATGCGTGAGAGGTTCAC
CAAGTTCAACGCACGACAGTCAGACGAAGCACTCAAGCGAAGAGCCTGAGCGGGC
TGGCAAGGC

>BgHb_E 394 bp
SEQ ID NO: 235
GCCTCCCTCGCGCCATCAGGCTCTTCTTGCTGGTGTCAGGTTGGTGCTGTGGATG
TTCAACAACGTCCCGAACATGCGTGAGAGGTTCACCAAGTTCAACGCACGACAGT
CAGACGAAGCACTCAAGACCGACGCAGAATTCCTGAAGCAGGTAGACGCAATCAT
CGGTGGTTTCGAGACCCTGATCAACAACCTCAACGACGCAGACCTCTTGCTGAAC
AGACTAGAGAGTCTGGCTGACGAACACCTCGAAAAGAAGCCAGCGATCTCCAGCA
ACTACTTCGGTCCTCTCCAGAAGAACATCCACCTCTTCATCGAGGGTACCCTCAA
CTTTGGGAGTGACTCAGACGAAGCTAGAGCTTGGACTCGAAGAGCCTGAGCGGGC
TGGCAAGGC

Figure 7 (continued)

\>BgHb_F 394 bp
SEQ ID NO: 236
GCCTCCCTCGCGCCATCAGGCTCTTCTCTCCAGCAACTACTTCGGTCCTCTCCAG
AAGAACATCCACCTCTTCATCGAGGGTACCCTCAACTTTGGGAGTGACTCAGACG
AAGCTAGAGCTTGGACTCACTTGGTCGGAGCGTTGAACAAGGTCATCAAGGACCA
CGCTATCCACAACCTGGGTTTGTCCGACATAGACAGAGACGCTCTGGTCTCGTCA
TGGAATCAATTGACCGGTAGGGCAGGAGGTAGTCGAAACGCAGGTACTAACCTCG
TGCTGTGGATGCTCGAAAACGTGCCTAACATGCGTGACCAGTTCTCGAAGTTCAA
CGCTAGGCAGTCCGACGATAACCTGAGAAAGGACGCTCGAAGAGCCTGAGCGGGC
TGGCAAGGC

\>BgHb_G 394 bp
SEQ ID NO: 237
GCCTCCCTCGCGCCATCAGGCTCTTCTTAACCTCGTGCTGTGGATGCTCGAAAAC
GTGCCTAACATGCGTGACCAGTTCTCGAAGTTCAACGCTAGGCAGTCCGACGATA
ACCTGAGAAAGGACGCTGAGTTCGTGCGACAAGTTGACCTGATTACGGGAGGTCT
GGAATCACTCGTCGACAACGTGAACAACCCAATCTTCCTGCAGGAAGCTCTGGTT
AGACTCGCAGATGCTCACCTTAACCTGAAGCCTAGGGTGGGTCTTGAGTACTTTG
GTCCACTGCAGAGGTACATACACGCCTACATCGAAAAGGCACTCGGAGTATCGGC
AGATTCCGCAGCTCCAAGAGCATGGACCGACTTGCTTCGAAGAGCCTGAGCGGGC
TGGCAAGGC

\>BgHb_H 235 bp
SEQ ID NO: 238
GCCTCCCTCGCGCCATCAGGCTCTTCTGTACTTTGGTCCACTGCAGAGGTACATA
CACGCCTACATCGAAAAGGCACTCGGAGTATCGGCAGATTCCGCAGCTCCAAGAG
CATGGACCGACTTGCTTACCGCTTTCAACAACGTCCTGAAGGACAGGCATCACCA
TCACCATCACTAGGACCCAGCTTTCTTGTACAAAGTGGTCCCCCGAAGAGCCTGA
GCGGGCTGGCAAGGC

\>UidA_A 394 bp
SEQ ID NO: 239
GCCTCCCTCGCGCCATCAGGCTCTTCTCGACTGCACGGTGACCAATGCTTCTGGC
GTCAGGCAGCCATCGGAAGCTGTGGTATGGCTGTGCAGGTCGTAAATCACTGCAT
AATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCGGC
TCGTATAATGTGTGGAATTGTGAGCGGATAACAATTTCACACAGGAAACAGAATT
CAATGCTCCGCCCAGTCGAAACCCCAACCCGAGAGATTAAAAAACTGGATGGCCT
GTGGGCATTTAGCCTGGATCGCGAAAACTGCGGCATTCGAAGAGCCTGAGCGGGC
TGGCAAGGC

\>UidA_B 394 bp
SEQ ID NO: 240
GCCTCCCTCGCGCCATCAGGCTCTTCTACAGAATTCAATGCTCCGCCCAGTCGAA
ACCCCAACCCGAGAGATTAAAAAACTGGATGGCCTGTGGGCATTTAGCCTGGATC
GCGAAAACTGCGGCATTGATCAACGTTGGTGGAATCTGCGCTACAGGAAAGTCG
AGCGATTGCAGTACCGGGGAGCTTTAACGATCAGTTTGCGGATGCCGATATTCGC
AACTATGCGGGAACGTTTGGTATCAGCGGGAAGTGTTTATACCGAAAGGCTGGG
CTGGACAGCGCATAGTCTTACGCTTTGATGCCGTGACCCACTATGGCAAAGTGTG
GGTGAACAACCAGGAAGTGATGGAACATCAGGGAGGCCGAAGAGCCTGAGCGGGC
TGGCAAGGC

Figure 7 (continued)

>UidA_C 394 bp
SEQ ID NO: 241
GCCTCCCTCGCGCCATCAGGCTCTTCTAGGCTGGGCTGGACAGCGCATAGTCTTA
CGCTTTGATGCCGTGACCCACTATGGCAAAGTGTGGGTGAACAACCAGGAAGTGA
TGGAACATCAGGGAGGCTACACTCCCTTTGAAGCAGATGTGACCCCGTATGTGAT
TGCGGGCAAATCAGTGAGGATTACCGTGTGCGTCAACAACGAACTGAACTGGCAG
ACAATACCGCCCGGTATGGTTATCACGGACGAGAACGGCAAAAGAAACAGTCGT
ACTTTCACGACTTTTTTAACTATGCCGGCATTCACCGCTCGGTTATGCTGTATAC
GACCCCGAATACCTGGGTCGATGATATCACCGTAGTGCGAAGAGCCTGAGCGGGC
TGGCAAGGC
>UidA_D 394 bp
SEQ ID NO: 242
GCCTCCCTCGCGCCATCAGGCTCTTCTACAGTCGTACTTTCACGACTTTTTTAAC
TATGCCGGCATTCACCGCTCGGTTATGCTGTATACGACCCCGAATACCTGGGTCG
ATGATATCACCGTAGTGACACACGTGGCGCAAGATTGCAATCATGCGAGTGTGGA
TTGGCAAGTCGTGGCGAATGGCGATGTAAGCGTAGAACTAAGGGATGCGGATCAG
CAAGTGGTAGCAACCGGCCAGGGTACCAGCGGTACCTTGCAAGTGGTGAATCCTC
ATCTGTGGCAACCTGGAGAAGGCTATCTGTATGAGCTGTGCGTTACGGCCAAATC
TCAGACGGAATGCGACATCTATCCTCTTCGCGTGGGCCGAAGAGCCTGAGCGGGC
TGGCAAGGC
>UidA_E 394 bp
SEQ ID NO: 243
GCCTCCCTCGCGCCATCAGGCTCTTCTGAATCCTCATCTGTGGCAACCTGGAGAA
GGCTATCTGTATGAGCTGTGCGTTACGGCCAAATCTCAGACGGAATGCGACATCT
ATCCTCTTCGCGTGGGCATTAGATCAGTAGCCGTGAAAGGCGAACAGTTCCTGAT
TAACCACAAGCCGTTCTACTTTACCGGTTTTGGTCGCCATGAAGACGCTGATCTG
CGCGGCAAAGGCTTTGACAACGTCCTGATGGTGCATGATCATGCGCTCATGGATT
GGATAGGGGCCAACAGCTATCGTACTTCCCACTACCCGTATGCCGAAGAGATGTT
AGATTGGCGGACGAACATGGCATAGTCGTGATCGATCGAAGAGCCTGAGCGGGC
TGGCAAGGC
>UidA_F 394 bp
SEQ ID NO: 244
GCCTCCCTCGCGCCATCAGGCTCTTCTCATGGATTGGATAGGGGCCAACAGCTAT
CGTACTTCCCACTACCCGTATGCCGAAGAGATGTTAGATTGGCGGACGAACATG
GCATAGTCGTGATCGATGAAACAGCTGCCGTGGGTTTAACCTTTCACTAGGCAT
TGGGTTCGAAGCCGGCAACAAACCGAAAGAACTGTACAGTGAGGAAGCAGTCAAC
GGAGAAACTCAACAGGCACATCTGCAGGCGATAAAGGAACTGATTGCGCGCGATA
AGAACCATCCGTCCGTCGTGATGTGGAGCATAGCGAATGAACCAGATACGCGTCC
TCAAGGAGCTAGGGAATATTTTGCTCCGCTCGCGGAACGAAGAGCCTGAGCGGGC
TGGCAAGGC

Figure 7 (continued)

>UidA_G 394 bp
SEQ ID NO: 245
GCCTCCCTCGCGCCATCAGGCTCTTCTGCGCGATAAGAACCATCCGTCCGTCGTG
ATGTGGAGCATAGCGAATGAACCAGATACGCGTCCTCAAGGAGCTAGGGAATATT
TTGCTCCGCTCGCGGAAGCTACCAGAAAACTAGATCCCACTCGCCCGATTACTTG
CGTCAACGTGATGTTTTGCGATGCGCATACCGACACCATTAGCGACCTGTTTGAT
GTGCTGTGCCTGAACCGCTATTACGGTTGGTATGTACAGTCAGGGGATCTGGAAA
CTGCGGAGAAAGTACTGGAGAAAGAGCTGCTAGCTTGGCAGGAGAAACTCCATCA
GCCGATTATTATCACGGAATATGGGGTAGACACCCTACGAAGAGCCTGAGCGGGC
TGGCAAGGC

>UidA_H 274 bp
SEQ ID NO: 246
GCCTCCCTCGCGCCATCAGGCTCTTCTTCTGGAAACTGCGGAGAAAGTACTGGAG
AAAGAGCTGCTAGCTTGGCAGGAGAAACTCCATCAGCCGATTATTATCACGGAAT
ATGGGGTAGACACCCTAGCAGGTCTCCATAGCATGTACACGGACATGTGGTCTGA
GGAATACCAGTGTGCCTGGCTGGATATGTATCATCGCGTGTTTGATAGGGTCTCA
GCCGTGGTGGGTGAGCAGGTTTGGAACCGAAGAGCCTGAGCGGGCTGGCAAGGC

>UidA_I 334 bp
SEQ ID NO: 247
GCCTCCCTCGCGCCATCAGGCTCTTCTCACGGACATGTGGTCTGAGGAATACCAG
TGTGCCTGGCTGGATATGTATCATCGCGTGTTTGATAGGGTCTCAGCCGTGGTGG
GTGAGCAGGTTTGGAACTTTGCGGACTTTGCAACGTCTCAAGGGATTTTGCGTGT
GGGCGGGAACAAGAAAGGCATTTTCACCAGAGATCGCAAGCCGAAAAGCGCCGCT
TTTCTATTGCAGAAGCGCTGGACGGGGATGAATTTTGGCGAAAAACCCCAGCAGG
GCGGTAAACAACATCACCATCACCATCACTAACGAAGAGCCTGAGCGGGCTGGCA
AGGC

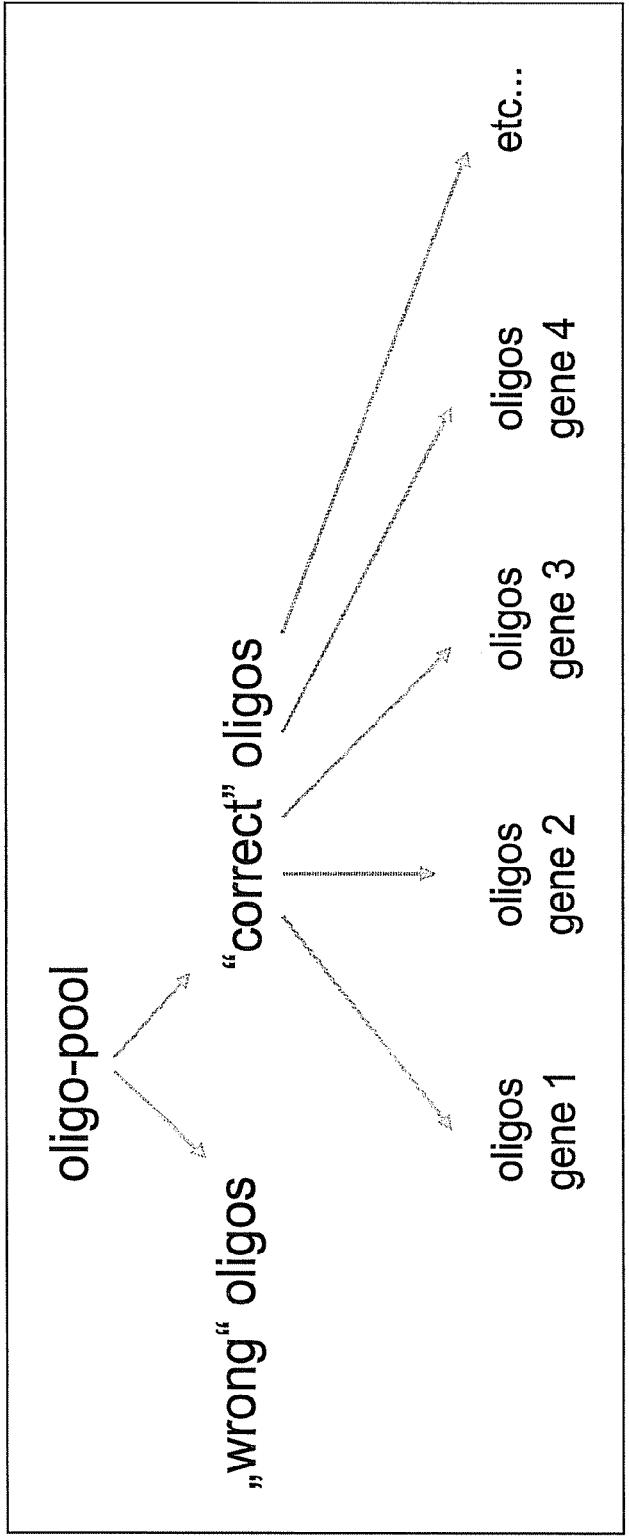

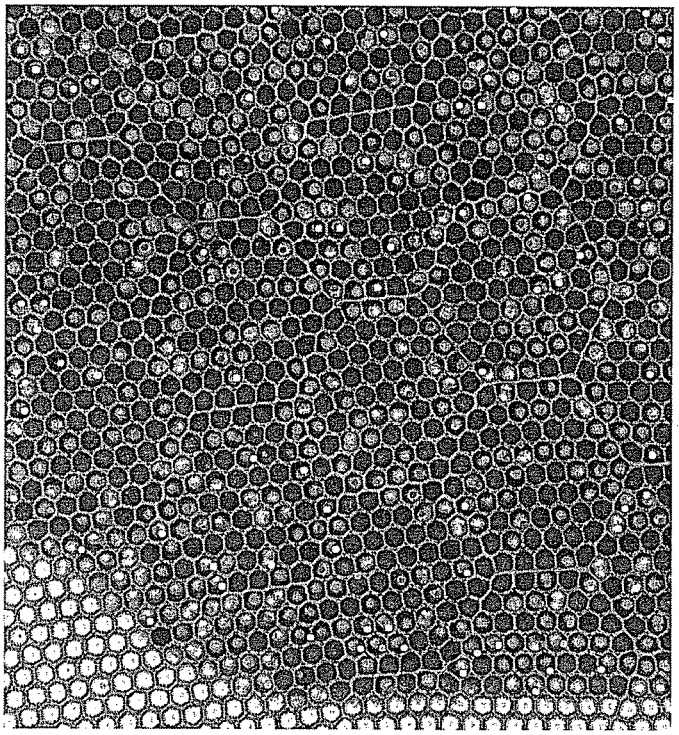
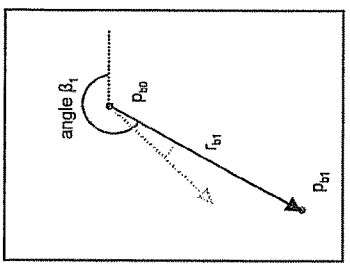
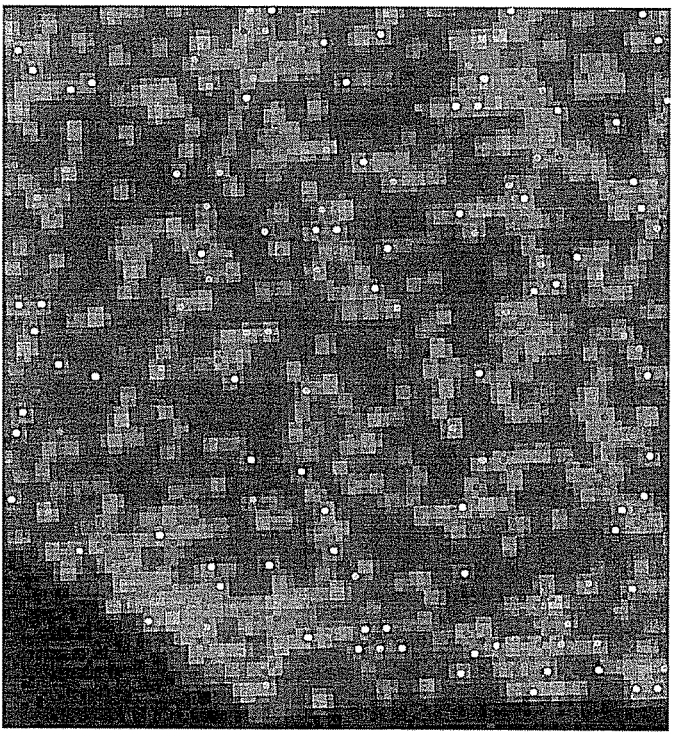
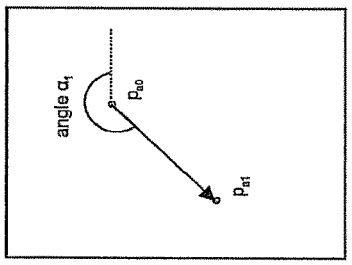
Fig. 14

SYNTHESIS OF SEQUENCE-VERIFIED NUCLEIC ACIDS

CROSS-REFERENCE TO RELATED APPLICATIONS

This application is a continuation of 12/708,783 filed Feb. 19, 2010, now pending; which claims the benefit under 35 USC § 119(e) to U.S. Application Serial No. 61/154,091 filed Feb. 20, 2009, now expired. The disclosure of each of the prior applications is considered part of and is incorporated by reference in the disclosure of this application.

BACKGROUND OF THE INVENTION

Field of the Invention

The invention relates to methods and devices for preparing synthetic nucleic acids.

There is a high demand for synthetic nucleic acids in molecular biology and biomedical research and development. Synthetic nucleic acids (DNA, RNA or their analogues) are mainly prepared using column-based synthesizers.

Particularly important and widespread applications for synthetic nucleic acid polymers are primers for the polymerase chain reaction (PCR) (Critical Reviews in Biochemistry and Molecular Biology 26 (3/4), 301-334, 1991) and the sequencing method according to Sanger (Proc. Nat. Acad. Sci. 74, 5463-5467, 1977).

Synthetic DNA also has a role in the preparation of synthetic genes. Methods of gene synthesis are described for example in U.S. Pat. No. 6,586,211 B1, in PCT/EP2004/013131, in WO 00/13017 A2, in S. Rayner et al., PCR Methods and Applications 8 (7), 741-747, 1998, in WO 90/00626 A1, in EP 385 410 A2, in WO 94/12632 A1, in WO 95/17413 A1, in EP 316 018 A2, in EP 022 242 A2, in L. E. Sindelar and J. M. Jaklevic, Nucl. Acids Res. 23 (6), 982-987, 1995, in D. A. Lashkari, Proc. Nat. Acad. Sci. USA 92 (17), 7912-7915, 1995, and in WO 99/14318 A1, which are incorporated as reference.

Another two fields of application with increasing demand are the production of microarrays or biochips from oligonucleotide probes (1. Nature Genetics, Vol. 21, Supplement (complete), January 1999, 2. Nature Biotechnology, Vol. 16, 981-983, October 1998, 3. Trends in Biotechnology, Vol. 16, 301-306, July 1998) and the preparation of interfering RNA (iRNA or RNAi) for the modulation of gene expression in target cells (PCT/EP01/13968).

The aforesaid fields of application of molecular biology provide valuable contributions in the development of active compounds, the production of active compounds, combinatorial biosynthesis (antibodies, effectors such as growth factors, neurotransmitters etc.), in biotechnology (e.g., enzyme design, pharming, biological production methods, bioreactors etc.), in molecular medicine in tissue engineering, in the development and application of new materials (e.g., materials such as spider silk and mother of pearl), in the development and use of diagnostic agents (microarrays, receptors and antibodies, enzyme design etc.) or in environmental engineering (specialized or tailor-made microorganisms, production methods, remediation, sensors etc.). The method according to the invention can thus be employed in all these areas.

BACKGROUND INFORMATION

Prior Art

The most common method for the preparation of synthetic nucleic acids is based on the fundamental work of Caruthers and is known as the phosphitamide method (M. H. Caruthers, Methods in Enzymology 154, 287-313, 1987). The sequence of the resultant molecules can be controlled by the order of synthesis. Other methods, such as the H-phosphonate method, serve the same purpose of successive synthesis of a polymer from its subunits, but have not found such widespread application as the method according to Caruthers.

To make it possible to automate the chemical method of polymer synthesis from subunits, solid phases are generally employed, on which the growing molecular chain is anchored. On completion of synthesis it is split off, which requires a suitable linker between the actual polymer and the solid phase. For automation, as a rule the method employs solid phases in the form of activated particles, which are packed in a column, e.g., controlled pore glass (CPG). These solid phases as a rule only carry one specifically removable type of oligo with a programmed sequence. The individual synthesis reagents are then added in a controllable manner in an automatic machine, which mainly provides the automated addition of the individual reagents to the solid phase. The quantity of molecules synthesized can be controlled by the amount of support material and the size of the reaction batches. For the aforementioned molecular-biological methods, these amounts are either sufficient or even too high (e.g., in the case of PCR primers). Some degree of parallel operation for production of a multiplicity of different sequences is achieved through arranging several columns in an assembly of apparatus. Thus, equipment with 96 parallel columns is known by a person skilled in the art.

A variant and further development for the production of synthetic nucleic acids is the in situ synthesis of microarrays (array arrangement of nucleic acids in a matrix). This is carried out on a substrate that is loaded with a multiplicity of different sequences during the synthesis. The great advantage of the in situ synthesis methods for microarrays is the preparation of a multiplicity of oligomers of different and defined sequence at addressable locations on a common support. The synthesis has recourse to a manageable set of feed materials (in the case of DNA microarrays, as a rule the 4 bases A, G, T and C) and from these it builds up any sequences of nucleic acid polymers.

The individual molecular species can be demarcated on the one hand by separate fluidic compartments for addition of the synthesis feed materials, as is the case e.g., in the so-called in situ spotting method or piezoelectric techniques, based on inkjet printing technology (A. Blanchard, in Genetic Engineering, Principles and Methods, Vol. 20, Ed. J. Sedlow, 111-124, Plenum Press; A. P. Blanchard, R. J. Kaiser, L. E. Hood, High-Density Oligonucleotide Arrays, Biosens. & Bioelectronics 11, 687, 1996).

An alternative method is the spatially-resolved activation of synthesis sites, which is possible through selective illumination, through selective or spatially-resolved generation of activation reagents (deprotection reagents) or through selective addition of activation reagents (deprotection reagents).

Examples of the methods known to date for the in situ synthesis of microarrays are photolithographic light-based synthesis (McGall, G. et al.; J. Amer. Chem. Soc. 119; 5081-5090; 1997), projector-based light-based synthesis (PCT/EP99/06317), fluidic synthesis by means of physical separation of the reaction spaces (known by a person skilled in the art from the work of Prof. E. Southern, Oxford, UK, and of the company Oxford Gene Technologies, Oxford, UK), indirect projector-based light-controlled synthesis by light-activated photo-acids and suitable reaction chambers or physically separated reaction spaces in a reaction support, electronically induced synthesis by spatially-resolved deprotection on individual electrodes on the support using proton production induced by the electrodes (known from, among others, the products of the company Combimatrix), and fluidic synthesis by spatially-resolved deposition of the activated synthesis monomers (known from A. Blanchard, in Genetic Engineering, Principles and Methods, Vol. 20, Ed. J. Sedlow, 111-124, Plenum Press; A. P. Blanchard, R. J. Kaiser, L. E. Hood, High-Density Oligonucleotide Arrays, Biosens. & Bioelectronics 11, 687, 1996).

Methods of preparation of synthetic nucleic acids, in particular nucleic acid double strands on a common solid support, are also known from WO 00/49142, WO 2005/051970 and WO 2008/022789, the contents of which are herein incorporated by reference.

Disadvantages of the Prior Art

The high error rate and cost of commercially-available oligonucleotides are major obstacles to synthetic molecular biology approaches, including the production of high quality variant libraries and custom gene synthesis. Error rates of conventional oligonucleotides produced by phosphoramidite chemistries typically range from $1/100$ to $1/300$.

In gene synthesis, the impact of the oligonucleotide input error rate is particularly severe at longer lengths where many clones often need to be sequenced in order to find an error-free clone. Smaller DNA fragments can be cloned, propagated in bacteria and sequence-verified before assembling to the final length, but then the researcher suffers from multiple labor-intensive cloning steps, consumable expenses, and the very real possibility of missing parts.

The types of errors which one discovers in oligonucleotides upon DNA sequencing can include small and large deletions, substitutions, and/or insertions. Since the biological activity of a gene and its product(s) can be seriously impaired or completely disrupted by any one of these errors, it would be a substantial improvement if error-free oligonucleotides were available and an affordable starting material for gene synthesis.

One of ordinary skill in the art, or, an expert manufacturer of cloned genes could purchase conventional, complementary oligonucleotides from a commercial oligonucleotide supplier; and then clone and sequence the oligonucleotides to identify the correct parts for gene assembly. However, the raw material cost and downstream processing costs to assemble full length genes from such sequence-verified oligonucleotides would be orders of magnitude more expensive than cloned, full length genes purchased on the open market. The primary cost factors for gene synthesis are conventional oligonucleotide cost, Sanger sequence costs, and labor.

The parallel synthesis of high density oligonucleotides on microarrays from companies such as Affymetrix, Febit, Nimblegen (Roche), and others offers access to lower cost oligonucleotides, although the higher error rates and complexity of the mixtures presents formidable challenges to gene assembly efforts.

Genes can be assembled from oligonucleotides derived from microarrays, but ordinarily, gene-specific amplification is required to extract particular components in concentrations and at the lower levels of complexity conducive to assembly. Amplification bias, high error rate, cross-contamination, PCR failure, or spurious PCR products can all confound efforts to reliably assemble microarray-derived oligonucleotides into genes. As disclosed in the description of the invention below, the aforementioned host of technical obstacles can be overcome in a cost-effective manner, and this innovation has the potential to transform the scope and economics of the field of Synthetic Biology.

The fastest available Sanger sequencing instrument (e.g., ABI 3730xl) is far too slow and expensive to sequence complex oligonucleotide libraries. Additionally, if amplified oligonucleotides were used as template DNA for Sanger sequencing, the sequences would be highly heterogeneous unless the oligonucleotide DNA was first cloned and isolated from bacterial cells. By comparison to the PCR methods described in the next paragraph, generating clonal DNA in vivo is cost-prohibitive, requires specialized equipment and facilities, is contamination-prone, and is labor intensive.

So-called Next-Gen Sequencing (NGS) instruments and chemistries are available from ABI (Solid), Roche (454), and Illumina (Solexa). There are also other non-Sanger based sequencing technologies under development at Pacific Biosciences, Helicos, and Danaher. NGS technologies don't require in vivo cloning for the preparation of clonal sequencing template, but instead, use emulsion PCR or bridge amplification on solid substrates. The hallmark of NGS is short (17-200 nt) but massively parallel sequencing reads, generating an output of useable data ranging from 300 Mb to 1 Gb per day per instrument. Recently, 454 demonstrated 400 base long reads with. their planned XLR HD product release, making their technology particularly well-suited for sequencing the entire length of long oligonucleotides and PCR products.

Integrating the parallel processing capabilities of NGS with microarray oligonucleotide synthesis enables low-cost manufacturing of near-perfect DNA components for gene synthesis and for other molecular biology procedures which benefit from stringent quality control, and is the subject of this invention.

SUMMARY OF THE INVENTION

The present invention relates to methods of preparation of synthetic nucleic acids from sequence-verified building blocks. The methods allow the error-free synthesis of nucleic acid molecules, thereby reducing the costs and efforts of such methods.

A first aspect of the present invention relates to a method to retrieve sequence verified nucleic acids from a plate, carrier or/and substrate, comprising the steps:

(1) provision of a mixture of nucleic acids, (2) turning the nucleic acid mixture into a clonal library, (3) sequencing the clonal library, (4) retrieval of the sequence-verified nucleic acid molecules, (5) optionally use of the retrieved molecules in continuative steps/procedures, or/and (6) optionally repeating steps (2)-(5) at least one time.

A further aspect of the present invention relates to a method for reformatting a library or mix of nucleic acid sequences with n members in up to n separate vessels, fractions, ports or/and wells.

Still a further aspect of the present invention refers to a process to in vitro clone, sequence and/or make available for separate handling or recombination a set of nucleic acids with 2, 10, 100, 1000, 10.000, 100.000, $10^6$, $10^7$, $10^8$, $10^9$, $10^{10}$, $10^{11}$ or up to $10^{20}$ defined sequence members.

Still a further aspect of the present invention relates to a method to physically separate, in vitro amplify, to form a clone and sequence set of nucleic acids by means of using a parallel sequencing process.

Still a further aspect of the invention is an apparatus with alignment capability to identify locations or beads with clonal DNA of known sequence.

Still a further aspect of the present invention is an apparatus for retrieval of clonal sequence-verified nucleic acid fragments, including
  (a) unit/means to link the sequence-information to the physical position or location of the nucleic acid fragment,
  (b) unit/means to release location-specific the sequence-verified nucleic acid fragments from the carrier (e.g., based on the sequence and location information provided), or/and
  (c) unit/means to retrieve the released sequence-verified nucleic acid fragments from the carrier.

Still a further aspect of the present invention is an apparatus for producing sequence-verified nucleic acid fragments, particularly clonal sequence-verified nucleic acid fragments, including
  (a) unit/means to generate a clonal representation of nucleic acid mixture,
  (b) unit/means to sequence the clonal representation of nucleic acid mixture, and generating the sequence-information and the physical location information for each of the nucleic acid fragments,
  (c) unit/means to link the sequence-information to the physical position or location of the nucleic acid fragments,
  (d) unit/means to release the sequence-verified nucleic acid fragments from the carrier, in particular based on the sequence and location information provided,
  (e) unit/means to retrieve the released sequence-verified nucleic acid fragments from the carrier, or/and
  (f) optional: unit/means to reformat (and optionally store away) the retrieved sequence-verified nucleic acid fragments.

Still a further aspect of the present invention is a method for isolation of a nucleic acid with the desired correct sequence from a mixture of nucleic acids, comprising the steps
  (a) monoclonizing the mixture of nucleic acids,
  (b) sequencing the monoclonized nucleic acids of step (a),
  (c) identifying a nucleic acid with the desired sequence from the nucleic acids of step (b), and
  (d) isolating the nucleic acid from step (c).

Still a further aspect of the present invention is a method of sequencing at least one nucleic acid in a mixture comprising assembled nucleic acids, which possibly contain defective nucleotides, comprising the steps:
  (a) amplification of a mixture comprising assembled nucleic acids, which are in each case built up from 2 or more nucleic acid fragments, to clonal populations,
  (b) sequencing of at least one clonal population from step (a), and
  (c) optionally isolation of at least one nucleic acid, which contains defects, or/and at least one nucleic acid, which is correct.

Still a further aspect of the present invention is the production of defined nucleic acid-based affinity matrices. For this purpose the nucleic acid mixture that is provided was designed to bind to defined parts or regions of a high complex nucleic acid population (e.g., human genomic dna). In dependance of the technique used to provide these nucleic acid molecules (e.g., column synthesis, microarray synthesis, natural sources) more or less sequence errors. The present invention is used to physically individualize ail of the members of the mixture and assign a sequence to all. Next, these members that show the right sequence can be retrieved by the disclosed methods and used for enrichment purposes (enrichment, sequence capture, hybselect) downstream.

BRIEF DESCRIPTION OF THE DRAWINGS

The present invention is further illustrated by the following Figures and Examples.
Figure Legends
FIG. 1.

FIG. 2:
Sequence alignments of the beads from FIG. 1B-D are shown.

$P_{a0}$, $P_{b0}$ and $P_{a1}$, $P_{b1}$ are manually selected corresponding reference points in the sequencer image or the microscope picture respectively.

$p_{a1}$ and $p_{b1}$ were converted from Cartesian to polar coordinates using $p_{a0}$ or $p_{b0}$ respectively as origin.

$x_{a1}$, $y_{a1}$ à $r_{a1}$, $\alpha_1$
$x_{b1}$, $y_{b1}$ à $r_{b1}$, $\beta_1$ A deviation angle and a gauge factor were determined
deviation angle=$\beta_1-\alpha_1$
gauge factor=$r_{b1}/r_{a1}$
all positions were mapped by following steps:
$x_{ai}$, yai à $r_{ai}$, $\alpha_i$ conversion into polar coordinates
$\beta_i$=deviation angle+$\alpha_i$ correction of angle
$r_{bi}$=gauge factor*$r_{ai}$ correction of radius
$r_{bi}$, $\beta_i$ à $x_{bi}$, $y_{bi}$ conversion into Cartesian coordinates for mapping in microscope picture

FIG. 4:

Primer sequences.

FIGS. 5A and 5B:

Construction oligonucleotides for the β-D-glucuronidase (UidA) gene (FIG. 5A) and the *Biomphalaria glabrata* hemoglobin (BgHb) gene (FIG. 5B) are shown.

FIGS. 6A and 6B:

The sequences for UidA (FIG. 6A) and BgHb (FIG. 6B) are shown.

FIG. 7:

The identified BgHb and UidA gene fragments including the sequencing primers are shown.

FIG. 8:

A schematic flow diagram of a preferred embodiment of the present invention (Megacloner) is shown.

FIG. 9:

A schematic picture of a rapid assembly method of sequence-verified (clone-ready) variants by non-contact acoustic dispensary is shown.

FIG. 10:

319 beads (each of them a clonal bead from a picotiter plate of a 454 ngs sequence instrument) carrying different nucleic acid sequences were picked. The DNA was amplified and pooled. The pool was sequences on an Illumina GAII ngs instrument for sequence verification.

FIG. 11:

Schematic illustration showing the provided convergence of technology provided by a preferred embodiment of the present invention called Megacloner.

Figure 12A:
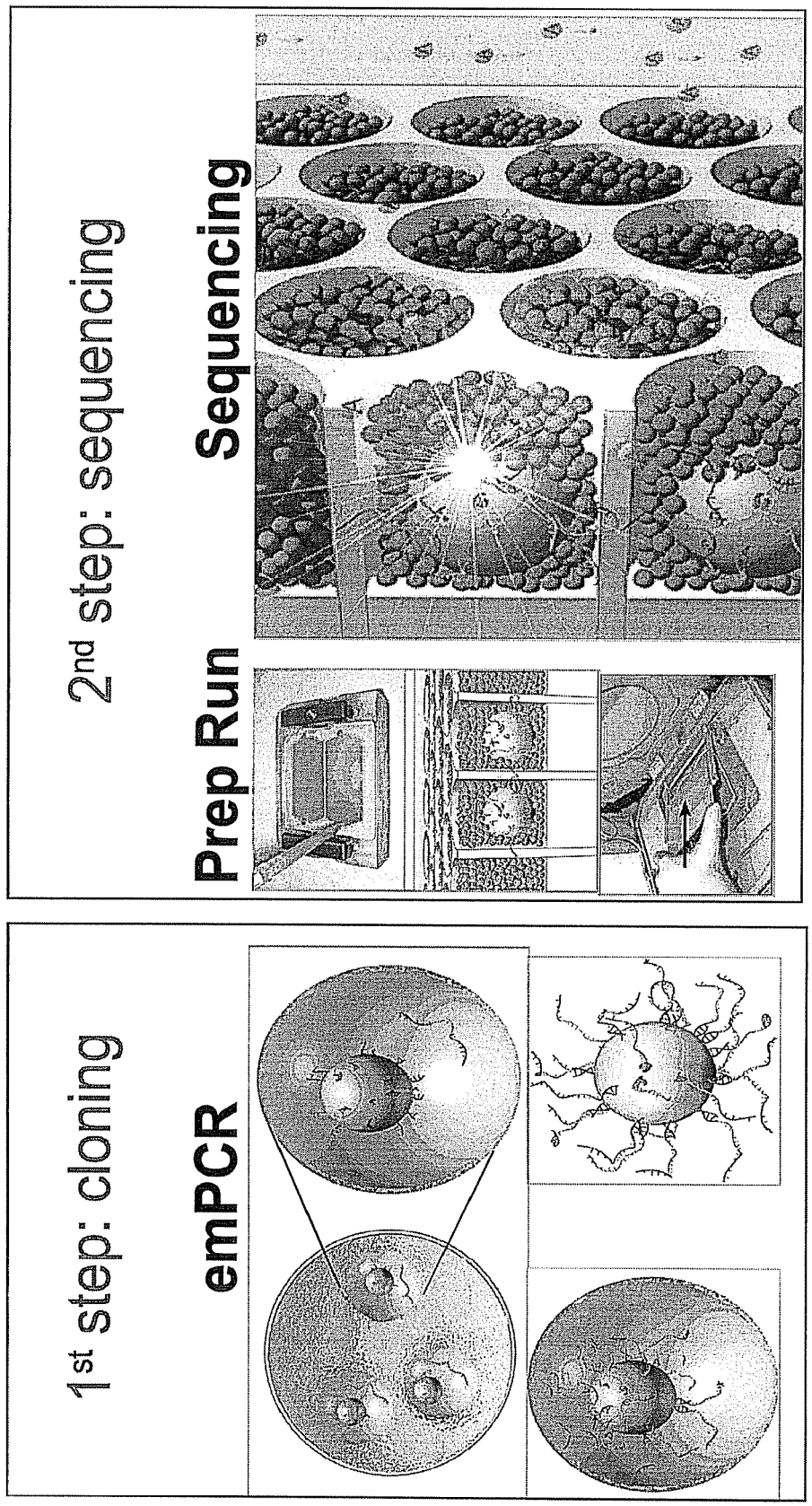
Figure 12B:
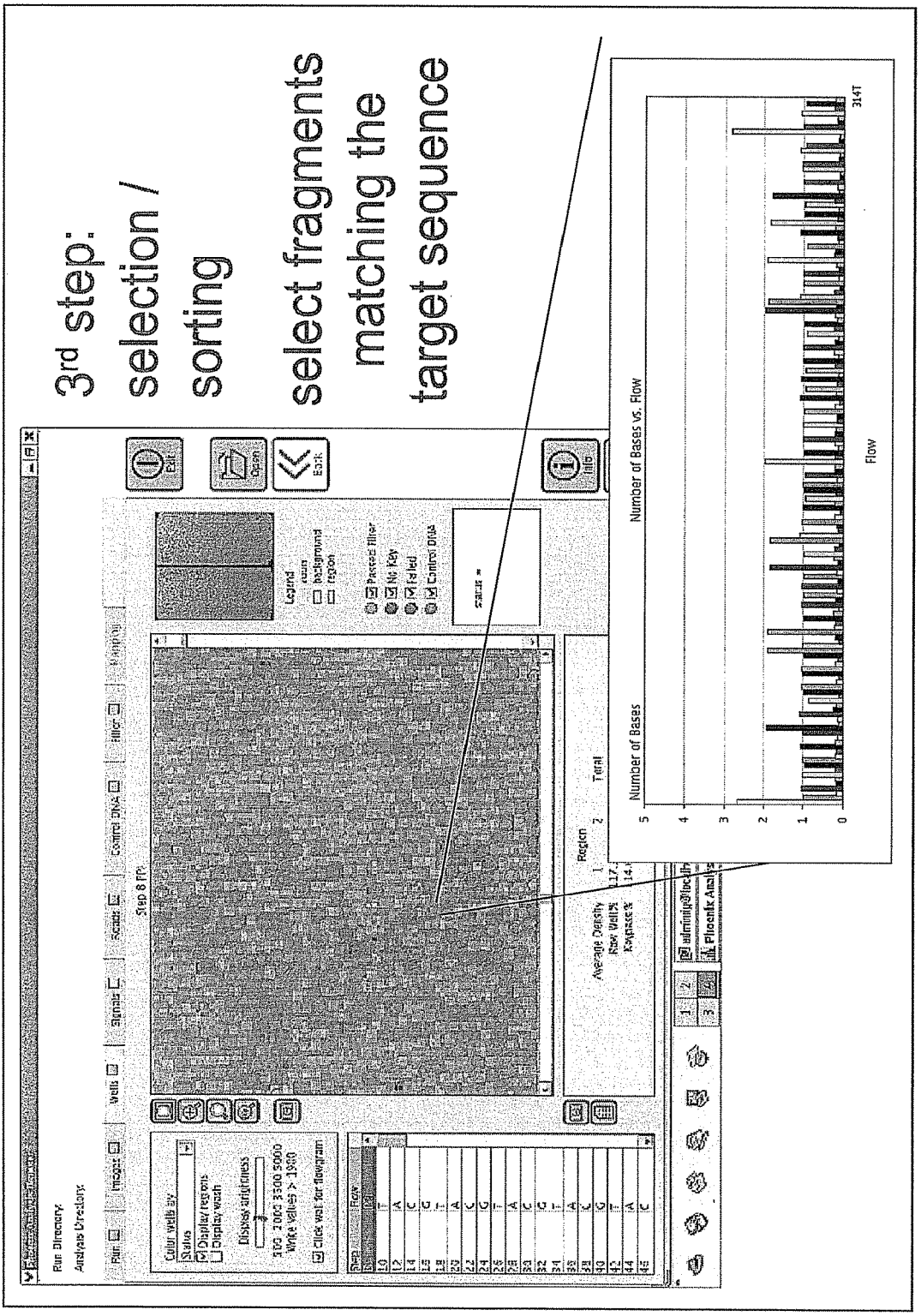
Figure 12C:
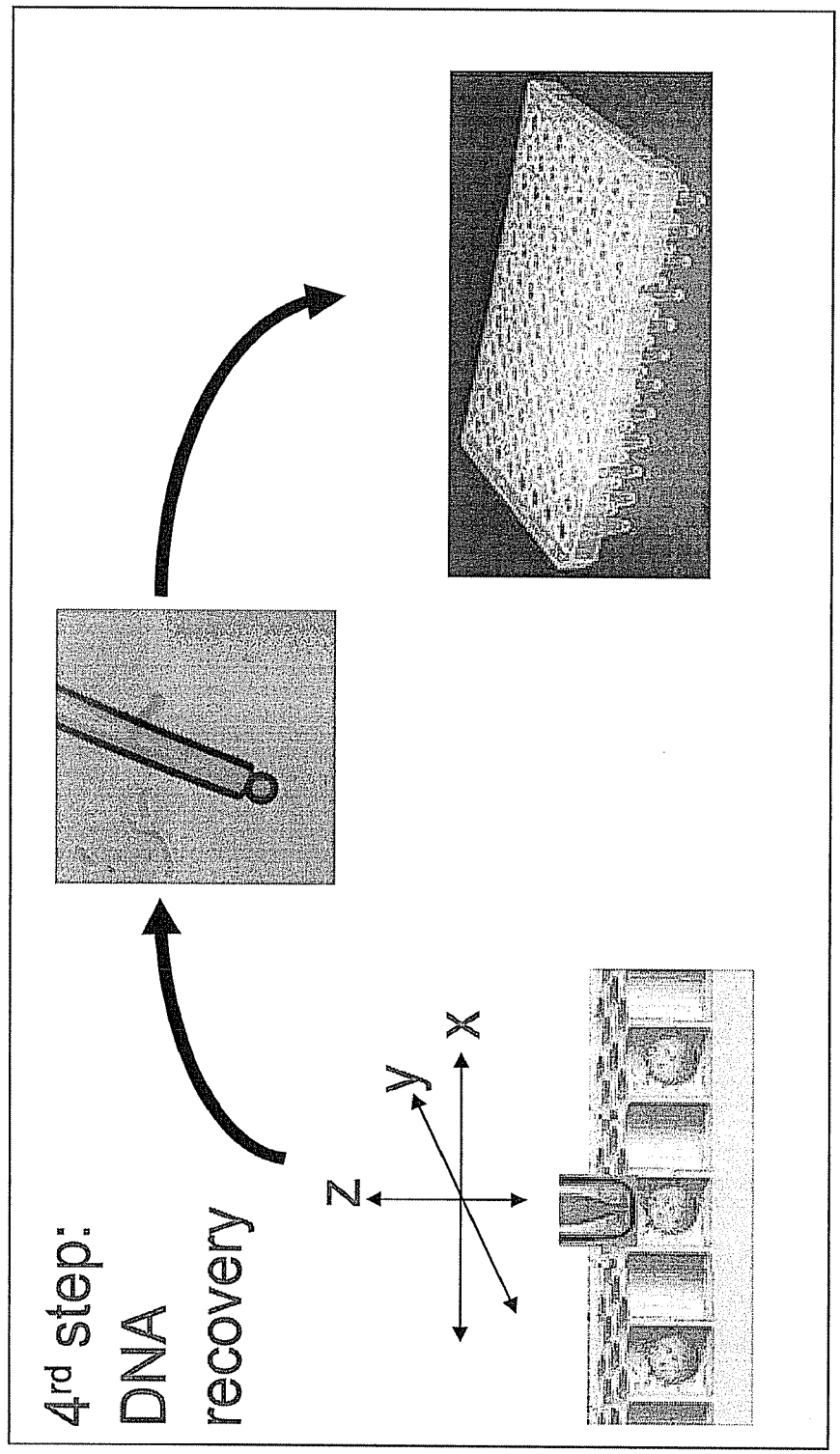
Figure 13:
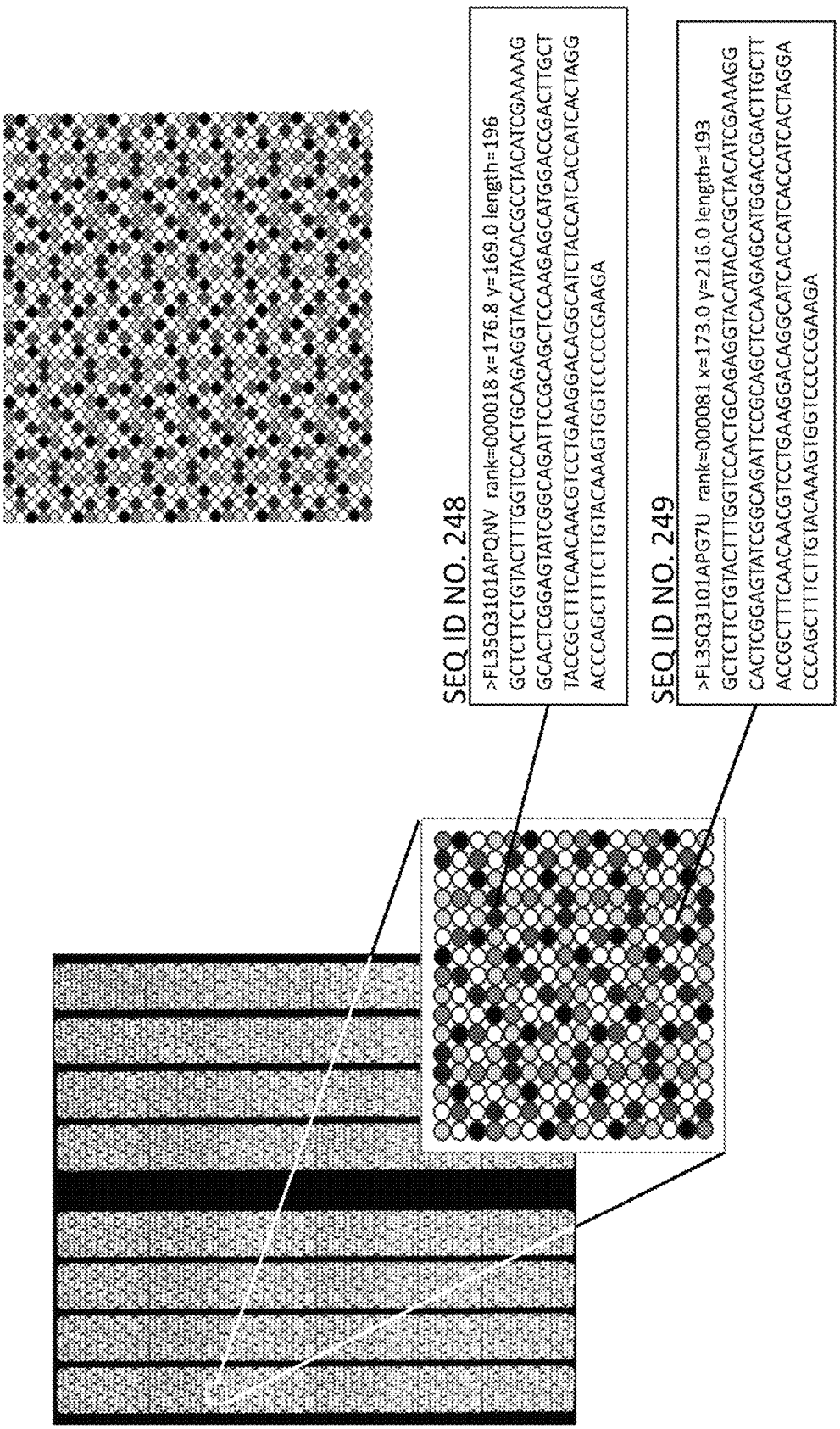
Figure 15:
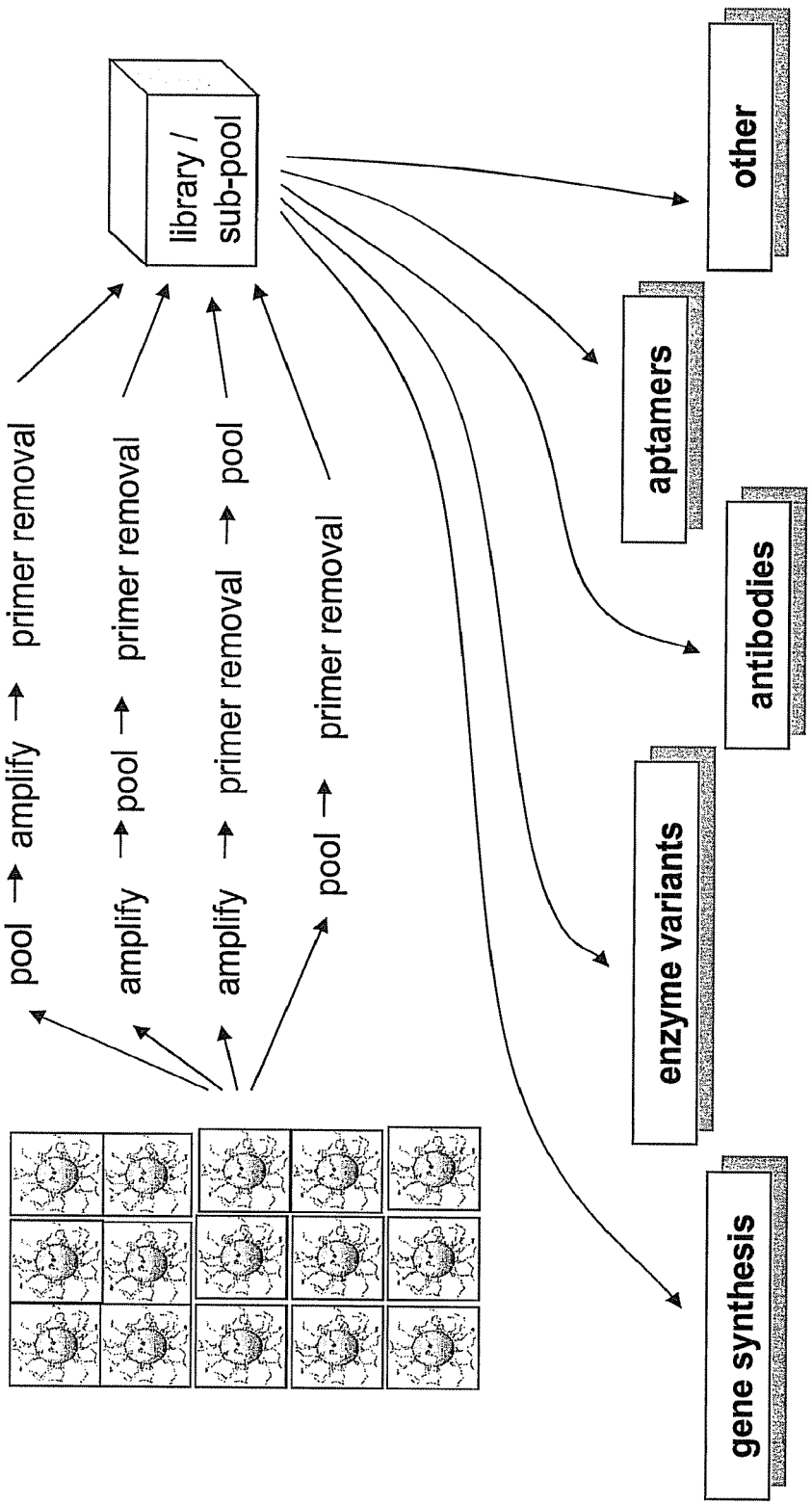

FIGS. 12A-12C:

Schematic illustration showing a Megacloner workflow comprising the steps (FIG. 12A) (1) Cloning, (2) Sequencing, (FIG. 12B) (3) Selecting/sorting and (FIG. 12C) (4) DNA recovery e.g., using microactuators & pipettes.

Figure 1A:
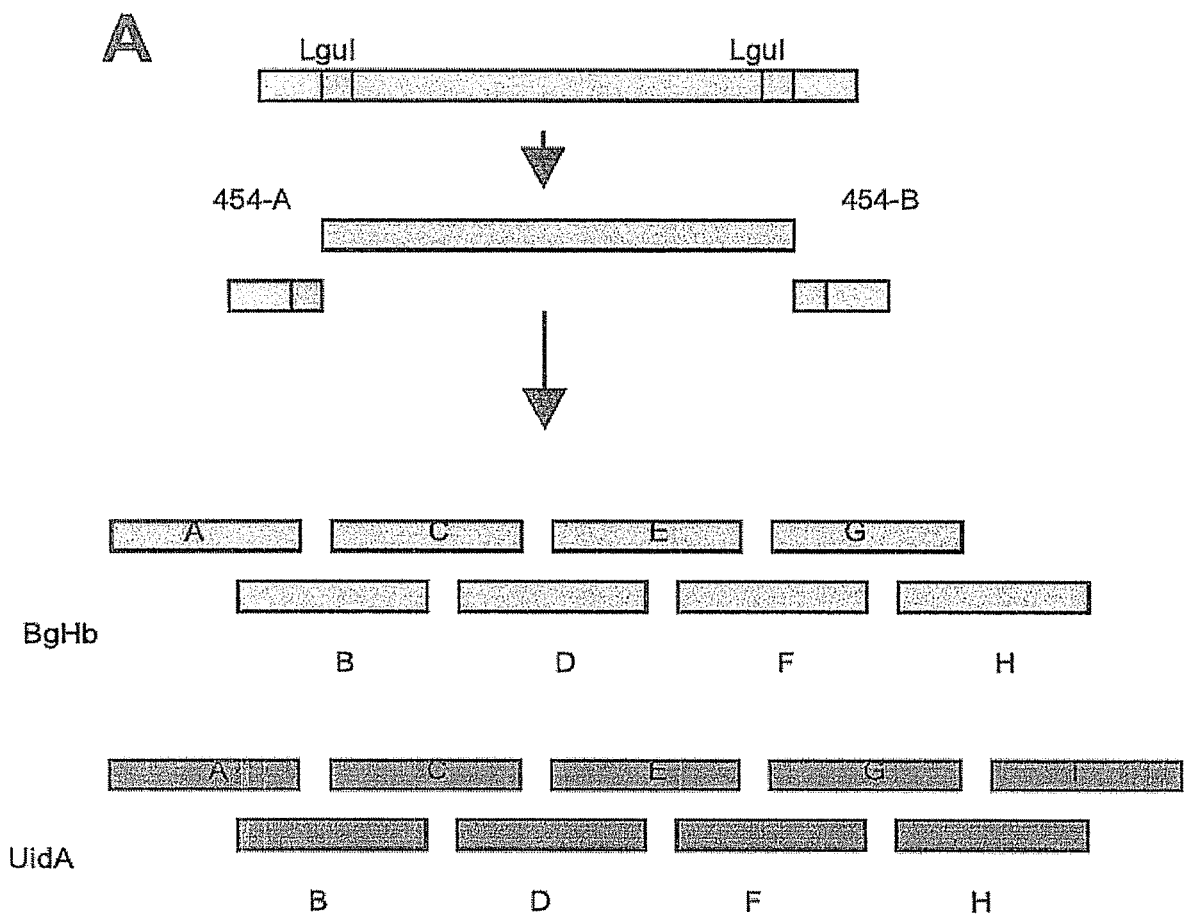
FIG. 1A) Scheme for gene assembly. After removal of primer regions with LugI, the gene fragments were used to assemble two genes (β-D-Glucuronidase (UidA) and *Biomphalaria glabrata* hemoglobin (BgHb)) consisting out of 8 or 9 overlapping parts respectively.
Figure 1B:
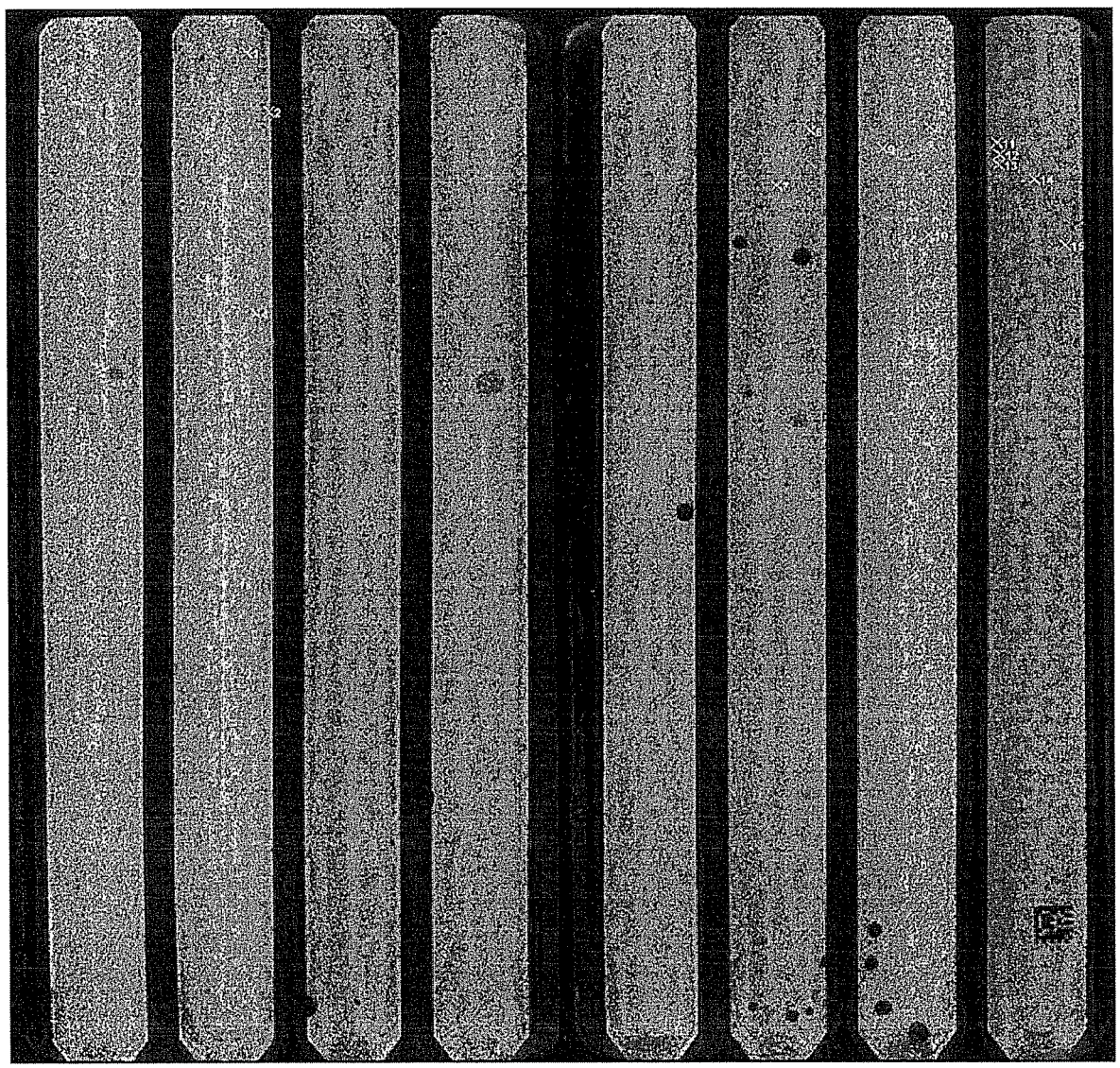
FIG. 1B) Raw image of the entire sequencing plate divided in 8 areas. Positions of extracted beads carrying unique sequences are marked (upper part). The x- and y-positions of the beads on the plate are indicated (lower part).

FIG. 13:

Bead localization in a raw image of an entire sequence plate divided into eight areas (cf. see also FIG. 1B).

Figure 1C:
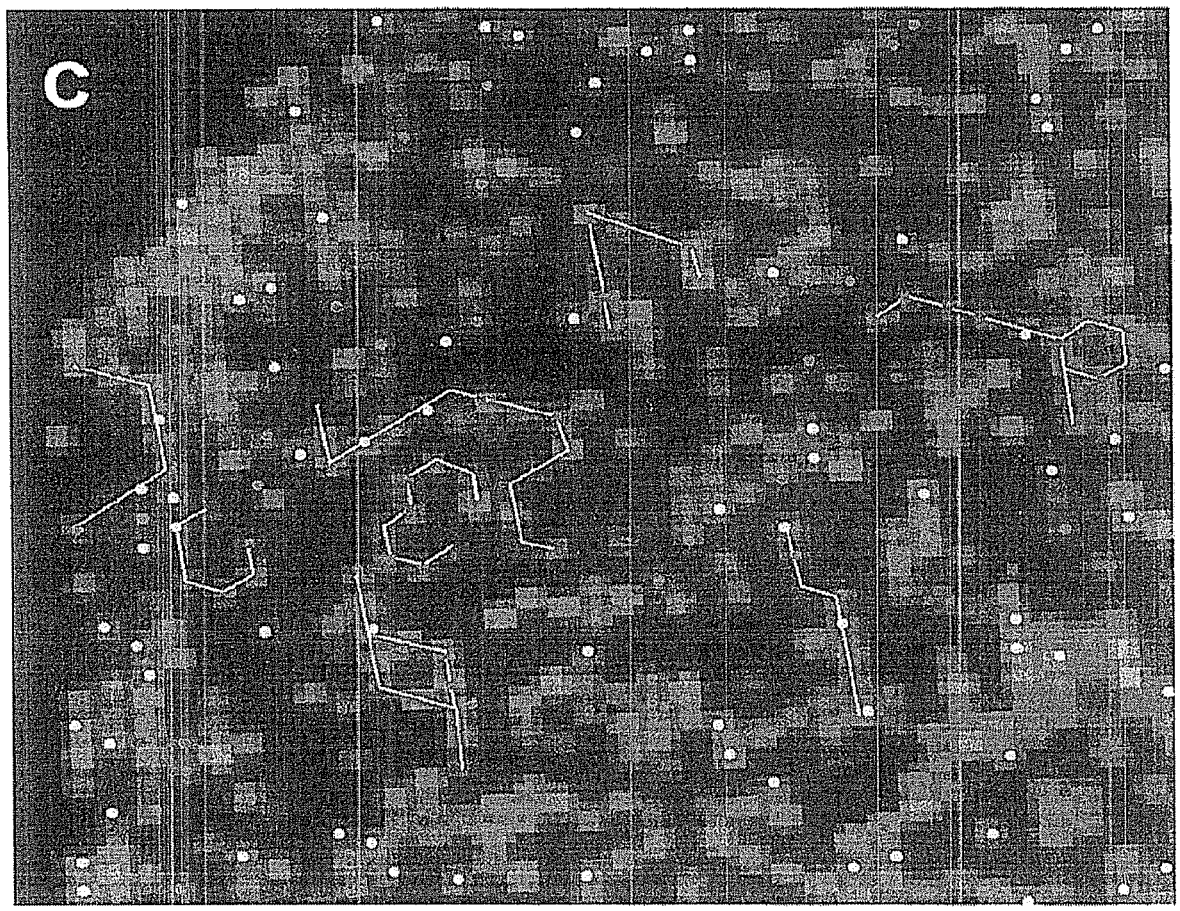
FIG. 1C) Magnified section of the raw image from the upper left corner of lane 6 (white box picture B). For recovery of the beads carrying correct sequences, the corresponding wells have been marked with dots using the coordinates given for each sequence. The colors represent different fragments (red: UidA_F, yellow: UidA_G, green: BgHb_G).
Figure 1D:
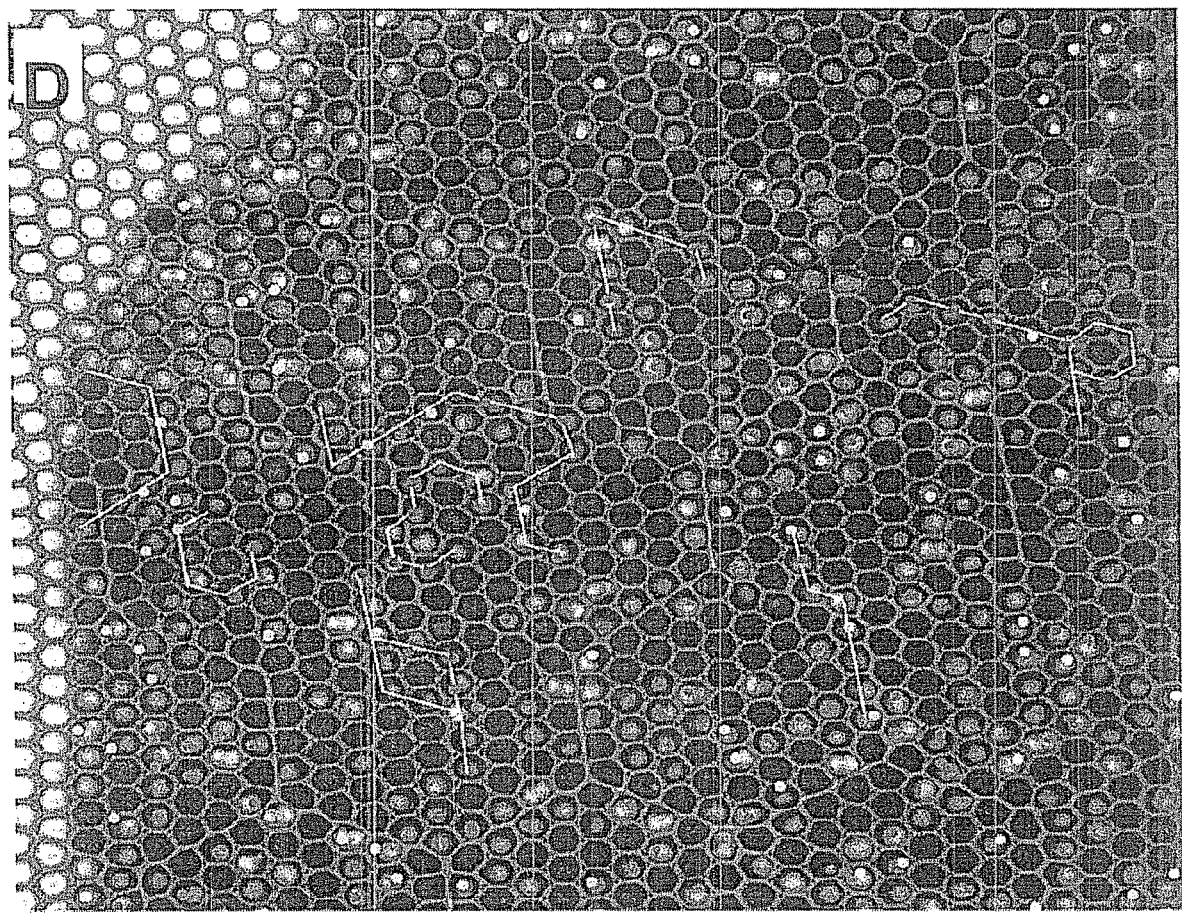
FIG. 1D) The coordinates were mapped into a microscope picture that was used as guideline for manual extraction. For orientation on the plate patterns of bead containing wells (white lines in C and D) have been used.
Figures 3, 4:
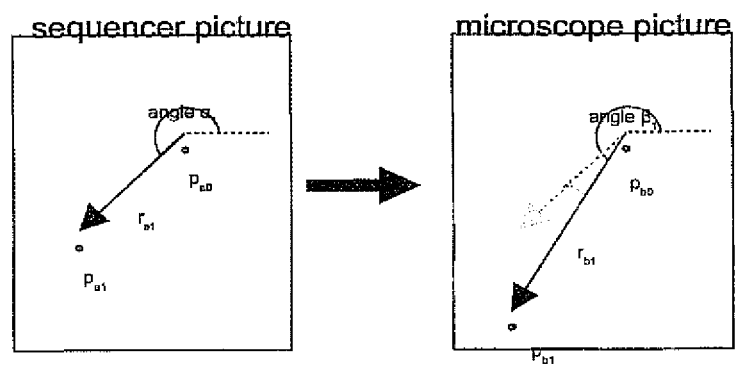
FIG. 3:
The mapping algorithm for transferring the sequences picture into a microscope picture is shown.
Figure 8:
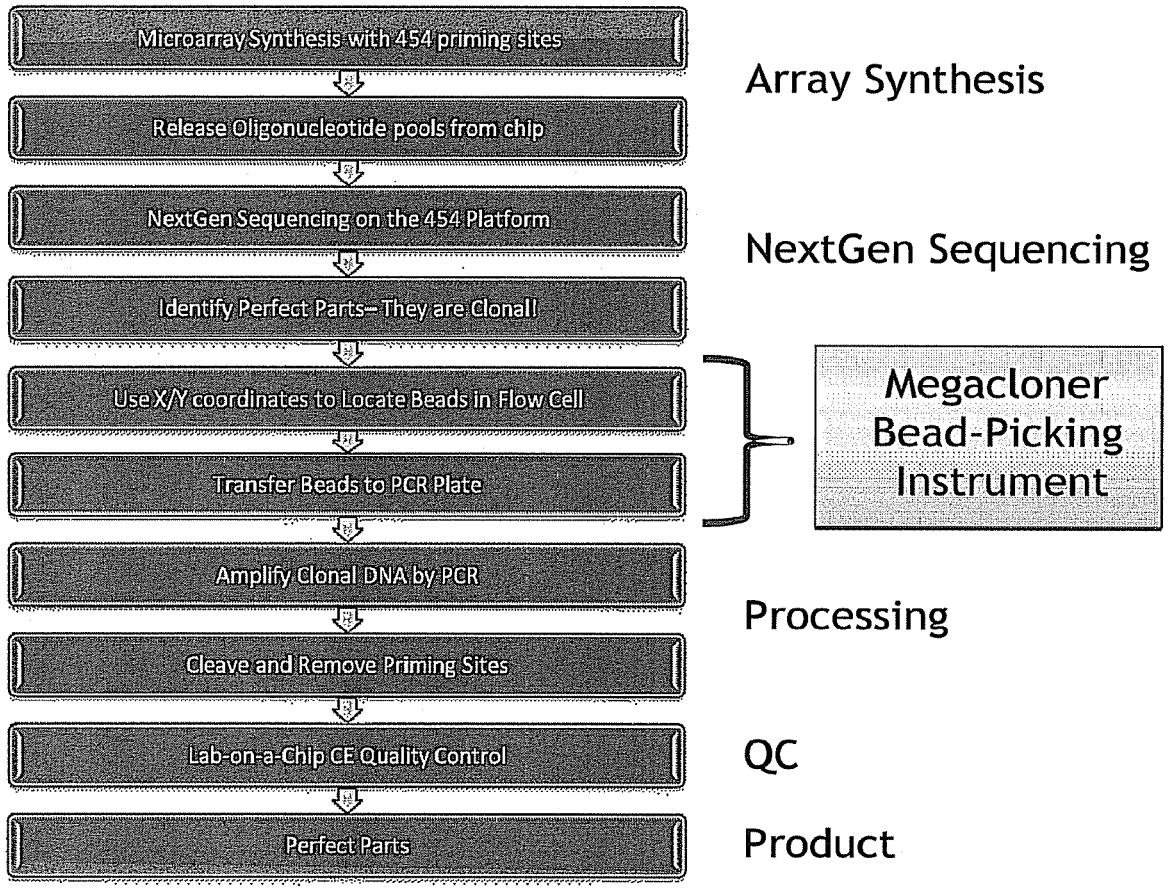
Figure 9:
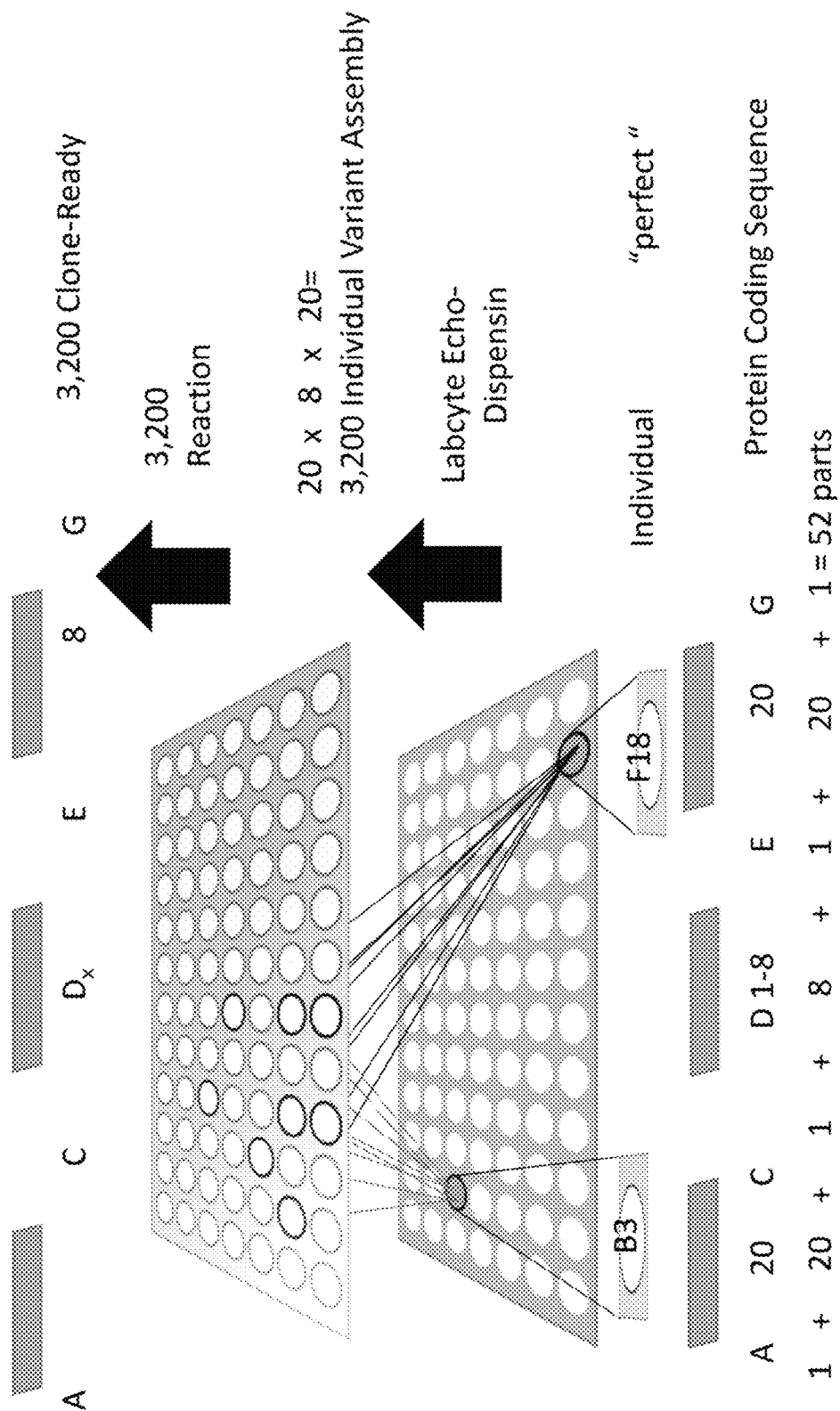

FIG. 14:

Position transfer, i.e., from a sequencer picture to a microscope picture (see also FIGS. 1C and 1D and FIG. 3).

FIG. 15:

Applications provided by the methods and apparatuses according to the present invention.

DETAILED DESCRIPTION OF THE INVENTION

General Description

In general, the present invention relates to the preparation of synthetic nucleic acids of optional sequence, in particular nucleic acid double strands, through the preparation of suitable solid-phase-supported synthetic libraries. Moreover, an improved method is to be provided for the preparation of synthetic nucleic acids of optional sequence, in particular nucleic acid double strands, through the preparation of suitable solid-phase-supported synthetic libraries and the subsequent joining together of at least two nucleic acid fragments from the library through binding or covalent linkage of these two nucleic acid fragments to one another, wherein preparation of the library includes control of the quantitative proportions of the constituents of the library to one another.

The nucleic acid fragments are joined together preferably by a specific hybridization reaction between overlapping regions of mutually complementary segments of the nucleic acid fragments, thereby obtaining longer synthetic double-stranded nucleic acids. The individual sequence segments used for building up longer nucleic acids preferably have a length of 20-100 or 20-300 nucleotide building blocks, preferably of 25-50 or 25-100 nucleotide building blocks, for example about 30 nucleotide building blocks. The sequence segments are preferably selected in such a way that they at least partially overlap a sequence segment of the antisense strand of the complementary nucleic acid that is to be synthesized, so that the nucleic acid strand to be synthesized can be built up by hybridization of individual sequence segments. In an alternative embodiment, the sequence segments are preferably selected so that the sequence segments on both strands of the nucleic acid to be synthesized completely overlap, and accordingly preparation of a more or less complete double strand now only requires covalent linkage of the phosphodiester backbone. The length of the complementary regions or overlaps between individual fragments is e.g., 10-50 or 10-100 nucleotide building blocks, preferably 12-25 or 20-80 nucleotide building blocks, especially preferably about 15-20 nucleotide building blocks and most preferably about 15 or about 20 nucleotide building blocks. If the overlapping or complementarity region between two nucleic acid fragments has a high AT content, e.g., an AT content >50%, preferably an AT content >60%, especially preferably an AT content >65%, the binding constant is lower in comparison with GC-richer sequences. Accordingly, for thermodynamic reasons, hybridization between these fragments may be of comparatively low efficiency. This can have an influence on the assembly of 2 or more fragments. A possible sequence-dependent consequence is a reduced yield of nucleic acid double strands with the correct target sequence.

The thermodynamic relations during assembly from 2 or more fragments may be influenced by controlling or by controlling and regulating the quantitative proportions of the fragments in a reaction batch, in order to improve the yield of correct nucleic acid double strands. In particular, the thermodynamic parameters are modulated in a reaction for binding at least 2 nucleic acid fragments to one another. Modulation of the thermodynamic parameters means, in particular, that the binding of the two nucleic acid fragments to one another, which is subject to the law of mass action, is improved. It is especially preferable for the modulation of the thermodynamic parameters in the reaction to comprise control of the quantitative proportions of individual nucleic acid fragments, in particular through the use of larger amounts of nucleic acid fragments that have a high proportion of AT. If at least some nucleic acid fragments, for modulation of their thermodynamic parameters in the reaction of at least 2 nucleic acid fragments, are used in an increased amount relative to other fragments, this can be achieved for example in that at least some nucleic acid fragments, which have a high AT content, are used in an increased amount relative to other fragments.

By controlling the quantitative proportions of individual nucleic acid fragments, in particular by using larger amounts of nucleic acid fragments that have a high proportion of AT, the yield of correct hybridization products and therefore also the yield of correct nucleic acid double strands can be improved. The quantity of the population of the corresponding nucleic acid fragments can thus be improved by preferably ≥10%, especially preferably ≥50% or even more, e.g., by up to a factor of 100 or 1000 relative to other nucleic acid fragments without a high proportion of AT.

Apart from the proportion of AT, there are also other parameters that have an influence on the yield of target sequences. These include the varying synthesis efficiency of the individual fragments or oligonucleotides during extension in the synthesis process. A person skilled in the art knows, for example, that building block G in phosphoramidite methods couples at lower yield to the polymer strand that is to be extended than the other nucleotide building blocks. Moreover, a person skilled in the art is aware of dependences of the synthesis efficiency on the complete sequence of the polymer strand that are empirically evident, but not in every case already predictable. This includes for example the synthesis of several G building blocks in succession.

These deviations in the availability or kinetics of individual fragments for the assembly of 2 or more fragments into a target sequence can also be influenced by controlling or controlling and regulating the quantitative proportions. The deviation may be well known and it may be possible to calculate it, or it may only be known empirically and observed in experiments. Accordingly, the method according to the invention can be optimized e.g., iteratively with measurement of the result, for example the yield of target sequence. One embodiment of the invention is the use of a stored-program device, in order to control the predicted optimal composition of the quantitative proportions on the basis of known regularities for new fragment sequences and target sequences. During reaction this can take place by means of a computer or similar control equipment. The influencing factors and settings can be recorded in a database, which in one embodiment is contained in a stored-program device and is used directly or indirectly in the control of the synthesis.

The reaction products of a library synthesis are characterized by considerable variety of the sequences, programming of which is freely selectable during the synthesis operation. A numerical example will illustrate the great variety of such a library. A microarray from the GENIOM® system, for which the nucleic acid molecule populations are synthesized on individual synthesis locations in a special microfluidic support, can for example (status in the year 2006) synthesize up to 60 000 freely selectable oligonucleotides with a sequence of up to 60 nucleotides. The equipment provides spatially-resolved synthesis of the nucleic acids using a projector-based method (see e.g., WO 00/13018 or WO 00/13017).

The aim is to provide nucleic acids with high and rationally programmable diversity of the sequences and controllable quantitative proportions of the individual sequence representatives or fragments (constituents of the library) for subsequent processes in a next step.

Examples of subsequent processes, for which the invention can be used, are:

production of nucleic acid fragments as primers for primer extension methods, strand displacement amplification, polymerase chain reaction, site directed mutagenesis or rolling circle amplification, production of synthetic genes, gene fragments, gene clusters, gene transfers, gene vectors, chromosomes, genomes, optimized genomes, minimal gene clusters, minimal genomes, completely synthetic genomes or of mixtures with directed or randomized variants of synthetic genes, gene fragments, gene clusters, gene transfers, gene vectors, chromosomes, genomes, optimized genomes, minimal gene clusters, minimal genomes, completely synthetic genomes, modulation of gene expression by means of RNAi or antisense methods, in which one more copy of the nucleic acid or nucleic acids produced can be provided by an RNA polymerase, production, extraction, purification, isolation or preparation of analytes (sample preparation) for the logically subordinate analysis by microarrays, by sequencing methods, by parallel sequencing methods, by amplification methods (strand displacement amplification, polymerase chain reaction or rolling circle amplification) or analysis in gel electrophoresis, RNA libraries with e.g., 2 or more sequences for translation in vitro or in vivo, cloning of the nucleic acids produced alone or in combination with further sequences by means of vectors or plasmids, production of minimal genomes, optimized genomes, reduced genomes, mixed genomes of various species, wherein the whole planned stock of the genome or a portion thereof can be encoded by the synthetic nucleic acids, production of target organisms with permanently or temporarily integrated, transformed, transfected or otherwise inserted synthetic genes, gene fragments, gene clusters, gene transfers, gene vectors, chromosomes, genomes, optimized genomes, minimal gene clusters, minimal genomes, completely synthetic genomes or of mixtures with directed or randomized variants of synthetic genes, gene fragments, gene clusters, gene transfers, gene vectors, chromosomes, genomes, optimized genomes, minimal gene clusters, minimal genomes, completely synthetic genomes, production of the target organisms described in the preceding item for the improvement, change or reduction of a native substance occurring in the target organism, e.g., an amino acid chain, a protein, an organic substance, a hydrocarbon, a drug or a precursor thereof, a nucleic acid, a pheromone, or some other substance for the provision of an article used by humans or for production of a substance that is then put to further use, ligation of the nucleic acids in vectors, YACs, BACs, chromosomes or plasmids, validation or testing of hybridization assays and associated reagents and kits by means of the nucleic acid polymers produced, in the areas of microarrays, biochips, dot blots, Southern or Northern blots, bead arrays, serial analysis of gene expression (SAGE), PCR, real-time PCR, reference or calibration methods or steps within assays from the areas of microarrays, dot blots, Southern or Northern blots, bead arrays, serial analysis of gene expression (SAGE), PCR, real-time PCR, production of binding agents such as aptamers and ribozymes and indirect production via the translation in vivo or in vitro of peptides, proteins, antibodies, antibody fragments, peptides acting analogously to antibodies, proteins acting analogously to antibodies, production, via translation in vivo or in vitro of glycoproteins, proteoglycans or complexes with optionally peptide fraction, protein fraction, RNA fraction or DNA fraction, such as ribosomes or proteasomes.

Preferably, in the methods according to the invention, the synthetic nucleic acids are prepared by synthesizing a multiplicity of different nucleic acid fragments at various positions of a common solid support. Preferably the synthesis of the nucleic acid fragments comprises construction from nucleotide building blocks by wet-chemical and/or photochemical methods on the support, subsequent detachment of the nucleic acid fragments and assembling of the fragments to the desired nucleic acid double strand. Furthermore, the synthesis can include amplification steps, in which the synthesized nucleic acid fragments or/and optionally double-stranded intermediates formed from them are submitted to amplification, e.g., PCR. For this purpose, nucleotide building blocks and an enzyme that brings about amplification can be added. Amplifications can take place on the support, i.e., before or/and after detaching the nucleic acid fragments, or/and after elution from the support.

The support can be selected from flat supports, porous supports, reaction supports with electrodes, reaction supports with particles or beads, microfluidic reaction supports, which optionally have surface modifications such as gels, linkers, spacers, polymers, amorphous layers or/and 3D matrices, and combinations of the aforesaid supports. Preferably the support is a microfluidic support.

The nucleic acid fragments are preferably produced by spatially or/and time-resolved in situ synthesis on the support, for example by spatially or/and time-resolved illumination by a programmable light source matrix.

The spatially or/and time-resolved synthesis can take place in a microfluidic support with one or more fluidic reaction spaces and one or more reaction regions within a fluidic reaction space.

Different amounts of nucleic acid fragment species used for assembly can be produced by using several regions and/or larger regions for the synthesis of the particular nucleic acid fragments on the support. An appropriately modified support is also an object of the invention.

The assembly of nucleic acid fragments to nucleic acid double strands may be carried out in several steps. In a first step, the nucleic acid fragments synthesized on the support are provided at the 5'- or/and 3'-end with one or more generic primer sequences of preferably 10-20 or 10-100 bases, especially preferably of 10-30 bases, even more preferably about 15 bases, with the primer sequences being selected so that amplification is possible directly for the individual fragment, for a proportion of all fragments in a mixture, for all fragments in a mixture or after hybridization of two or more nucleic acid fragments with partial complementary sequence. After cleaving off the nucleic acid fragments provided with primers from the support and optionally after elution from the support and optionally a hybridization of fragment pairs with complementary sequence, a subsequent amplification takes place, e.g., by PCR, by adding corresponding primers. In the amplification reaction there is formation of nucleic acid fragments that contain the generic primer sequence at their ends. After cleaving-off the primer sequence, e.g., by means of restriction endonucleases, the resultant nucleic acid fragments can be submitted to further amplification cycles, in order to produce a nucleic acid double strand.

In one embodiment, the nucleic acid double strand produced by synthesis of fragments and their subsequent assembly is inserted into a vector, e.g., a plasmid, and transferred into a suitable host cell, e.g., a bacterial cell.

The preparation of the nucleic acid polymers offers, at several points of the method, the possibility of introducing modifications or labeling into the reaction products by known methods. This includes labeled nucleotides, which are modified e.g., with haptens or optical markers, such as fluorophores and luminescence markers, labeled primers or nucleic acid analogues with special properties, such as special melting point or accessibility for enzymes. Embodiments of the invention can therefore include the following functions and methods and can make the associated laboratory processes possible:

labeling of the oligonucleotides, of the fragments, of covalently or noncovalently bound hybrid strands constructed therefrom and of the target sequences, for direct or indirect detection with a measuring instrument, e.g., an optical, magnetic, electric or chemiluminescent measuring instrument or method of measurement, labeling of the oligonucleotides, of the fragments, of covalently or noncovalently bound hybrid strands constructed therefrom and of the target sequences, for direct or indirect detection by other molecular structures such as enzymes, receptors, proteins, isolation or extraction of the oligonucleotides, of the fragments, of covalently or noncovalently bound hybrid strands constructed therefrom and of the target sequences, binding of the oligonucleotides, of the fragments, of covalently or noncovalently bound hybrid strands constructed therefrom and of the target sequences by the haptens or other building blocks that can be used in a molecular recognition reaction, of a functional group or of a modification, detection of the oligonucleotides, of the fragments, of covalently or noncovalently bound hybrid strands constructed therefrom and of the target sequences, decomposition, selective separation, opening, degradation or enzymatic digestion of the oligonucleotides, of the fragments, of covalently or noncovalently bound hybrid strands constructed therefrom and of the target sequences, attachment of the oligonucleotides, of the fragments, of covalently or noncovalently bound hybrid strands constructed therefrom and of the target sequences to a target structure or to target structures, e.g., in or on a reaction support, on a glass slide, in a reaction vessel, to a target organelle, to a target cell, to a target organ, to an organism, to a surface, to a biological surface, to a molecular complex such as a chromosome, virus particle or protein complex.

An example of application of the invention and the course of the method using the GENIOM® platform are presented below:

1. Design of a microarray from 6000 different 30-40mer, in particular 30mer or 40mer nucleic acid fragments in the GENIOM® equipment. In designing the microarray, the number of synthesis spots per sequence is chosen between 1 and 100 (in single steps), with nucleic acid fragments (oligos) with tested or predicted weaker binding relative to other sequences that participate in assembly later, being represented with a number of synthesis spots that is preferably greater by 50% or more, than at least one other oligo-sequence, in order to increase the percentage in the mixture and thus promote the corresponding hybrids versus the other, stronger-binding sequences.
2. Adding-on of a generic primer-sequence of 10-15, in particular 10 or 15 bases to all 6000 oligos, in particular at both ends in each case, so that all sequences comprise e.g., 60 bases. The primer sequence can be selected so that a PCR reaction is possible by hybridization of in each case two oligos with complementary sequence.
3. Production of the microarray based on the design from 1. and 2. by synthesis in the GENIOM® equipment.
4. Cleaving-off and elution of the oligos from the reaction support.
5. PCR of the library with addition of a primer pair suitable for the primer sequences added in 2. In the PCR there is formation of e.g., 60mers, each of which can carry an insert of e.g., 40 bases with optional sequence and uniform sequences at both ends.
6. Cleaving-off of the primer sequence.
7. Incubation of the resultant 30-40mer library or of the 30mer or 40mer library with new PCR reagents with addition of a primer pair, which e.g., only binds to sequences in the hybrid that are at least 2 fragments apart and therefore leads to a "nested PCR" of a longer fragment (direct assembly and PCR amplification of a synthetic gene is known by a person skilled in the art from publications).
8. Further processing or storage of the resultant amplification product (amplicon). In one embodiment the amplicon is cloned in bacteria using a plasmid and after growth of clones a number of 10 clones or 10 inserts in the clones is sequenced. The sequence-tested synthetic gene is ready.

It is known in the prior art that the use of different quantitative proportions of the individual oligonucleotides for assembly of synthetic genes increases the rate of correct sequences (Gao, X et al., Nucleic Acids Research, 2003, Vol 31; No. 22; p. 143). The stoichiometry of the oligonucleotides has an influence on the thermodynamic parameters on the basis of the law of mass action.

In the preferred embodiment and in a number of the methods described at the beginning for the production of microarrays in situ, the design, i.e., the actual loading and allocation of area and location on the reaction support for an individual oligonucleotide species, can be selected flexibly and hence also the quantity of the individual oligonucleotides. Basically this is possible with all the in situ methods of synthesis known by a person skilled in the art and enumerated at the beginning. Methods that can be programmed flexibly and do not require any change of physical parts in the production setup are particularly preferred for the embodiments of the invention. For example, the ink-jet spotting methods, the projection methods and the Combimatrix electrochemical method are particularly advantageous.

The quantity of individual oligonucleotides is correspondingly, after detachment and elution of the oligos, also controllable in the pool for various oligo-species in solution. When using projection technology for synthesis on the reaction support, the quantitative distribution can be set via the number of micromirrors or projection elements (illumination pixels). A person skilled in the art can see from this example that also analogously to other methods, the design determines the quantities. For example, in a photolithographic method the quantity is determined by the area of the synthesis locations, and in an indirect method based on the use of photo-acids it is determined by the number of physically separated reaction locations that are used for a sequence.

The quantitative proportions can be set and controlled by the user or by software. With suitable software it is possible to program predetermined values for setting the quantitative proportions. In this way the process can be automated in certain places. The inputs can be derived from theoretical models, bioinformatics, sequence comparison, empirical data or information in databases.

For empirical determination and for finding the optimal number of synthesis units per sequence, in a preferred embodiment with micromirrors in a projection unit, a hybridization reaction can be used on a microarray. For this, the selected oligos in solution are hybridized on a microarray that contains sequences that are provided for assembly as complementary counterparts on the respective, corresponding oligos. This analysis simulates the assembly reaction. The result can, in one embodiment, be determined with fluorescence markers, which are secured directly or indirectly to the oligos in solution. The signals from individual analysis spots can then be evaluated relative to one another or quantified. As a result of this analysis, the quantitative proportions can be adjusted by altering the synthesis design.

Adjustment of the quantitative proportions improves the binding conditions for oligos with increased amount in the mixture, and inherently comparatively lower binding strengths are compensated. The probability of correct incorporation in the full set of oligos that take part in the reaction is equilibrated for all oligos.

A comparatively lower binding strength of an oligo with a suitable sequence on a second oligo can be caused, apart from other parameters, by the base composition, mainly by the AT fraction (if only natural bases are used), by the tendency to secondary structures or by further interactions with other oligos in the mixture.

In one embodiment, the amplification of the oligonucleotides that are detached is a component part of the method.

The oligonucleotides or a portion thereof can be synthesized with generic 5'- and/or 3'-sequences, added onto the sequence of the nucleic acid that is to be prepared, so that an amplification of the oligonucleotides or of a portion thereof can then take place. The amplification or primer sequences are complementary to corresponding amplification primers and can contain one or more cleavage sites, preferably Type II cleavage sites. These cleavage sites enable splitting-off of the primer sequences after amplification, e.g., by PCR. Several pairs of amplification primer sequences can be used on one support, to permit a multiplex amplification, e.g., PCR, in an oligonucleotide library. This means that subpopulations of the oligonucleotide fragments can contain specific, but different amplification sequences or pairs of amplification sequences. The amplicons can be purified or can be used directly for the amplification reaction, e.g., for PCR.

In this embodiment, the method can be used for selective amplification of a subpopulation of the sequences derived from the support. It also becomes possible to complete nucleic acid fragments that were not in full-length form after the synthesis. The amplifications can take place directly in the microchannels of the support or/and separately from the support in a suitable reaction vessel. In this way the quantity of nucleic acid fragments available for gene synthesis can be increased significantly. Furthermore, the shortened fragments that formed during the synthesis, and that may hamper the assembly reaction, are diluted and are present at negligible concentrations compared with the amplified full-length fragments. Therefore increasing the proportion of full-length fragments in a mixture intended for gene synthesis by prior amplification and hence dilution of shortened synthesis products can also be a component part of this embodiment.

In yet another—optionally independent—embodiment, nucleic acid fragments with the desired correct sequence can be isolated from a mixture of nucleic acids. For this it is possible for example to use known techniques, such as emulsion-based PCR or individual molecular arrays, in which clonal molecular populations or individual molecules can be isolated and sequenced from a mixture of DNA fragments. By using such techniques during the gene synthesis method, the assembled gene can be "monoclonalized" and each of the individual fragments can be sequenced separately. After sequence verification, the fragment with the desired sequence can be identified, isolated and processed further, e.g., by cloning, DNA based assays, in vitro protein expression etc. The mixture of DNA fragments can be a PCR product, a ligation product or an oligonucleotide library.

Methods in which an emulsion-based PCR simultaneously still contains preferably in each case a bead or particle in the micelles or aqueous compartments, are known by a person skilled in the art. In variants that are particularly optimized and are preferred for the invention, these are smaller than 1 mm in diameter. For example, the method of the company 454, which permits the sequencing of segments in the range 200 to 300 bases (as at 2006), is known. In this, DNA is fragmented into smaller segments and these are then supplemented with uniform linker or adapter sequences by ligation. This mixture is incubated with the beads described in an emulsion PCR. The primers for the PCR reaction are present as solid phase on the beads. The reaction result is a multiplicity of beads, each of which carries clonally only one fragment from the previously fragmented DNA material covalently on the surface. In the next step the beads are immobilized in a reaction support, which contains cavities suitable for the beads and their size, and then detects the sequences on each of the beads in parallel by a so-called sequencing by synthesis reaction that is known by a person skilled in the art.

In the methods according to the invention or in an optionally independent embodiment, first one or more assembly reactions can be combined from the oligos from the parallel synthesis. In one embodiment using emulsion-bead-PCR, the target sequences are to be selected according to the reading widths of the sequencing reaction and are therefore preferably 10 to 1000 nucleotides long, especially preferably 40 to 500. The advantage of this embodiment is that a mixture of assembled sequences, each built up from 2 or more oligos and possibly containing defects, is, in the method presented above, amplified on the beads to clonal populations and these are then sequenced. Therefore, in a preferred embodiment, cloning and quality control of the target sequences can be combined in one step. Localization is effected by immobilization in the support during sequencing. Those DNA target sequences with sequences that meet a predefined criterion can be removed in a next step. In a further preferred embodiment, labeling is carried out by spatially-resolved addition of a marker, e.g., a specifically or nonspecifically binding optical marker, such as an intercalator (Sybergreen).

An optionally independent embodiment comprises a method of in particular parallel sequencing of at least one nucleic acid in a mixture comprising assembled nucleic acids, which possibly contain defective nucleotides, comprising the steps:
(a) amplification of a mixture comprising assembled nucleic acids, which are in each case built up from 2 or more nucleic acid fragments, to clonal populations,
(b) sequencing of at least one clonal population from step (a) and
(c) optionally isolation of at least one nucleic acid, which contains defects, or/and at least one nucleic acid, which is correct.

In a preferred embodiment isolation takes place by isolation of one or more beads. In an alternative embodiment isolation takes place by selective amplification by spatially-resolved addition of PCR reagents. In an alternative embodiment labeling takes place by spatially-resolved addition of a marker, e.g., a specifically or nonspecifically binding optical marker, such as an intercalator (Sybergreen), and subsequent elution by the laser capture method, which is known by a person skilled in the art from the isolation of individual cells.

Clones (beads) that are undesirable or are recognized as defective can be eliminated physically. In one embodiment this can take place by selective treatment with a strong light source such as a laser. Alternatively a further immobilization or derivatization can be carried out, e.g., in a light-dependent reaction, e.g., crosslinking, covalent modification or the adding-on of a molecule that facilitates extraction or elimination. Thus, beads with an undesirable sequence can be selectively excluded during further exploitation of the sequenced product or the plurality of products.

Having been eluted, isolated or otherwise made available for further steps, the desired target sequences can be used for building up even longer target sequences. They can also be used as a mixture for subsequent process steps.

In one embodiment, all constituents of a genome that are regarded as necessary are produced in this method. In a preferred embodiment these DNA segments are, in a subsequent step, inserted in a target organism, which constructs an assembled genome from them in vivo. An especially preferred target organism is *Deinococcus radiodurans* (also known as *Micrococcus radiodurans*), which can assemble its own genome in vivo after fragmentation, e.g., ionizing radiation, into fragments smaller than 10 000 bases.

The beads can be isolated or stored in the sequencing reaction support and used again at a later time.

The clonal sequences can be obtained by detachment or copying without disrupting the covalent linkage to the bead. With copying without disrupting the covalent linkage to the bead, a bead is available later for the clonal sequences to be obtained again.

Parallel sequencing methods like those described above are suitable for the verification of mixtures of oligonucleotides, as described as part of the invention and as starting material for gene synthesis. In a further—optionally independent—embodiment, the composition of a library of oligos from a parallel synthesis method such as the method according to the invention is verified in a parallel sequencing method with at least 100, preferably with 1000 to 10 000, especially preferably with 10 000 to 100 000 and in particular with 100 000 to 100 million or more parallel sequencing reactions.

A person skilled in the art knows other sequencing methods that can be used in the present invention, for example the preparation of so-called polonies as clonal DNA on a reaction support and subsequent sequencing by "sequencing by synthesis reaction" or by "sequencing by ligation". Products that use these methods are obtainable from, among others, the company Applied Biosystems (ABI, USA) under the name Solid and from the company Solexa/Illumina (USA). A special embodiment with especially sensitive detection is the "true single molecule sequencing" (tSMS) from the company Helicos (USA), which also takes place in parallel and therefore can also be used for the invention.

In combination with the selection of the quantity of synthesis capacity, e.g., illumination pixels, mentioned above, a control or regulating logic system can be used as part of the invention. Because the sequencing methods included here are highly parallel, it is possible to record large amounts of data and therefore provide rational adjustment of synthesis parameters, so as to base the proportion of usable target sequences on defined criteria, e.g., proportion of correct target sequences.

DESCRIPTION OF SPECIFIC EMBODIMENTS

The present invention refers to massively parallel sequencing of nucleic acid molecules and retrieval of single species, which may be bound to a carrier, e.g., a bead. The sorting of sequences/parts/beads may be a further, optionally an independent embodiment. Applications may be DNA synthesis, gene synthesis, or/and generation of variant libraries. Technologies employed may include highly parallel sequencing (NGS). The aspects described below and in the Examples may be combined with other aspects and (optionally independent) embodiments described herein.

The invention provides an improved method for the quality control and the subsequent preparation of DNA fragments in a high throughput approach. Basis for the process is a high parallel sequencing of a large number of DNA fragments (10.000-100.000.000) provided by a technology commonly known as Next Generation sequencing (NGS). The invention will combine the ability to retrieve said DNA fragments from the sequencing support by using mechanical, chemical and/or enzymatic steps with the above mentioned technology for highly parallel sequencing. Fundamental attribute of the invention is the ability to connect of a number of monoclonal DNA fragments to their sequence and the subsequent retrieval of said fragments providing the possibility to separate wanted sequences from unwanted ones for downstream processing.

One aspect is sequencing. In one embodiment of the process the starting material consists in synthetically derived oligonucleotides with a length of 60-200 nucleotides. Primer sequences required for the sequencing process can be incorporated into the oligonucleotides or can be added to them by corresponding enzymatic steps. However, the preferred accomplishment is direct incorporation of priming sites into the starting material during chemical synthesis. This will ensure a higher simplicity of the process and will overcome difficulties due to a bias towards preferred sequences during the mentioned enzymatic steps leading to an underrepresentation of particular species in the mixture.

Another aspect is detachment of DNA from support. The DNA may be detached from the support, as described herein, in particular in the Examples.

Yet another aspect is the downstream process/primer removal. Subsequent use of DNA fragments in an application requires the removal of primer regions used for the sequencing procedure. A preferred embodiment for the removal is the use of Type IIs restriction endonucleases by incorporation of a recognition sequence into the starting material. Another embodiment of the process involves the usage of Uracil DNA glycosylase (UDG) and DNA glycosylase-lyase Endonuclease VIII (USER enzyme, NEBiolabs) for removal of terminal regions.

Yet another aspect is registration of bead positions. During the described process of sequencing a data matrix of sequence positions on the support and corresponding sequences will be generated.

Yet another aspect is DNA synthesis. After the correct parts for producing a gene are identified by NGS, the clonal material can be retrieved from the sequencing flow cells using one of the methods described in the examples below, and enzymatically-amplified prior to assembly with the other correct parts.

Yet another aspect is quality control (QC) variant library production. Proteins with new properties such as activity at high pH, enhanced catalytic activity, affinity, and improved stability at high temperatures, are valuable to the specialty chemicals, life sciences, pharmaceutical, and biofuels industries. Site-saturation mutagenesis, alanine scanning and sequential permutation of a gene encoding an existing enzyme are all systematic methods used to identify the individual positions in a protein where amino acid substitutions could confer desirable properties. Sometimes a single amino acid change is sufficient to achieve the necessary level of protein improvement. Frequently though, hundreds or thousands of possible combinations of amino acid substitutions (known as multi-site mutations, or combinatorial variants) must be built and evaluated in order to achieve the desired magnitude of improvement.

Random mutagenesis and recursive directed molecular evolution approaches are other techniques which have been employed to generate new protein properties. Simple random mutagenesis of genes creates only a tiny fraction of all possible variants, rendering successful screenings unlikely or suboptimal.

Targeted single amino acid substitutions in proteins can be produced easily using, for example, a QuikChange® site-directed mutagenesis kit from Stratagene, or from other suppliers of molecular biology reagents. However, manufacturing hundreds of combinatorial variants with mutations at several positions can be onerous and extremely expensive.

Gene synthesis methods are sometimes used to produce large numbers of combinatorial variants. The common library configurations are cloned, or uncloned, pooled variant libraries, where unqualified parts are assembled to full length in complex pools. It is hoped that such libraries will have sufficient diversity and that a high proportion of clones encode potentially functional variant proteins when the members are finally expressed in the host and screened for activity. Unfortunately, using commercial oligonucleotides with defects and assemblies with amplification bias deteriorates the quality of the libraries. Putative variants can actually be frameshift mutations or somehow otherwise defective. Also, given amplification bias, variant libraries don't necessarily reflect a diversity approaching the theoretical limit calculated from the number of added parts.

In one example, parts would be first sequence-verified, and then only perfect parts would be used to assemble combinatorial variants. The immediate effect would be higher quality libraries. If desired, the assembled combinatorial variants could then be resequenced on a NGS instrument, and unique, sequence-verified members individually amplified after bead retrieval. Thereby, close to 1 million unique sequence-verified combinatorial variants could be retrieved for cloning after two sequencing runs, or alternatively, added directly to a high throughput in vitro transcription/translation reaction for protein expression and assay of activity.

Now with the availability of NGS, the full diversity of binding ligands present in a phage display library can be economically identified by DNA sequencing. The information from early rounds of panning could then be used to produce targeted variant phage display libraries with combinations not present in the original randomized library, and thereby speed the affinity maturation process.

By the method(s) described herein, small, medium or large sized libraries may be screened.

By the methods described herein, sequencing sites may be incorporated directly into oligonucleotides. This helps avoiding an amplification bias, and provides processing simplicity. Optionally, part specific amplification sites may be incorporated, which may reduce cross-contamination.

Yet another aspect is primer removal:
Restriction sites to remove primer regions
USER-enzyme (NEB)
digestion with 3'→'5 proofreading during assembly without primer removal Another aspect are methods for physical retrieval of parts, which may be employed in the methods described herein.

There are several methods which one can envision for the retrieval of correct DNA parts from a substrate or from the enclosure of a Next-Gen Sequencing instrument. Release of DNA from sequencing substrate/bead and DNA recovery, or, bead/substrate retrieval followed by DNA release.

- Aspiration of beads or liquid using micropipettes, drawn glass capillaries, pins, hollow pins, or pins with concave tips.
- Acoustic droplet ejection, e.g., according to Labcyte Echo technology where liquids and/or particles can be guided to a receptacle using focused sound waves.
- Laser catapulting, trapping, tweezers and/or laser-cutting. Typically used for the retrieval of individual cells or microdissected, microscopic specimens. Such commercial systems are available from Zeiss, Molecular Devices, ArryX and Leica. If the DNA is bound to a bead or substrate the DNA can be released after the bead or section of substrate is transported to a collection receptacle.
- Magnetic retrieval. If the DNA molecules of interest were bound to paramagnetic beads, the molecules could be retrieved using a magnet.
- Photo-cleavage—If the DNA molecule were bound to a substrate via a photo-labile linker, the DNA could be cleaved from the surface by shining the appropriate wavelength of light on the bound DNA molecule.
- Addition of dispensing reagents to the beads or substrate using acoustic dispense ejection, piezoelectric dispensing, or spotting.
- Enzymatic or chemical cleavage from beads.
- Copying/amplification of DNA from beads or substrate.
- Denaturation of one DNA strand from the substrate using heat or chemical reagent (DMSO, base, formamide)
    - Heat can be applied with an infrared laser, heating block, hot liquid, or hot air.
- Microfluidic—After release of the desired molecule from the surface, one could flow small volumes of liquid over the surface to a location for convenient collection.
- Electrokinetic or electrophoretic—After release of the desired molecule from the surface, one could use an electrical field to direct the molecule to a location for convenient collection.

One could either release DNA from the beads and then recover DNA from the wells, or, retrieve the bead from the well and then release the DNA from the bead.

Further aspects concerning retrieval methods may be considered in the embodiments of the present invention:
- contact vs. non-contact
- throughput
- specificity: although it is preferred to retrieve a clonal molecule, there may be instances where more than one Clonal molecule is recovered. In which case, one could use specific primers to selectively enzymatically amplify the molecule of interest from a mixture thereby separating it from neighbouring contaminants.
- Reliability: It may be difficult to achieve 100% reliability when attempting retrieval of such minute samples. One way to compensate for unreliable retrieval methods is to attempt retrieval of several identical parts from different locations in the sequencing flow cell. That way, a retrieval method that on average delivered the molecule of interest only 50% of the time could be boosted to 99.9% if ten separate retrieval attempts were made (See Table 1):

TABLE 1

| Number of attempts | Ave. probability of failure | Ave. probability of success |
|---|---|---|
| 1 | 50% | 50% |
| 2 | 25% | 75% |
| 3 | 12.5% | 87.5% |
| 4 | 6.3% | 93.8% |
| 5 | 3.1% | 96.9% |
| 6 | 1.6% | 98.4% |
| 7 | 0.8% | 99.2% |
| 8 | 0.4% | 99.6% |
| 9 | 0.2% | 99.8% |
| 10 | 0.1% | 99.9% |

- accessibility of DNA in the system (closed or open cell?, beads or glassplates or molecules on fiberoptics)
- requirements/specs
- Registration:
- generate position data:
- marks on the sequ. plate
- patterns of empty vs. occupied wells
- dyed beads or marker beads
    - fluorescent, luminescent, colorimatric An aspect of the present invention relates to a method to retrieve clonal sequence verified nucleic acids from a plate, carrier or/and substrate, comprising the steps:
1) Provision of a mixture of nucleic acids
2) Turning the nucleic acid mixture into a clonal library
3) Sequencing the clonal library
4) Retrieval of the sequence-verified nucleic acid molecules
5) Optional: use of the retrieved molecules in continuative steps/procedures
6) Optional: repeating steps 2)-5) at least one time.

Sequence verification may be in vitro sequence verification.

In the following, specific embodiments of the method steps 1 to 6 are described. The method steps 1 to 6 may be independently combined with other embodiments or/and aspects described herein, such as the Examples or/and the Claims.

Ad Step 1) Provision of a Mixture of Nucleic Acids

The source of the nucleic acid that are used within the invention are derived from natural, synthetic or mixtures of natural and synthetic sources; they even can be derived from an exterrestrial source. Examples of a natural source of nucleic acids are—but are not limited to—well defined isolates with know or unknown content from organisms, mixture of organisms, body fluids, soil, water, preserved nucleic acid material (FFPE), tissue, viral or phage material, cultured of uncultured microorganisms—in principle all source that are or natural origins and that contain nucleic acid material could be the source of nucleic acids that could be subjected to the described invention.

Examples of a synthetic sources of nucleic acids are—but are not limited to—oligonucleotide mixtures that are derived from oligonucleotide synthesis. Oligonucleotide synthesis can be performed through a classical approach via columns-based synthesis on a DNA-synthesizer (in 4, -8, 48, 96-, 384-columns or higher format) or in a high parallel fashion on microarrays (e.g., by light-directed synthesis (Affymetrix, febit, LC-Sciences) or ink-jet printing methods (Agilent) of other formats that are suitable for high parallel synthesis of oligonucleotides, e.g., beads (Illumina bead arrays), microtiter plates.

Hereby the term oligonucleotide describes a nucleic acid polymer of length of 1-500 bp, in particular 10-300 bp, very particular 20-250 bp in length, consisting of DNA or RNA or analogs and mixtures thereof.

Examples of mixtures of synthetic and natural nucleic acids are—but are not limited to—nucleic acid fragments of natural origin that have been manipulated in a synthetic way or by synthetic methods or are nucleic acid fragments of synthetic origin that have been manipulated in a natural way or by natural methods.

The nucleic acid source can be derived from one source or several sources. The nature of the nucleic acid mixture can be mixture of fragment of a uniform or non-uniform length or mixtures thereof.

In one embodiment the nucleic acid mixture resembles an imperfect (non-sequence-verified) mixture of fragments dedicated to form a target of choice (e.g., a gene). By performing the invention the mixture is turned into a sequence-verified nucleic acid mixture that can be physically retrieved after sequencing and use for assembly of the target of choice.

Furthermore a primary nucleic acid mixture could be processed by different means before it is subjected to the process of the invention. Examples of the preprocessing of the nucleic acid mixture are—but are not limited to—:

Fragmentation of the nucleic acid mixture in order to receive a uniform distribution of length of the fragment or to shredder the fragment to a shorter length or combinations thereof.

Addition of linker or adapter sequences that are suitable for amplification, binding to supports, in subsequent steps Restriction digestion Selection, enrichment or depletion processes In a further embodiment besides nucleic acids also other polymers (peptides, proteins, carbohydrates) may benefit from the present application when appropriate methods for sequence-verification of peptides, proteins, carbohydrates are available.

Ad Step 2) Turning the Nucleic Acid Mixture into a Clonal Library

In order to subject the nucleic acid fragments to the sequencing reaction these fragments have to made "clonal". Hereby "clonal" is defined in such a way that the previous mixture of nucleic acid fragments is individualized by certain means resulting in physical separation of the individual nucleic acid molecules. This leads to the situation that only one individual nucleic acid molecule or one individual kind of nucleic acid molecules is present at a defined location.

Eventually, but not necessarily, the individualization step to receive clonal nucleic acid fragments is combined with an amplification reaction in a simultaneous step (e.g., emulsion PCR, Megaplex-PCR, bridge-PCR, polonies). The combination of individualization and amplification is implemented within the so-called Second Generation sequencing technologies: Roche/454 (emulsion PCR), ABI/Solid (emulsion PCR), Illumina/Solexa (bridge-PCR).

Third generation sequencing technologies are based on sequencing on the single molecule level therefore the individualization step is not combined with an amplification step. Hence with the present invention the individualization—production of clonal nucleic acid molecules—is not combined with amplification when a Third generation sequencing technology is used within the course of the method.

Example of means for individualization of nucleic acid molecule are—but are not limited—

Emulsion PCR

Amplification reaction is performed in water-in-oil emulsion in the presence of low concentration of library molecules and paramagnetic particles coated by one PCR primer. This PCR primer is also present in the solution but in low concentration: it is enough for early cycles of PCR, but then primers on beads should be involved into amplification. Emulsion may be considered as a large number of independent PCR reactions.

Bridge-Amplification

Bridge amplification is a technology that uses primers bound to a solid phase for the extension and amplification of solution phase target nucleic acid sequences. The name refers to the fact that during the annealing step, the extension product from one bound primer forms a bridge to the other bound primer. All amplified products are covalently bound to the surface, and can be detected and quantified without electrophoresis Bridge amplification (two-dimensional PCR)/Illumina Two-dimensional PCR performed is on Cluster station (Flowcell preparation) and on Genome Analyser (regeneration of clusters for Paired-end sequencing). Here is a scheme for Cluster station amplification.

Opposite to conventional PCR surface amplification is performed on constant temperature (60° C.). Formamide works as a denaturing agent. Normally, 35 cycles of pumping:

In contrast to normal PCR all solutions are used only for one cycle and then go to trash. It helps to keep low background. Otherwise occasionally detached DNA molecule could have a chance to hybridize in another place and start a new cluster there. Surface PCR has lower efficiency if compare with PCR in solution. 35 cycles result in ~1000 copies of the original molecule (in ideal PCR 35 cycles should give ~10$^{10}$× amplification). The possible reasons of lower efficiency:

After clonal amplification clusters should be converted into single-stranded form and prepared for sequencing.

Mega-plex PCR

MegaPlex PCR is a robust technology for highly multiplexed amplification of specific DNA sequences. It uses target-specific pairs of PCR primers that are physically separated by surface immobilization. Initial surface-based amplification cycles are then coupled to efficient solution-phase PCR using one common primer pair. We demonstrate this method by co-amplifying and genotyping 75 unselected human single-nucleotide polymorphism (SNP) loci (Nature Methods—4, 835-837 (2007); MegaPlex PCR: a strategy for multiplex amplification; Linda Stromqvist Meuzelaar, Owen Lancaster, J Paul Pasche, Guido Kopal & Anthony J Brookes).

Polonies

Polony: A tiny colony of DNA, about one micron in diameter. The word "polony" is a contraction of "polymerase colony." To create polonies, a solution containing dispersed DNA fragments is poured onto a microscope slide. An enzyme called DNA polymerase is added. It causes each fragment to copy itself repeatedly, creating millions of polonies, each dot containing only copies of the original fragment of DNA. The polonies are then exposed to a series of chemically-labeled DNA base probes that are fluorescent and light up when run through a scanning machine, identifying each nucleotide base in the DNA fragment. In addition to its application to DNA sequencing, polony technology can be used to study the transcriptome (RNA content) of cells and to determine differences in genome sequence between different individuals.

Polony is a contraction of "polymerase colony," a small colony of DNA.

Polonies are discrete clonal amplifications of a single DNA molecule, grown in a gel matrix. This approach greatly improves the signal-to-noise ratio. Polonies can be generated using several techniques that include solid-phase PCR in polyacrylamide gels. However, other earlier patented technologies, such as that from Manteia (acquired by Solexa), which generate DNA on a solid phase surface by bridge amplification—are generally referred to as "Clusters". The terminology and distinction between 'polony' and 'cluster' have become confused recently. Growth of clonal copies of DNA on bead surfaces remains to be generically named although some also seek to name this technique as a "polony" method. The concept of localizing and analyzing regions (clusters or colonies) containing clonal nucleic acid populations was first described in patents by Brown, et. al. (assigned to Genomic Nanosystems).

In one conceptually simple way to create clusters, a solution containing DNA fragments is poured onto a microscope slide dilute enough so that individual molecules are separated. DNA polymerase is added, which copies each fragment repeatedly, creating millions of clusters, each of which contains only copies of the original fragment of DNA. These "clusters" are then used for various kinds of DNA research like DNA sequencing (Polony technology guide; WO 00/18957; Adessi C, Matton G, Ayala G, Turcatti G, Mermod J-J, Mayer P, Kawashima E. Solid phase DNA amplification: characterisation of primer attachment and amplification mechanisms. Nucleic Acids Res. (2000) 28:e87/1-e87/8; Fan Jb, Chee, M S, Gunderson, K L (2006) Highly parallel genomic assays. Nature Reviews of Genetics (8):632-44; Shendure, Porreca et al. Accurate multiplex polony sequencing of an evolved bacterial genome; Zhang et al. Sequencing genomes from single cells by polymerase cloning).

Rolling Circle Amplification

Rolling circle amplification: cp29 DNA polymerase is capable to make up to 103 single-stranded copies of original circle molecule. The multiplication number is significantly different for different templates. So, it is necessary to select only large molecules for sequencing.

The clonal nucleic acid molecules are presented on solid support carriers. Examples for these carriers are—but are not limited to—: glass slides, gels, polymers, capillaries, microfluidic carriers, membranes, porous carriers (e.g., pamgene), plastics, silicon, silicon ordered or chaotic pores, sponge structures, emulsions, cubes, 2D and 3D, dendrimers, beads, particles, resins, metals, nano-particles and nano-structures Special arrangements are Beads within microtiter-, nanotiter-, picotiter plates; these kind of carriers are implemented within the Roche/454 or the ABI-/Solid sequencing systems
  Microfluidic flow cell (Illumina flow cell; carrier implemented within the Illumina sequencing systems)
  Polonator beads (carrier implemented within the Polonator sequencing system from Danahermotion;
  Nanopores (principle implemented within the Pacific Biosystems or Oxford Nanopore sequencing system and Step 3) Sequencing the clonal library The sequencing can be carried out by any sequencing technology that is capable to deduct the sequence information from the individualized/clonal nucleic acid molecules. This can be either on the level of sequencing a clonal library of individual kinds (more than one molecule of each kind; derived by a clonal amplification scheme) of nucleic acid molecules (example of technologies: ABI/Solid, Illumina/Solexa, Roche/454, DanaherMotion/Polonator, Georg Church/Polonator) or on the single molecule level where only one molecule of each kind is presented (example of technologies like: Helicos, Pacific Biosystems, Oxford Nanopores)

Result of the sequencing step is that for each individual molecule of the presented clonal mixture of nucleic acid molecules the sequence and the location is known.

Ad Step 4): Retrieval of the Sequence-Verified Nucleic Acid Molecules

Based on the facts that on a defined position on the carrier only one individual nucleic acid molecule or one individual kind of nucleic acid molecules are present and for these molecules or kind of molecules as well the sequence information and the physical position is available, the present invention discloses various means for physical retrieval/recovery/extraction of these molecules.

Furthermore, various apparatus for physical retrieval/recovery/extraction of these molecules are disclosed.

The methods for retrieval can be grouped by:

Physical Retrieval/Extraction

Non-destructive methods

Destructive methods

With these methods the nucleic acid molecules or part of the carrier with the bound nucleic acid molecules are physically removed from/out of the reaction carrier.

Reagent Application (and Subsequent Physical Retrieval/Extraction)

With these methods the nucleic acid molecules are in a first step contacted with a reagent, followed by a biochemical reaction and then a physical retrieval/extraction method (as described above) is employed to harvest the nucleic acid molecules.

Physical Retrieval/Extraction and Non-Destructive Methods

These methods include the spearing/spiking of the molecules or parts of the carrier with molecules of choice on by use of thin wires, surgical needles, polymer fibres, carbon, glass, nozzles or black silicon.

Alternative methods include pipetting, micro grabbing, laser dissection techniques, ultrasonic techniques (e.g., Labcyte), freezing with cold needles, dielectrophoresis with high frequency, copying to polymer beads, copying by application of glues, adhesive films and gels (may be combined with top-down centrifugation), adhesive pipettes, dry extraction or floating up by use of a CsCl solution.

Alternative methods include spotting and sucking from a plate.

On the single molecule level atomic force microscopy is an appropriate method to harvest the nucleic acid molecules of choice.

Physical Retrieval/Extraction and Destructive Methods

These methods include destructive methods where the carrier is destroyed in a controlled manner before the nucleic acid molecules are harvested. The methods employed include casting, drilling, stamping. Hereby the carrier is fragmented into pieces. Within this process the link of the part of the carrier and the sequence information is maintained.

Further embodiments include precision cutting (e.g., with laser) and dicing of the carrier in a controlled manner Reagent Application Methods In order to harvest the clonal nucleic acid molecules a polymerase (e.g., Klenow) is added to copy-off the sequence that is presented on the carrier after sequencing. This results of a copy of the presented nucleic acid fragment that can be retrieved by one of the physical retrieval/extraction methods described above.

In one embodiment the copying-off-process of the carrier-bound nucleic acid sequence can be combined with an amplification reaction. For this combination the in the art will select for the proper reaction conditions and polymerase enzyme.

In a special embodiment besides adding a polymerase and the required biochemicals also primer molecules maybe added for copying-off or copying and amplifying the carrier-bound nucleic acid molecules. In embodiment an isothermal helicase-dependent amplification scheme is implemented.

In another embodiment the nucleic acid molecules are cleaved from the reaction carrier. This can be performed by adding an enzyme or a chemical.

By application of enzyme the connection between the carrier and the nucleic acid molecules is cleaved and the released molecules are retrieved by one of the physical retrieval/extraction methods described above. Examples for enzymes are nucleases or restriction enzymes.

By application of the chemical the connection between the carrier and the nucleic acid molecules is cleaved and the released molecules are retrieved by one of the physical retrieval/extraction methods described above.

In one embodiment not the complete nucleic acid sequence of the carrier-bound molecule is cleaved off but only a fraction thereof. This can be implemented by an enzymatic strategy where an enzyme is reacting with a part of the nucleic acid sequence in a sequence-specific manner (e.g., restriction enzymes). This can be also implemented by an chemical strategy where a chemical is reacting with a part of the nucleic acid sequence in a sequence-specific manner.

In one embodiment the carrier-bound nucleic acid fragments are reacted or modified in a first step before they are contacted with an enzyme or a chemical as described above. As an example the carrier-bound nucleic acid fragments are reacted with a ligase enzyme to add an adapter sequence to the carrier-bound nucleic acid fragments. This adapter-sequence could be employed in a next step to copy-off or amplify the carrier-bound nucleic acid fragments before the released molecules are retrieved by one of the physical retrieval/extraction methods described above.

In another embodiment the linkage of the carrier-bound nucleic acid fragments is implemented in such a way that the application of special reagent of light is used to weaken or to cut the linkage to the carrier in order to enable the retrieval by one of the physical retrieval/extraction methods described above. Examples for labile linkers are light-labile, acid-labile, base-labile linkers that can be cleaved by the application of light (e.g., UV-, IR-, VIS-light from lamps, lasers or other illumination instrumentation), acid or base. Also so-called safety-catch linkers can be implemented, which are cleaved by the consecutive application of 2 reagents in order to cleave the linkage to the carrier.

In another embodiment, when the carrier-bound nucleic acid fragments are presented in a double-stranded form, first the second strand is released by denaturation and the released molecules are retrieved by one of the physical retrieval/extraction methods described above. Method for denaturation are the application of a proper enzyme (e.g., helicases), application of temperature (heating) of application of reagents that destabilize the double-strand (e.g., formamide, DMSO, DMF, urea, ethanol, etc.) or altering the pH-value.

In another embodiment a reagent is added that requires a special activation in order to be reactive and to initiate the release of the carrier-bound nucleic acid fragments. Reagents that are employed here are e.g., enzymes (e.g., polymerases) or nucleotides or primers that are blocked.

Enzymes to be employed may carry a blocking that can be removed by light, base, acid or by temperature application before they are active. E.g., a polymerase enzyme can be activated by light, acid, base, chemicals or temperature to be active in copying-off the sequence of the carrier-bound nucleic acid fragments.

Nucleotides or primers to be employed to copy-off the sequence of the carrier-bound nucleic acid fragments may carry a blocking that can be removed by light, base, chemicals, acid or by temperature application before they are active.

In a preferred embodiment the blocking of an enzyme, nucleotide or primer to be employed is photo-labile. By site/location-specific irradiation then the enzyme, nucleotide or primer can be easily deblocked and turned into an active species in order to location-specifically copy-off the carrier-bound nucleic acid fragments of choice before it is retrieved by one of the physical retrieval/extraction methods described above.

Automation/Instrumentation

For performing the physical retrieval/extraction of the carrier-bound nucleic acid fragments automated instrumentation is well suited, since a link between the physical position of the carrier-bound nucleic acid fragments and the sequence information has to be established and subsequently the fragments need to be physically retrieved.

Therefore robotic instrumentation is implemented. The robotic instrumentation to be implemented include pick-and-place robots, robots with up to 5 axes, scara platforms, portal and XYZphi robots and spotting instruments.

Examples of manufactures of robotic instrumentation that can be adapted to the present invention are scienion, SPI (Germany), Rohwedder, Tecan, Hamilton, Qiagen, Biorobotics, Cartesian, Jena Analytics, Beckman, B D, Caliper, Zymark, Gesim, Perkin Elmer, Velocity 11, Agilent.

During physical retrieval/extraction of the carrier-bound nucleic acid fragments the alignment and the quality control at various stages of the process is controlled by use of CCD-Cameras, microscopic equipment or photomultipliers.

Ad Step 5) Optional: Use of the Retrieved Molecules in Continuative Steps/Procedure The advantage of the present invention is to be seen in a method for efficient and cost-effective production of sequence-verified nucleic acid fragments. Sequence-verified nucleic acid fragments are the basis for a broad spectrum of applications.

Examples are:

Production of so-called "perfect parts" (the sequence-verified nucleic acid fragments themselves)
 a perfect part is a nucleic acid available for an application
 with a known sequence o Creation of repositories of so-called bio-bricks that resemble generic building blocks for molecular or synthetic biology or biotechnology applications or genetic engineering. These biobricks can be stored away e.g., in microtiter format or any other suitable format and are ready-to-use on demand Production of bead-arrays by cost-effective production of large variety of short to long sequence-verified nucleic acid fragments. The produced fragments are reformatted in such a way that they are affixed to beads. In one embodiment an amplification reaction is carried out before the fragments are affixed to beads Production of microarrays by cost-effective production of large variety of short to long sequence-verified nucleic acid fragments. The produced fragments are spotted onto a support to form a microarray Production of sequence-verified nucleic acid nucleic acid libraries. These libraries could be incorporated in various applications, e.g.:
  Libraries of small to long nucleic acids to form an enrichment matrix (to be spotted on a support or in solution) for enrichment of defined genomic loci of choice (sequence-capture methods, febit: Hybselect, genome-partitioning); by split and combine strategy a high number libraries can be derived from a low number of "megacloner" runs
  Libraries for carrying our multiplex-PCR reactions; by a split and combine strategy different library mixes can be generated and so the best working mixture determined
  Libraries for production of biochips/microarrays by enzymatic elongation with the library being the template Ware-housing of "perfect parts"
  The retrieved nucleic acid fragments can be reformatted (e.g., into microtiter plates), combined with other fragments and stored away. Masterplates can be copied for a continues production of nucleic acid fragments Production of synthetic genes of other high-values nucleic acid fragments
  The perfect parts are refined to synthetic genes or other synthetic biology structures of higher scientific or commercial value. Due to the guaranteed sequence information the refinement processes (e.g., assembly of genes) can be carried out efficiently and cost-effective (which is a real bottleneck, when nucleic acid fragments are implemented that are not 100% sequence-proof)
  The invention can be used as a method to optimize assembly parameters by testing out different fragment sets (different nucleic acid fragments mixtures) in order to produce the same target sequence (e.g., gene). This include also the optimization of the most robust protocol and parameters. This includes also computer logic or method to determine ideal mix of natural and synthetic DNA to produce a desired target product
  The derived sequence-verified nucleic acid fragments can be directly subjected to an assembly within an organism of choice (e.g., *Micrococcus radiodurans*) that will carry out the assembly reaction.
  Alternatively the sequence-verified nucleic acid fragments are first reformatted and the subjected to the organism of choice for in vivo assembly One workflow would be
  Production of sequence-verified nucleic acid fragments for a final product (high-values, size between 100 bases to 1 Gigabase)
  Assembly of the derived fragments (in vivo or in vitro)
  Cloning
  Sequence verification of the final product
  Final product
  Creation of biobanks
  Production of reference samples, standards, calibration standards, defined input material for Next Generation Sequencing, diagnostic applications, biochips, PCR platforms, bead platforms Ad Step 6) Optional: Repeating Steps 2)-5)

In one embodiment steps 2-5 are repeated. In order to produce sequence-verified nucleic acid fragments of large size is of advantage to start off with clonal library of smaller size. This imperfect, non-sequence-verified nucleic acid fragments are sequence-verified within the first round of carrying out steps 2)-5). Afterwards a sub-population of the sequence-verified nucleic acid fragments is used to form larger nucleic acid fragments by an assembly process. As this process step is error-prone and therefore produces sequence variants that are unwanted, a second round of steps 2)-5) is carried out, resulting in sequence-verified nucleic acid fragments of a larger length. By additional selection of the proper nucleic acid fragments, assembly and performing the invention, really large sequence-verified nucleic acid fragments can be generated.

Two specific embodiments of the method to retrieve clonal sequence verified nucleic acids as described herein are preparative next generation sequencing as described in the Examples. The features of these embodiments, the features of Steps 1 to 6 as described herein, and the subject matter of the claims may be combined independently with each other.

In another embodiment of the present invention the sequence-verified nucleic acid molecules are employed to form larger nucleic acid molecules (e.g., genes, chromosomes, genetic functional elements or fragments thereof). This is typically achieved by assembling the sequence-verified nucleic acid compounds which can be obtained either in a single-stranded or double-stranded form e.g., by a polymerase-driven or a ligase-driven process. (e.g., an assembly-PCR). As this process is prone to produce errors in the newly formed larger nucleic acid molecules, the resulting mixture of nucleic acids after the assembly has to be sequence-verified again. This is can be done by following the described process for another time.

A method for production of nucleic acid molecules comprising the steps:
  provision of a mixture of nucleic acids
  turning the nucleic acid mixture into a clonal library,
  sequencing the clonal library,
  retrieval of the sequence-verified nucleic acid molecules,
  use of the retrieved molecules to form (in an assembly of) larger nucleic acid molecules
  optionally repeating steps b) to e) for at least one time.

In yet another embodiment of the invention it is desired to produce a larger population of sequence-variants of larger nucleic acid molecules (e.g., genes, chromosomes, genetic functional elements or fragments thereof). Therefore on purpose the nucleic acid compounds used for the assembly reaction will produce a plurality of larger nucleic acids molecules. In a next step this complex mixture is subjected to the above described process to physically separate these molecules and assign to each of the members the correct sequence. After retrieval of all these molecules functional testing is carried out e.g., to link the sequence to a function or to find sequence variants with improved properties.

In another embodiment of the present invention is used for the production of defined nucleic acid-based affinity matrices. For this purpose the nucleic acid mixture that is provided was designed to bind to defined parts or regions of a high complex nucleic acid population (e.g., human genomic dna). In dependance of the technique used to provide these nucleic acid molecules (e.g., column synthesis, microarray synthesis, natural sources) more or less sequence errors. The present invention is used to physically individualize all of the members of the mixture and assign a sequence to all. Next, these members that show the right sequence can be retrieved by the disclosed methods and used for enrichment purposes (enrichment, sequence capture, hybselect) downstream.

For cost reduction purposes, the input nucleic acid mixture can be composed of a plurality of nucleic acid mixtures (subpopulations: 1: BRCA1, BRCA2; 2: TP53, KRAS; 3:PIK3A, PTEN, MYC, CDK4), each being designed to form different affinity-matrices for downstream extraction of complex nucleic acid populations (e.g., human genomic DNA). The physical separation upon sequencing and the subsequent retrieval process allows to form the now sequence-verified plurality of nucleic acid mixtures (subpopulations).

An—optionally independent—further embodiment of the invention relates to the production of libraries that contain a multiplicity of variants of a gene, through synthesis of multiple variants of one or more of the nucleic acid fragments on the support before gene assembly.

Yet another—optionally independent—embodiment of the invention relates to the enzymatic cleaving-off of the nucleic acid fragments from the support.

Yet another—optionally independent—embodiment of the invention relates to the purification of a library of nucleic acid fragments through rehybridization on a support that contains the complementary sequences.

Yet another—optionally independent—embodiment of the invention relates to the adding-on of primer-specific DNA sequences to the nucleic acid fragments that form the 5'-end and the 3'-end of the nucleic acid double strand that is to be synthesized. In this way several successive reactions can be carried out with the same primer pair. Moreover, different genes from different supports can be amplified simultaneously with the same primers, whereby the method is automated.

Yet another—optionally independent—embodiment of the invention relates to the production of synthetic target nucleic acids for standard microarray analysis methods, e.g., of probes that are immobilized on standard microarrays.

The aforesaid embodiments can of course be combined with one another.

In general, all reaction supports and solid phases, for which synthesis of a matrix of nucleic acid polymers is possible, can be used for the method according to the invention.

These include, as typical representatives, the following reaction support formats and solid phases that are known by a person skilled in the art:
  flat reaction support, also called "chip",
  porous supports,
  reaction supports with electrodes,
  reaction support with temporarily or permanently immobilized solid phase of particles or beads,
  microfluidic reaction support,
  surface modification: gels, linkers, spacers, polymers, amorphous layers, 3D matrices.

Some of these reaction supports can be used in combination, e.g., a microfluidic reaction support with porous surfaces.

The DNA probes are preferably constructed by light-controlled in situ synthesis on a microfluidic support, e.g., in a GENIOM® one instrument (febit biotech GmbH) using suitable protecting-group chemistry in a three-dimensional microstructure. In a cyclic synthesis process, illuminations and condensations of the nucleotides alternate until the desired DNA sequence has been built up completely in the microchannels at each position of the array. In this way e.g., up to 48 000 oligonucleotides with a length of e.g., up to 60 individual building blocks can be prepared. The oligonucleotides can bind covalently to a spacer molecule, a chemical spacer on the glass surface of the reaction support. Synthesis takes place under software control and permits high flexibility in the construction of the array, which the user can therefore configure individually according to his needs. For example, the length of the oligonucleotides, the number of nucleic acid probes produced or internal controls can be optimized for the particular experiment.

In one embodiment, high-quality nucleic acids with a freely programmable sequence are prepared in the form of oligonucleotides with a length of 10-200 bases, inexpensively and efficiently in a plurality of 10 or more different sequences, in order to produce synthetic coding double-stranded DNA (synthetic genes).

The construction of double-stranded DNA from oligonucleotides has been known since the 1960s (works of Khorana and others; see "Shabarova: Advanced Organic Chemistry of Nucleic Acids", VCH Weinheim). In the majority of cases it is carried out by one of two methods (see Holowachuk et al., PCR Methods and Applications, Cold Spring Harbor Laboratory Press).

In one case synthesis of the complete double strand is carried out by synthesis of single-stranded nucleic acids (of suitable sequence), assembly by hybridization of complementary regions of these single strands and ligation of the molecular backbone by enzymes, generally ligase.

Conversely, there is also the possibility of synthesis of regions that overlap at the edges as single-stranded nucleic acids, assembly by hybridization, filling-up of the single-stranded regions by enzymes (polymerases) and then ligation of the backbone by enzymes, generally ligase.

A preferred course of gene synthesis according to the invention is as follows: generally, within the scope of a modular system, many individual nucleic acid strands are synthesized using the method according to the invention for highly parallel matrix-based DNA synthesis. The reaction products are sets of nucleic acids, which serve as building blocks in a subsequent process. As a result, a sequence matrix is produced that can contain more than 100 000 different sequences. The nucleic acids are in single-stranded form and can be eluted from the support or can be reacted directly in the reaction support. By repeated copying in one or more operations, multiple copies of the matrix can be produced without destroying it, and multiplication of the particular sequences encoded in the matrix is achieved at the same time. As described in more detail elsewhere, by copying from distal to proximal it is also possible to cut down the proportion of shortened nucleic acid polymers on the solid phase, if the copying initiation site is located distally. An example is a distally attached promoter sequence.

The support with the matrix of molecules bound to the solid phase can be stored for later reuse. The plurality of sequences produced in one reaction support by an in situ synthesis can thus be made available for further process steps. At the same time, through the design of the copying reaction, high quality of the copied sequences can be achieved.

Then suitable combinations of the detached DNA strands are formed. Assembly of the single-stranded building blocks to double-stranded building blocks takes place within a reaction space, which in a simple setup can be an ordinary reaction vessel, e.g., a plastic tube. In another preferred embodiment the reaction space is part of the reaction support, which in one variant can be a microfluidic reaction support, in which the necessary reactions take place. A further advantage of an integrated microfluidic reaction support is the possibility of integration of further process steps, such as quality control by optical analysis. In one embodiment the matrix has already been synthesized in a microfluidic support, which can then be used simultaneously as reaction space for the subsequent assembly.

The sequence of the individual building blocks is selected so that on bringing the individual building blocks in contact with one another, complementary regions at the two ends brought together are available to permit specific assembly of DNA strands through hybridization of these regions. This results in longer DNA hybrids. The phosphodiester backbone of the DNA molecule is closed by ligases. If the sequences are selected in such a way that there are single-stranded gaps in these hybrids, these gaps are filled enzymatically by polymerases in a known procedure (e.g., Klenow fragment or Sequenase). This results in longer double-stranded DNA molecules. If further use requires these elongated DNA strands to be available in the form of single strands, this can be achieved by the methods that are known to a person skilled in the art for denaturing DNA double strands, such as temperature or alkali.

By bringing together clusters of DNA strands synthesized in this way within reaction spaces, it is once again possible to produce longer partial sequences of the final DNA molecule. This can be carried out in stages, and the partial sequences are then assembled to longer and longer DNA molecules. In this way it is possible to produce very long DNA sequences as a completely synthetic molecule with a length of more than 100 000 base pairs. This already corresponds to the order of magnitude of a bacterial artificial chromosome (BAC). Construction of a sequence of 100 000 base pairs from overlapping building blocks of 20 nucleotides length requires 10 000 individual building blocks.

This can be accomplished with most of the highly parallel methods of synthesis described at the beginning. Those technologies that produce the array of nucleic acid polymers in a largely freely programmable manner, and do not rely on the setting-up of technical components, such as photolithographic masks, are especially preferred for the method according to the invention. Accordingly, especially preferred embodiments employ projector-based light-based synthesis, indirect projector-based light-controlled synthesis by means of photo-acids and reaction chambers in a microfluidic reaction support, electronically induced synthesis by spatially-resolved deprotection on individual electrodes on the support and fluidic synthesis by spatially-resolved deposition of the activated synthesis monomers.

For the rational processing of genetic molecules and the systematic acquisition of all possible variants, the building blocks must be produced flexibly and economically in their individual sequence. The method accomplishes this through the use of a programmable light source matrix for the light-dependent spatially-resolved in situ synthesis of the DNA strands that are used as building blocks. This flexible synthesis permits the free programming of the individual sequences of the building blocks and hence also the production of any variants of the partial sequences or of the final sequence, without any associated substantial modifications of system components (hardware). Only this programmed synthesis of the building blocks and hence of the final synthesis products can provide systematic processing of the plurality of genetic elements. At the same time, the use of computer-controlled programmable synthesis makes it possible to automate the entire process including communication with corresponding databases.

When the target sequence is specified, the sequence of the individual building blocks can be selected rationally taking into account biochemical and functional parameters. Following input of the target sequence (e.g., from a database) an algorithm searches for the suitable overlapping regions. Depending on the definition of the task, varying numbers of partial sequences can be set up, namely within one reaction support that is to be illuminated or distributed on several reaction supports. The attachment conditions for formation of the hybrids, such as temperature, salt concentration etc., are matched by a corresponding algorithm to the available overlapping regions. This ensures maximal specificity of assembly. The data for the target sequence can, in a fully-automatic version, also be taken directly from public or private databases and converted to corresponding target sequences. The resultant products can, once again optionally, be fed into appropriately automated processes, e.g., into cloning in suitable target cells.

Construction in stages by synthesis of the individual DNA strands in reaction regions within circumscribed reaction spaces also makes it possible to construct difficult sequences, e.g., those with internal repeats of sequence segments, such as are found e.g., in retroviruses and corresponding retroviral vectors. By detaching the building blocks within the fluidic reaction spaces, any sequence can be synthesized, without problems arising from allocation of the overlapping regions on the individual building blocks.

The high quality requirements that are necessary when constructing very long DNA molecules are fulfilled inter alia through the use of real-time quality control. The spatially-resolved synthesis of the building blocks is monitored, as is the detachment and assembly as far as construction of the final sequence. Then all processes take place in a transparent reaction support. It is, moreover, possible to monitor reactions and fluidic processes in transmitted light, e.g., using CCD detection.

The miniaturized reaction support is designed so that a detachment process is possible in the individual reaction spaces, and therefore the DNA strands synthesized on the reaction regions within these reaction spaces are detached in clusters. With suitable design of the reaction support, assembly of the building blocks can take place in stages in reaction spaces, as well as the removal of building blocks, partial sequences or of the final product, or also sorting or separation of the molecules.

Once it is completed as an integrated genetic element, the target sequence can be inserted in cells by transfer and can thus be cloned and can be investigated in the course of functional studies. Another possibility is first to carry out further purification or analysis of the synthesis product, whereas said analysis can for example be sequencing. The sequencing process can also begin by direct coupling with suitable equipment, e.g., with a device operating according to patent application DE 199 24 327 for integrated synthesis and analysis of polymers. It is also conceivable for the target sequences produced to be isolated and analyzed after cloning.

The method according to the invention provides, with the integrated genetic elements that it produces, a tool that encompasses the biological variety in a systematic process for the further development of molecular biology. The production of DNA molecules with desired genetic information is therefore no longer the bottleneck in molecular biological work, because from small plasmids via complex vectors and as far as mini-chromosomes, all molecules can be produced synthetically and made available for further work.

The method of preparation permits the parallel production of numerous nucleic acid molecules and therefore a systematic approach for questions concerning regulatory elements, DNA binding sites for regulators, signal cascades, receptors, action and interactions of growth factors etc.

Through integration of genetic elements in a completely synthetic total nucleic acid, the known genetic tools, such as plasmids and vectors, can continue to be used, building on relevant experience. On the other hand this experience will change rapidly through the endeavours to optimize the existing vectors etc. The mechanisms that for example make a plasmid suitable for propagation in a particular cell type can be investigated rationally for the first time on the basis of the method according to the invention.

Through this rational investigation of large numbers of variants, the entire combination space of genetic elements can be opened up. Along with highly parallel analysis (including on DNA arrays or DNA chips) that is currently undergoing rapid development, the programmed synthesis of integrated genetic elements is created as a second important element. Only both elements together can form the foundation of rational molecular biology.

With the programmed synthesis of corresponding DNA molecules, it is not only possible to have any desired composition of coding sequences and functional elements, but also the regions in-between can be adapted. This should quickly lead to minimal vectors and minimal genomes, once again producing advantages through the smaller size. Transmission vehicles, such as viral vectors, can thus be made more efficiently, e.g., using retroviral or adenoviral vectors.

Beyond the combination of known genetic sequences, the development of new genetic elements is possible, which can build on the function of existing elements. It is precisely for such development work that the flexibility of the system is of enormous value.

The synthetic DNA molecules are fully compatible, at every stage of development of the method described here, with existing recombinant technology. Integrated genetic elements can also be provided for "traditional" molecular biological applications, e.g., by means of appropriate vectors. The incorporation of corresponding cleavage sites even for enzymes that have so far found little application is not a limiting factor for integrated genetic elements.

This method makes it possible to integrate all desired functional elements as "genetic modules", such as genes, parts of genes, regulatory elements, viral packaging signals etc., into the synthesized nucleic acid molecule as carrier of genetic information. This integration offers the following advantages, among others:

High-grade functionally integrated DNA molecules can be developed, omitting unnecessary DNA regions (minimal genes, minimal genomes).

Free combination of the genetic elements and the changes to the sequence, e.g., for adaptation to the expressing organism/cell type (codon usage), are also made possible, as are changes to the sequence for optimizing functional genetic parameters, for example gene regulation.

Changes to the sequence for optimizing functional parameters of the transcript also become possible, e.g., splicing, regulation at the mRNA level, regulation at the translation level, and furthermore the optimization of functional parameters of the gene product, for example the amino acid sequence (e.g., antibodies, growth factors, receptors, channels, pores, transporters etc.).

Furthermore, it is possible to devise constructs that interfere with gene expression by the RNAi mechanism. When such constructs encode more than one RNAi species, several genes can be inhibited simultaneously in a multiplex system.

Overall, the system achieved with the method is extremely flexible and permits, in a manner not previously available, the programmed construction of genetic material at greatly reduced expenditure of time, materials and work.

Directed manipulation of larger DNA molecules, such as chromosomes of several hundred kbp, was practically impossible with the existing methods. In fact, more complex (i.e., larger) viral genomes of more than 30 kbp (e.g., adenoviruses) are difficult to handle and manipulate with the classical methods of genetic engineering.

There is considerable shortening as far as the last stage of cloning of a gene: the gene or genes are synthesized as a DNA molecule and then (after suitable preparation, such as purification etc.) are inserted directly into target cells and the result is investigated. The multistage cloning process, generally taking place via microorganisms such as *E. coli* (e.g., DNA isolation, purification, analysis, recombination, cloning in bacteria, isolation, analysis etc.), is therefore reduced to the last transfer of the DNA molecule into the final effector cells. With synthetically produced genes or gene fragments, clonal multiplication in an intermediate host (generally *E. coli*) is no longer necessary. We thus avoid the risk that the gene product intended for the target cell has a toxic action on the intermediate host. This is a clear contrast from the toxicity of some gene products, which when using classical plasmid vectors often leads to considerable problems in cloning the corresponding nucleic acid fragments.

Another appreciable improvement is the shorter time and the reduction in process steps, until, after sequencing of the genetic material, the resultant potential genes are verified as such and are cloned. Normally after discovering interesting patterns, which may be considered as ORF, corresponding clones are sought with probes (e.g., by PCR) in cDNA libraries, though they need not contain the entire sequence of the messenger RNA (mRNA) used originally in their production (the problem of "full length clones"). In other methods, an antibody is used for searching in an expression gene library (screening). Both methods can be shortened considerably with the method according to the invention: if we have a gene sequence that has been determined "in silico" (i.e., after recognition of a corresponding pattern in a DNA sequence by the computer), or after decoding a protein sequence, a corresponding vector with the sequence or variants thereof can be produced directly via programmed synthesis of an integrated genetic element and inserted in suitable target cells.

The synthesis of DNA molecules in this way up to several 100 kbp permits the direct complete synthesis of viral genomes, e.g., adenoviruses. These are an important tool in basic research (including gene therapy), but because of the size of their genome (approx. 40 kbp) they are difficult to manipulate with classical methods of genetic engineering. In particular this greatly limits the rapid and economical production of variants for optimization. This limitation is removed by the method according to the invention.

With the method, synthesis, detachment of the synthesis products and assembly to a DNA molecule are integrated in one system. With the production methods of microsystem engineering, all necessary functions and process steps up to purification of the final product can be integrated in a miniaturized reaction support. These can comprise synthesis regions, detachment regions (clusters), reaction spaces, feed channels, valves, pumps, concentrators, separation regions etc.

Plasmids and expression vectors can be produced directly for sequenced proteins or corresponding partial sequences and the products analyzed biochemically and functionally, e.g., using suitable regulatory elements. The search for clones in a gene library is therefore omitted. Correspondingly, open reading frames (ORF) from sequencing work (e.g., the human genome project) can be programmed directly in corresponding vectors and combined with desired genetic elements. Identification of clones, e.g., by costly screening of cDNA libraries, is unnecessary. The flow of information from sequence analysis to function analysis is therefore much shorter, because on the same day that an ORF is in the computer from analysis of primary data, a corresponding vector including the presumed gene can be synthesized and made available.

Relative to conventional solid-phase synthesis for obtaining synthetic DNA, the method according to the invention is characterized by lower expenditure of materials. For the production of thousands of different building blocks for the production of a complex integrated genetic element with length of several 100 000 kbp, in correspondingly parallelized format and with corresponding miniaturization (see Examples of application), a microfluidic system uses far less feed material than a conventional automatic machine for solid-phase synthesis for an individual DNA oligomer (when using a single column). Here, microliters are contrasted with the consumption of milliliters, i.e., a factor of 1000.

Taking into account the latest findings in immunology, the method described permits extremely efficient and rapid vaccine design (DNA vaccines).

EXAMPLES

Example 1

Preparative Next Generation Sequencing—High Parallel In Vitro Cloning and Sequencing for Gene Synthesis and Library Preparation Summary The major cost factors of synthetic gene production are oligonucleotides as starting material for gene assembly, and the subsequent screening and selection of correct parts from a mixture of correct and defective gene fragments resulting from errors in oligonucleotide synthesis[1]. While microarrays and especially photo-programmable microfluidic chips[2,3] represent an effective tool to decrease the cost for oligonucleotide production by orders of magnitude[4], the overall production cost for synthetic genes remains high due to the need for cloning and sequencing post-synthesis. Here we describe a proof of concept for a high throughput retrieval of clonal DNA with known sequence from a next generation sequencing (NGS) platform[5]. This technology will reduce efforts for quality control, screening and selection of DNA significantly and could be useful in gene synthesis and for DNA-library handling in different biotechnological applications.

Introduction

The de novo synthesis of genes offers an almost unlimited degree of freedom for the adaptation and generation of sequences. Synthetic gene production is a versatile tool to answer questions derived from the ever-increasing volume of sequence data[6]. Furthermore, it opens new applications in the scope of the emerging field of synthetic biology including generation of genetic circuits[7], gene clusters[8] and artificial genomes[9]. Prices for synthetic genes decreased significantly in the past decade, showing an exponential decline from $12 per basepair in the 1990s[10] to approximately $0.50 in 2009.

De novo gene synthesis can be a fast and economic source for DNA up to a few kilobases in size and is often a convenient alternative to conventional cloning methods. Despite this trend, the price per basepair for de novo gene synthesis still represents a bottleneck for the generation of more sophisticated biological systems in the megabase scale and beyond. Furthermore, the production cost for synthetic DNA made by state of the art technologies are approaching an asymptotic value due to the raw material costs of oligonucleotide synthesis in microcolumns and the limitations of conventional Sanger sequencing. The optimization and automation of these production methods are unlikely to reduce prices by more than a factor four to five. However, future projects on the megabase level, for example the synthesis of artificial bacterial genomes, will require gains in efficiency of at least two orders of magnitude to keep costs to a reasonable level.

After enzymatic assembly of oligonucleotides in an initial step[11] correct parts have to be selected out of the resulting mixture by cloning and sequencing prior to the generation of longer genes by one or several recursive steps of ligation or PCR. The probability of finding an error-free part among a certain number of clones of given length decreases exponentially with an increase of the oligonucleotides' error rate and the assembled gene-length[12,13]. Errors during chemical oligonucleotide synthesis leading to 1-3 errors per kilobase in assembled genes usually requires ~10-15 fully sequenced clones to obtain an error-free 1 kb gene[14,15] representing another financial impediment in gene synthesis beyond the generation of oligonucleotides.

Error reduction schemes for gene synthesis have been developed and practised extensively. Numerous methods are known that can be introduced in different levels of gene synthesis as on the oligonucleotide level[16] or the ready assembled gene[13,15,17]. Although these error reduction techniques enhance throughput and efficiency they do not supersede necessary sequencing for selection and quality control.

To overcome the restrictions associated with the state of the art technology for gene synthesis two issues have to be addressed:

1. The cost of oligonucleotides as building blocks have to be decreased dramatically
2. Technologies for the clonal selection of correct parts have to be scaled-up significantly with simultaneous reduction of costs.

We have devised an approach that overcomes these limitations by combining three technologies: optional synthesis using programmable DNA microarrays; sequencing of oligonucleotides or longer DNA segments using next-generation platforms; and selection of desired sequences by targeted extraction of the sequenced DNA from the arrayed format of the next-generation platform.

Programmable DNA microarrays are a source of inexpensive DNA oligonucleotides for gene synthesis[6,16,18]. They offer the potential for reducing raw material cost for gene synthesis by several orders of magnitude. However, the full potential of microarrays in gene synthesis will only be realized with technologies for sorting the derived oligonucleotide pool containing thousands of species into sub-pools for the assembly of different genes. Otherwise, the cost of clonal sequencing and sorting would outweigh the benefit derived from chip synthesis, especially considering the fact that microarray derived oligonucleotides come with an even higher error rate than conventional ones.

Next generation sequencers enable extremely high throughput sequencing of short DNA fragments using in vitro cloning technologies and a highly parallel readout of sequence data.

The GS FLX system from Roche and 454 Life Sciences[5] generates more than 100 million bases per sequencing run with an average yield of greater than 400.000 reads of 250 bases read length with good accuracy[19]. The sequence data obtained includes the position of the particular bead on the sequencing plate that carries the known clonal DNA sequence. With the possibility to retrieve the bead-bound DNA, the 454 platform could represent a tremendous source of synthetic and natural sequenced-verified DNA where the yield from one picotiter plate is equivalent to that from hundreds of thousands Sanger-sequence runs. A harvest of just 10% correct sequences would yield ~40.000 DNA fragments of 250 bp average length corresponding to 10 Mbp correct DNA.

Using such "perfect parts" in gene synthesis would result in significantly reduced error rates caused by misannealing or polymerase failure which are known to be considerably lower than errors resulting from synthesis failure[12]. Beside the use of error-free fragments in de novo gene synthesis, other applications such as library generation for antibody- or enzyme selection, or screening of cDNA pools would benefit from preparative NGS providing fast access to huge numbers of sequenced-verified DNA fragments.

Results

We successfully recovered sequenced DNA fragments out of a picotiter plate from the GS FLX system and assembled them into functional genes. We generated DNA fragments for the assembly of two genes coding for β-D-Glucuronidase (UidA)[20] (2080 bp) and *Biomphalaria glabrata* hemoglobin BgHb[21] (1861 bp) with codon optimization for expression in *E. coli*. The genes consisted out of 9 and 8 fragments respectively of 235-394 bp in length generated by PCR assembly (FIG. 1A). Terminal sequencing primers for amplicon sequencing on the GS FLX system were added to enable direct sequencing. The primers were removed later by endonuclease cleavage in order to use the parts for assembly of the entire genes. We prepared 8 mixtures containing 2 or 3 gene fragments with equimolar concentrations (Table 2) and applied them in a GS FLX sequencing run on 8 separated areas of a picotiter sequencing plate forgoing the final bleaching step after sequencing.

The extraction of beads was performed under a microscope using a micropipette attached to a manually controlled micromanipulator (see supplemental information). The pipette allowed the establishment of direct contact to the beads inside the wells which was necessary to generate sufficient force to lift the particles out which were held inside the wells by non-covalent interactions mediated by two additional smaller kinds of beads (enzyme- and packing-beads) in order to withstand numerous flushing steps during the sequencing procedure.

After recovery of single beads we amplified the bound DNA by PCR. The amplicons were cloned and Sanger-sequenced subsequently for verification of recovered sequences with the data derived from the NGS-device. To prove the functionality of preparative NGS-derived DNA, we assembled the two genes using the recovered fragments (FIG. 1A). Successful assembly and absence of errors was proven by conventional Sanger sequencing. Additionally, we assayed the functionality of the β-D-Glucuronidase gene by adding X-Glc (5-Bromo-4-chloro-3-indolyl β-D-glucopyranoside) to the culture plates resulting in blue colonies in the presence of a functional gene[22].

Despite the initial adjustment of fragment concentration in the sequencing mixtures for the areas on the plate, we observed unequal counts and clustering of beads for particular gene fragments in certain areas on the plate making it difficult to obtain all the needed parts by random extraction. To minimize the number of beads required to ensure the recovery of every gene fragment, we used a simple approach for registration and localization of beads based on the coordinates reported in the sequence data.

These coordinates correspond to pixels in the raw images of the plate generated during the run. The positions of desired beads were mapped into an enlarged raw image providing an overview of the position of wells containing the beads (FIG. 1C coloured dots). As an initial approach we mapped the positions of desired beads manually into a microscopic image of the corresponding plate fraction by using the patterns emerging from bead-containing and empty wells as reference points for orientation on the plate (FIGS. 1C and 1D white lines).

We tested this method by targeted extraction of beads loaded with DNA sequences necessary for the assembly of the test genes that were correct within the read length of the sequencer (app. 250 bp). We obtained all 17 gene fragments for assembly of the model genes and verified correctness by Sanger sequencing of PCR amplicons. With the described equipment we obtained an extraction success of approximately 50% (extracted beads/obtained amplicons), whereas the main failure mode was the loss of beads during transfer to the PCR tube, and consequently PCR failure.

To further prove targeted retrieval, and to exclude false positive hits we selected and extracted 15 unique parts from the plate to assure an unambiguous identification. The recovered beads were distributed randomly on the plate. The verification was performed by Sanger sequencing of derived PCR products after amplification of bead bound DNA. To assure uniqueness we compared all Sanger derived sequences with all reads from the NGS device. In this context we obtained the expected sequences with only a few discrepancies occurring exclusively at homopolymer stretches and caused very likely by sequencing failure in the GS FLX device.

To ease recovery and to prepare automated extraction procedures we additionally tested an approach for computer aided localization of beads in a microscope image by using a simple algorithm for mapping bead-containing well positions into a microscopic picture of a plate fragment by rotation and linear scaling (FIG. 1D coloured dots and supplemental information). This approach eases the identification of the wells of interest with human intervention. However, it is not yet sufficiently accurate to navigate a robot to the centres of the wells. This is caused by the relative low resolution of the raw image resolving one well with app. 9-10 pixels, causing too much deviation for an exact positioning in the well centre. Probably the non-linearity of spot distances in the two pictures caused by optical distortions of the lenses in the microscope and in the sequencer camera could be problematic. The pattern recognition for orientation on the plate worked well for this manual approach. However, a system providing sufficient numbers of reference points, probably by using coloured or fluorescent beads loaded with defined DNA sequences (which could be located in the sequencer and in the microscopic picture), could turn out to be more suitable reference points for automation.

We showed that a manual extraction of beads is possible for the targeted retrieval of bead-bound DNA from a high throughput sequencer. As expected, the manual identification of wells and bead extraction is a time-consuming and error-prone task and the throughput remains inadequate. To fully exploit this source of DNA, better automation is required. Appropriate microactuators are commercially available and could easily be equipped with the required pipette tools. The bottleneck for automation would be an accurate determination of well positions based on the dataset from the sequencing instrument. A solution could be the combination of the given sequencer's data to approximate the well positions and intelligent software for selecting correct parts only from those wells which are associated with a high level of confidence. The next logical step is to develop an automated bead localization and retrieval system.

We have proven that preparative NGS is feasible with the GS FLX system. But the principle of recovery of sequenced, quality-controlled DNA should be generally transferable to other next generation sequencing platforms. Although advantageous in the field of gene synthesis due to superior read lengths, the 454 platform gives less sequence information compared to other available platforms like Illumina's genome analyzer, the SOLiD system from ABI, or the Polonator from Dover Systems. The higher number of reads from those platforms could be better-suited for screening shorter pools with higher error rates like microarray derived libraries. Due to different platform architectures, partially closed systems and significantly smaller DNA carriers the harvest would additionally require a different toolset such as optical approaches including photo-sensitive and cleavable molecules.

TABLE 2

| Lane | Fragments | Lengths*) | Reads |
|---|---|---|---|
| 1 | UidA-A | 394 | 11668 |
|   | BpHb-H | 235 | 56131 |
| 2 | UidA-B | 394 | 26791 |
|   | BqHb-C | 394 | 33989 |
| 3 | UidA-C | 394 | 56589 |
|   | BgHb-D | 394 | 9249 |
| 4 | UidA-D | 394 | 11464 |
|   | BgHb-E | 394 | 43111 |
| 5 | UidA-E | 394 | 20754 |
|   | BqHb-F | 394 | 41657 |
| 6 | UidA-F | 394 | 24106 |
|   | UidA-G | 394 | 17163 |
|   | BaHb-G | 394 | 17166 |
| 7 | UidA-H | 274 | 17218 |
|   | BqHb-A | 394 | 29991 |
| 8 | UidA-1 | 354 | 28436 |
|   | BgHb-B | 394 | 25886 |

*)incl. sequencing primer 7.1.4 Methods

Prior to extraction of the 28 pm sized beads we stored the picotiter plate under a water layer to prevent desiccation and shrinking. Beads were removed from the wells of the picotiter plate (diameter ~40 μm) under a microscope using a micropipette with an inner diameter of 21 μm as a vacuum grabber. The micropipette (outer diameter 31 μm) was attached to a manually controlled micromanipulator device. After picking, the beads were transferred quickly into buffer to prevent bead shrinking by evaporation which could cause a capillary blockage by suction of the shrunken bead into the capillary channel Amplification of bead bound DNA was performed with the primers "GS-FLX-A" and "GS-FLX-B" (suppl. info). PCR conditions: 20 mM Tris-HCl (pH 8.8), 10 mM ammonium-sulfate, 10 mM potassium chloride, 2 mM magnesium-sulfate, 0.1% Triton X-100, 200 μM each dNTP, 2% (v/v) DMSO, 1 μM each primer, 50 U/ml native Pfu polymerase (Fermentas). Cycling: initial denaturation 96° (2 min); then 30 cycles of 96° (30 s), 63° (30 s), 72° (30 s), and final elongation 72° (3 min).

For removal of primer regions purified amplicons were incubated with Lgul in 1× Tango buffer (Fermentas) for 3 h at 37°. Small restriction fragments (primer regions) were removed by PCR purification columns (GenElute PCR Clean-Up, Sigma Aid rich).

The assembly of gene fragments from oligonucleotides was done in a single assembly reaction with 5 nM of each construction oligo according published methods[11].

For PC-based mapping of bead positions into microscopic pictures Two reference points in the raw image and two corresponding points in the microscopic image of a plate fragment were chosen. We generated a polar coordinate system in both pictures with one corresponding reference point as the origin. The other point was used to calculate a deviation angle and a gauge factor for conversion of points from one coordinate system to the other (more details in the supplemental information).

Example 2

Analysis of Sequence Data of Mega Cloned DNA Fragments 319 clonal beads from a picotiter plate (PTP) of a 454 sequence instrument were picked. Each bead carried a different sequence from a PTP. The bead-associated nucleic acids were amplified and pooled. The pooled nucleic acid sequences were sequenced on an Illumina GAII instrument to analyse the sequence verification.

Figure 10:
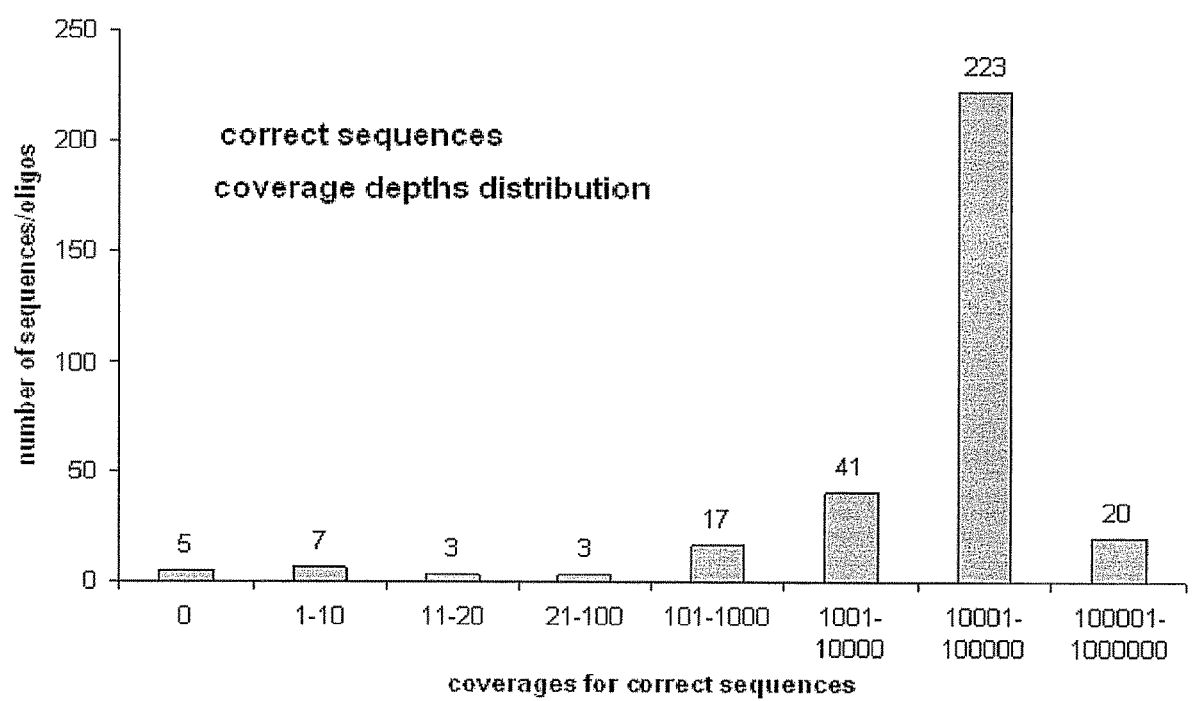

The results are shown in FIG. 10.

For 304 beads the correct sequence was found with at least 20× coverage which should be regarded as solid proof that the correct sequence has indeed been picked. With a sequence length of 40 bp fragment, the overall DNA length from this run was at least 1260 bp error-free DNA.

LIST OF REFERENCES

1. Engels, J. W., Gene synthesis on microchips. *Angew Chem Int Ed Engl* 44, 7166-7169 (2005).
2. Singh-Gasson, S., et al., Maskless fabrication of light-directed oligonucleotide microarrays using a digital micromirror array. *Nat Biotechnol* 17, 974-978 (1999).
3. Güimil, R., et al., Geniom technology—the benchtop array facility. *Nucleosides Nucleotides Nucleic Acids* 22, 1721-1723 (2003).
4. Koslov, I. A., Kaper, F., Zhou, L., & Chee, M. S., Microarray based oligonucleotide synthesis. *Nucleic Acids Symp Ser (Oxf)* 723 (2008).
5. Margulies, M., et al., Genome sequencing in microfabricated high-density picolitre reactors. *Nature* 437, 376-380 (2005).

6. Stähler, P., Beier, M., Gao, X., & Hoheisel, J. D., Another side of genomics: synthetic biology as a means for the exploitation of whole-genome sequence information. *J Biotechnol* 124, 206-212 (2006).
7. Endy, D., Foundations for engineering biology. *Nature* 438, 449-453 (2005).
8. Menzella, H. G., et al., Combinatorial polyketide biosynthesis by de novo design and rearrangement of modular polyketide synthase genes. *Nat Biotechnol* 23, 1171-1176 (2005).
9. Gibson, D. G., et al., Complete chemical synthesis, assembly, and cloning of a mycoplasma genitalium genome. *Science* 319, 1215-1220 (2008).
10. Schmidt, C., Synthetic gene firms evolve toward sustainable business? *Nat Biotechnol* 24, 1304 (2006).
11. Stemmer, W. P., Crameri, A., Ha, K. D., Brennan, T. M., & Heyneker, H. L., Single-step assembly of a gene and entire plasmid from large numbers of oligodeoxyribonucleotides. *Gene* 164, 49-53 (1995).
12. Hoover, D. M. & Lubkowski, J., Dnaworks: an automated method for designing oligonucleotides for per-based gene synthesis. *Nucleic Acids Res* 30, e43 (2002).
13. Carr, P. A., Park, J. S., Lee, Y.-J., Yu, T., Zhang, S., & Jacobson, J. M., Protein-mediated error correction for de novo dna synthesis. *Nucleic Acids Res* 32, e162 (2004).
14. Bang, D. & Church, G. M., Gene synthesis by circular assembly amplification. *Nat Methods* 5, 37-39 (2008).
15. Binkowski, B. F., Richmond, K. E., Kaysen, J., Sussman, M. R., & Belshaw, P. J., Correcting errors in synthetic dna through consensus shuffling. *Nucleic Acids Res* 33, e55 (2005).
16. Tian, J., et al., Accurate multiplex gene synthesis from programmable dna microchips. *Nature* 432, 1050-1054 (2004).
17. Fuhrmann, M., Oertel, W., Berthold, P., & Hegemann, P., Removal of mismatched bases from synthetic genes by enzymatic mismatch cleavage. *Nucleic Acids Res* 33, e58 (2005).
18. Richmond, K. E., et al., Amplification and assembly of chip-eluted dna (aaced): a method for high-throughput gene synthesis. *Nucleic Acids Res* 32, 5011-5018 (2004).
19. Wicker, T., Schlagenhauf, E., Graner, A., Close, T. J., Keller, B., & Stein, N., 454 sequencing put to the test using the complex genome of barley. *BMC Genomics* 7, 275 (2006).
20. Jefferson, R. A., Burgess, S. M., & Hirsh, D., beta-glucuronidase from *escherichia coli* as a gene-fusion marker. *Proc Natl Acad Sci USA* 83, 8447-8451 (1986).
21. Lieb, B., et al., Red blood with blue-blood ancestry: intriguing structure of a snail hemoglobin. *Proc Natl Acad Sci USA* 103, 12011-12016 (2006).
22. Couteaudier, Y., Daboussi, M. J., Eparvier, A., Langin, T., & Orcival, J., The gus gene fusion system (*escherichia coli* beta-d-glucuronidase gene), a useful tool in studies of root colonization by *fusarium oxysporum*. *Appl Environ Microbiol* 59, 1767-1773 (1993).

We claim:

1. A method of retrieving sequence verified nucleic acids from a solid support comprising: providing a mixture of nucleic acid molecules, and
   (1) generating a nucleic acid library by individualizing the mixture of nucleic acids on the solid support by physical separation of the individual nucleic acid molecules into defined locations;
   (2) sequencing the individualized members of the nucleic acid library at the single molecule level without first performing a step of amplification, and assigning a sequence to each member of the library to produce a library of sequence-verified nucleic acid molecules at the defined locations;
   (3) retrieving sequence-verified nucleic acid molecules from the solid support; and
   (4) using the retrieved molecules in continuative steps/procedures to form a larger DNA molecule.

2. The method of claim 1, wherein the method further comprises:
   (a) isolating the sequence verified nucleic acid molecules of (3).

3. The method of claim 1, wherein individualizing the mixture of nucleic acids comprises separation so that individual nucleic acids are present at a defined location on the solid support.

4. The method of claim 1, wherein (4) comprises an amplification reaction of the individualized nucleic acids, wherein the amplification comprises emulsion PCR, bridge amplification, MegaPlex PCR, creation of polonies, or/and rolling circle amplification.

5. The method of claim 1, wherein Step (2) comprises sequencing-by-synthesis or sequencing-by-ligation techniques.

6. The method of claim 1, wherein retrieval Step (3) comprises physical retrieval, physical recovery and/or extraction.

7. The method of claim 4, comprising isolating the solid support.

8. The method of claim 1, wherein the retrieval in (3) further comprises enzymatic amplification of the nucleic acids presented on the solid support.

9. The method of claim 8, comprising copying-off the nucleic acid molecules presented on the solid support by a polymerase.

10. The method of claim 1, wherein the use of the retrieved molecules in continuative steps/procedures comprises the production of a bead-array or a micro-array.

11. The method of claim 10, comprising the fabrication of a synthetic gene.

12. The method of claim 1, further comprising performing (2) to (4) in a second cycle with a sub-population selected from the nucleic acid molecules obtained in (3) of a first cycle.

13. The method of claim 1, where the defined locations on the solid support are identified by reference points in a microscopic picture of the solid support.

14. The method of claim 1 wherein the solid support is selected from the group consisting of: a particle, a bead, a microfluidic reaction support, a biochip, a DNA chip, a microtiter plate, a nanotiter plate, and a picotiter plate.

15. The method of claim 1 wherein the solid support is selected from the group consisting of: a microfluidic reaction support, a biochip, and a DNA chip.

16. The method of claim 15 wherein the solid support is a biochip.

17. The method of claim 1 wherein the method is an automated method.

18. The method of claim 1, wherein the solid support is selected from the group consisting of glass slides, gels, polymers, capillaries, microfluidic carriers, membranes, porous carriers, plastics, silicon, ordered or chaotic pores, sponge structures, cubes, a 3D matrix, emulsions, dendrimers, beads, particles, resins, metals, nano-particles and nano-structures or combinations thereof.

19. The method of claim 1 wherein retrieving sequence-verified nucleic acid molecules from the solid support comprises amplification of an individualized member of the nucleic acid library using a primer.

20. The method of claim 19 wherein the continuing steps comprise performing the polymerase chain reaction to amplify the individualized member of the nucleic acid library.

* * * * *

```
                       SEQUENCE LISTING

<160> NUMBER OF SEQ ID NOS: 249

<210> SEQ ID NO 1
<211> LENGTH: 224
<212> TYPE: DNA
<213> ORGANISM: Artificial
<220> FEATURE:
<223> OTHER INFORMATION: derived from beta-D-glucuronidase or
      Biomphalaria glabrata; DNA #1 from x=887,y=170

<400> SEQUENCE: 1
cgccatcaga cttacttcaa ttatgaagcc caacaagaca aatcagggct gcccaatgat       60
cggttctctg cagagaggcc tgagggatcc atctccactc tgaagatcca gccctcagaa      120
cccagggact cagctgtgta cttctgtgcc agcagtcacc gggacggtcc ccagcatttt      180
ggtgatggga ctcgactctc catcctagag gacctgaaca aggt                       224

<210> SEQ ID NO 2
<211> LENGTH: 246
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=887,y=170

<400> SEQUENCE: 2
acttacttca attatgaagc ccaacaagac aaatcagggc tgcccaatga tcggttctct       60
gcagagaggc ctgagggatc catctccact ctgaagatcc agccctcaga acccagggac      120
tcagctgtgt acttctgtgc cagcagtcac cgggacggtc cccagcattt tggtgatggg      180
actcgactct ccatcctaga ggacctgaac aaggtgttcc cacccgaggt cgctgtgttt      240
gagcca                                                                 246
```

```
<210> SEQ ID NO 3
<211> LENGTH: 184
<212> TYPE: DNA
<213> ORGANISM: Artificial
<220> FEATURE:
<223> OTHER INFORMATION: derived from beta-D-glucuronidase or
      Biomphalaria glabrata; DNA #2 from x=970,y=401

<400> SEQUENCE: 3
tctgcctccc tcgcgccatc aggcagattt tactcaagga cggttttctg tgaaacacat      60
tctgacccag aaagcccttc acttggtgat ctctccagta aggactgaag acagtgccac     120
ttactactgt gccttttcct ggaggacgat aaactcatct ttggaaaagg aacccgtgtg     180
actg                                                                  184

<210> SEQ ID NO 4
<211> LENGTH: 195
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=970,y=401

<400> SEQUENCE: 4
gcagatttta ctcaaggacg gttttctgtg aaacacattc tgacccagaa agcccttcac      60
ttggtgatct ctccagtaag gactgaagac agtgccactt actactgtgc cttttcctgg     120
aggacgataa actcatcttt ggaaaaggaa cccgtgtgac tgtggaacca agaagtcagc     180
ctcataccaa accat                                                      195

<210> SEQ ID NO 5
<211> LENGTH: 234
<212> TYPE: DNA
<213> ORGANISM: Artificial
<220> FEATURE:
<223> OTHER INFORMATION: derived from beta-D-glucuronidase or
      Biomphalaria glabrata; DNA #3 from x=701,y=1039

<400> SEQUENCE: 5
tgcagcctcc cttccgccat cagggagctc atgtttgtct acaactttaa agaacagact      60
gaaaacaaca gtgtgccaag tcgcttctca cctgaatgcc ccaacagctc tcacttattc     120
cttcacctac acccctgca gccagaagac tcggccctgt atctctgtgc cagcagccaa      180
gatggagtaa atcagcctca gcattttggt gatgggactc gactctccat ccta           234

<210> SEQ ID NO 6
<211> LENGTH: 245
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=701,y=1039

<400> SEQUENCE: 6
ggagctcatg tttgtctaca actttaaaga acagactgaa aacaacagtg tgccaagtcg      60
cttctcacct gaatgcccca acagctctca cttattcctt cacctacaca ccctgcagcc     120
agaagactcg gccctgtatc tctgtgccag cagccaagat ggagtaaatc agcctcagca     180
ttttggtgat gggactcgac tctccatcct agaggacctg aacaaggtgt cccacccga      240 ggtcg                                                                 245

<210> SEQ ID NO 7
```

<211> LENGTH: 183
<212> TYPE: DNA
<213> ORGANISM: Artificial
<220> FEATURE:
<223> OTHER INFORMATION: derived from beta-D-glucuronidase or
      Biomphalaria glabrata; DNA #4 from x=917,y=1182

<400> SEQUENCE: 7

```
tatgcctccc tcgcgccatc agggctttga ggctgaattt aacaagagtc aaacttcctt      60
ccacttgagg aaaccctcag tccatataag cgacacggct gagtacttct gtgctgtgag     120
ttacagcacc ctcacctttg ggaaggggac tatgcttcta gtctctccag atatccagaa     180
ccc                                                                    183
```

<210> SEQ ID NO 8
<211> LENGTH: 188
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=917,y=1182

<400> SEQUENCE: 8

```
ggctttgagg ctgaatttaa caagagtcaa acttccttcc acttgaggaa accctcagtc      60
catataagcg acacggctga gtacttctgt gctgtgagtt acagcaccct cacctttggg     120
aaggggacta tgcttctagt ctctccagat atccagaacc tgaccctgc cgtgtaccag     180
ctgagaga                                                               188
```

<210> SEQ ID NO 9
<211> LENGTH: 137
<212> TYPE: DNA
<213> ORGANISM: Artificial
<220> FEATURE:
<223> OTHER INFORMATION: derived from beta-D-glucuronidase or
      Biomphalaria glabrata; DNA #5 from x=1293,y=75

<400> SEQUENCE: 9

```
tccctcgcgc catcaggctc ttctgtctac cattggtctg ggttaaccgc tggtgcagac      60
ggtaagagaa atgctggtgt caggttggtg ctgtggatgt tcaacaacgt cccgaacatg     120
cgtgagaggt tcaccaa                                                     137
```

<210> SEQ ID NO 10
<211> LENGTH: 161
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=1293,y=75

<400> SEQUENCE: 10

```
gctcttctgt ctaccattgg tctgggttaa ccgctggtgc agacggtaag agaaatgctg      60
gtgtcaggtt ggtgctgtgg atgttcaaca acgtcccgaa catgcgtgag aggttcacca     120
agttcaacgc acgacagtca gacgaagcac tcaagcgaag a                         161
```

<210> SEQ ID NO 11
<211> LENGTH: 128
<212> TYPE: DNA
<213> ORGANISM: Artificial
<220> FEATURE:
<223> OTHER INFORMATION: derived from beta-D-glucuronidase or
      Biomphalaria glabrata; DNA #6 from x=2976,y=478

<400> SEQUENCE: 11

```
tccctcgcgc catcaggcca ggttcagtgg cagtggatct gggacagact tcactctcac    60
catcagcagt ctgcaacctg aagattttgc tacttactac tgtcaacaga gttacagtgt   120
cccccggg                                                            128
```

<210> SEQ ID NO 12
<211> LENGTH: 173
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=2976,y=478

<400> SEQUENCE: 12

```
gccaggttca gtggcagtgg atctgggaca gacttcactc tcaccatcag cagtctgcaa    60
cctgaagatt ttgctactta ctactgtcaa cagagttaca gtgtcccccc gggcgttcgg   120
ccaagggacc aaggtggaaa tcaaacgaac tgtggctgca ccatctgtct tca          173
```

<210> SEQ ID NO 13
<211> LENGTH: 152
<212> TYPE: DNA
<213> ORGANISM: Artificial
<220> FEATURE:
<223> OTHER INFORMATION: derived from beta-D-glucuronidase or
      Biomphalaria glabrata; DNA #7 from x=2852,y=689

<400> SEQUENCE: 13

```
gcctccctcg cgccatcagg ccaggttcag tggcagtggg tctgggacag agttcactct    60
caccatcagc agcctgcagt ctgaagattt gcagtttat tactgtcagc agtataataa    120
ctggccgtgg acgttcggcc aagggaccaa gg                                 152
```

<210> SEQ ID NO 14
<211> LENGTH: 172
<212> TYPE: DNA
<213> ORGANISM: Artificial
<220> FEATURE:
<223> OTHER INFORMATION: derived from beta-D-glucuronidase or
      Biomphalaria glabrata; 454 sequence @  x=2852,y=689

<400> SEQUENCE: 14

```
gccaggttca gtggcagtgg gtctgggaca gagttcactc tcaccatcag cagcctgcag    60
tctgaagatt ttgcagttta ttactgtcag cagtataata actggccgtg gacgttcggc   120
caagggacca aggtggaaat caaacgaact gtggctgcac catctgtctt ca           172
```

<210> SEQ ID NO 15
<211> LENGTH: 153
<212> TYPE: DNA
<213> ORGANISM: Artificial
<220> FEATURE:
<223> OTHER INFORMATION: derived from beta-D-glucuronidase or
      Biomphalaria glabrata; DNA #8 from x=3414,y=462

<400> SEQUENCE: 15

```
tgcctccctc gcgccatcag aaccacttct ttccacttgg agaaaggctc agttcaagtg    60
tcagactcag cggtgtactt ctgtgctctg agtgatatcg atgacatgcg ctttggagca   120
gggaccagac tgacagtaaa accaaatatc cag                                153
```

<210> SEQ ID NO 16
<211> LENGTH: 165

```
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3414,y=462

<400> SEQUENCE: 16
aaccacttct ttccacttgg agaaaggctc agttcaagtg tcagactcag cggtgtactt      60
ctgtgctctg agtgatatcg atgacatgcg ctttggagca gggaccagac tgacagtaaa     120
accaaatatc cagaaccctg accctgccgt gtaccagctg agaga                     165

<210> SEQ ID NO 17
<211> LENGTH: 191
<212> TYPE: DNA
<213> ORGANISM: Artificial
<220> FEATURE:
<223> OTHER INFORMATION: derived from beta-D-glucuronidase or
      Biomphalaria glabrata; DNA #9 from x=3243,y=545

<400> SEQUENCE: 17
tccctcgcgc catcaggaag gggctggagt gggttggccg tattagaaac aaagctaaca      60
gttacaccac agaatatgcc gcgtctgtga aaggcagatt caccatctca agagatgatt    120
caaagaactc actgtatctg caaatgaaca gcctgaaatc cgaggacacg gccgtgtatt    180
actgtgctag a                                                         191

<210> SEQ ID NO 18
<211> LENGTH: 197
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3243,y=545

<400> SEQUENCE: 18
gaaggggctg gagtgggttg gccgtattag aaacaaagct aacagttaca ccacagaata     60
tgccgcgtct gtgaaaggca gattcaccat ctcaagagat gattcaaaga actcactgta    120
tctgcaaatg aacagcctga aatccgagga cacggccgtg tattactgtg ctagagcctt    180
aagctacttt gactact                                                   197

<210> SEQ ID NO 19
<211> LENGTH: 187
<212> TYPE: DNA
<213> ORGANISM: Artificial
<220> FEATURE:
<223> OTHER INFORMATION: derived from beta-D-glucuronidase or
      Biomphalaria glabrata; DNA #10 from x=3410,y=881

<400> SEQUENCE: 19
tccctcccgc catcagcaag tggaagactt aatgcctcgc tggataaatc atcaggacgt     60
agtactttat acattgcagc ttctcagcct ggtgactcag ccacctacct ctgtgctccc    120
gaagcgatgg gcggatctga aaagctggtc tttggaaagg gaacgaaact gacagtaaac    180
ccatata                                                              187

<210> SEQ ID NO 20
<211> LENGTH: 208
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3410,y=881
```

<400> SEQUENCE: 20

```
caagtggaag acttaatgcc tcgctggata aatcatcagg acgtagtact ttatacattg    60
cagcttctca gcctggtgac tcagccacct acctctgtgc tcccgaagcg atgggcggat   120
ctgaaaagct ggtctttgga aagggaacga aactgacagt aaacccatat atccagaacc   180
ctgaccctgc cgtgtaccag ctgagaga                                      208
```

<210> SEQ ID NO 21
<211> LENGTH: 139
<212> TYPE: DNA
<213> ORGANISM: Artificial
<220> FEATURE:
<223> OTHER INFORMATION: derived from beta-D-glucuronidase or
      Biomphalaria glabrata; DNA #11 from x=3662,y=523

<400> SEQUENCE: 21

```
cctccctcgc gccatcagac tctcaagatc cagcctgcag agcttgggga ctcggccgtg    60
tatctctgtg ccagcagctt agaaacaggg gctccggctt tctttggaca aggcaccaga   120
ctcacagttg tagaggacc                                                139
```

<210> SEQ ID NO 22
<211> LENGTH: 165
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3662,y=523

<400> SEQUENCE: 22

```
actctcaaga tccagcctgc agagcttggg gactcggccg tgtatctctg tgccagcagc    60
ttagaaacag gggctccggc tttctttgga caaggcacca gactcacagt tgtagaggac   120
ctgaacaagg tgttcccacc cgaggtcgct gtgtttgagc catca                   165
```

<210> SEQ ID NO 23
<211> LENGTH: 279
<212> TYPE: DNA
<213> ORGANISM: Artificial
<220> FEATURE:
<223> OTHER INFORMATION: derived from beta-D-glucuronidase or
      Biomphalaria glabrata; DNA #12 from x=3672,y=569

<400> SEQUENCE: 23

```
cgccatcaga ggaggggaag accccacagc gtcttctgta ctatgactcc tacaactcca    60
aggttgtgtt ggaatcagga gtcagtccag ggaagcatta tacttacgca agcacaagga   120
acaacttgag attgatactg cgaaatctaa gtgaaaatga ctctgggtct attactgtgc   180
cacctgggac gggcaataag aaactctttg gcagtggaac aacacttgtt gtcacagata   240
aacaacttga tgcagatgtt tcccccaggc ccactattt                          279
```

<210> SEQ ID NO 24
<211> LENGTH: 260
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3672,y=569

<400> SEQUENCE: 24

```
aggaggggaa gaccccacag cgtcttctgt actatgactc ctacaactcc aaggttgtgt    60
```
tggaatcagg agtcagtcca gggaagcatt atacttacgc aagcacaagg aacaacttga    120
gattgatact gcgaaatcta agtgaaaatg actctgggtc tattactgtg ccacctggga    180
cgggcaataa gaaactcttt ggcagtggaa caacacttgt tgtcacagat aaacaacttg    240
atgcagatgt ttcccccagg                                                260

<210> SEQ ID NO 25
<211> LENGTH: 202
<212> TYPE: DNA
<213> ORGANISM: Artificial
<220> FEATURE:
<223> OTHER INFORMATION: derived from beta-D-glucuronidase or
      Biomphalaria glabrata; DNA #13 from x=3668,y=609

<400> SEQUENCE: 25
gccatcagtg aggtgactga taagggagat gttcctgaag ggtacaaagt ctctcgaaaa     60
gagaagagga atttccccct gatcctggag tcgcccagcc ccaaccagac ctctctgtac    120
ttctgtgcca gcagtttaag gagacagggt ggtgaaaaac tgttttttgg cagtggaacc    180
cagctctctg tcttggagga cc                                             202

<210> SEQ ID NO 26
<211> LENGTH: 239
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3668,y=609

<400> SEQUENCE: 26
tgaggtgact gataagggag atgttcctga agggtacaaa gtctctcgaa aagagaagag     60
gaatttcccc cctgatcctg gagtcgccca gccccaacca gacctctctg tacttctgtg    120
ccagcagttt aaggagacag ggtggtgaaa aactgttttt tggcagtgga acccagctct    180
ctgtcttgga ggacctgaac aaggtgttcc cacccgaggt cgctgtgttt gagccatca    239

<210> SEQ ID NO 27
<211> LENGTH: 140
<212> TYPE: DNA
<213> ORGANISM: Artificial
<220> FEATURE:
<223> OTHER INFORMATION: derived from beta-D-glucuronidase or
      Biomphalaria glabrata; DNA #14 from x=3800,y=664

<400> SEQUENCE: 27
ctccctcgcg ccatcaggcc aggttcagtg gcagtggatc tgggacagaa ttcactctca     60
caatcagcag cctgcagcct gaagattttg caacttatta ctgtctacag cataatagtt    120
accctcgggg gttcggccaa                                                140

<210> SEQ ID NO 28
<211> LENGTH: 172
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3800,y=664

<400> SEQUENCE: 28
gccaggttca gtggcagtgg atctgggaca gaattcactc tcacaatcag cagcctgcag     60
cctgaagatt ttgcaactta ttactgtcta cagcataata gttaccctcg ggggttcggc    120
caagggacca aggtggaaat caaacgaact gtggctgcac catcagtctt ca            172

<210> SEQ ID NO 29
<211> LENGTH: 128
<212> TYPE: DNA
<213> ORGANISM: Artificial
<220> FEATURE:
<223> OTHER INFORMATION: derived from beta-D-glucuronidase or
      Biomphalaria glabrata; DNA #15 from x=3915,y=921

<400> SEQUENCE: 29
cgcgccatca gtcgaggttc agtggcagtg ggtctgggac agacttcact ctcaccatca    60
gcagactgga gcctgaagat tttgcagttt attactgtca acagtatggt tattggtacg   120
cttttggc                                                            128

<210> SEQ ID NO 30
<211> LENGTH: 169
<212> TYPE: DNA
<213> ORGANISM: Artificial
<220> FEATURE:
<223> OTHER INFORMATION: derived from beta-D-glucuronidase or
      Biomphalaria glabrata; 454 sequence @ x=3915,y=921

<400> SEQUENCE: 30
tcgaggttca gtggcagtgg gtctgggaca gacttcactc tcaccatcag cagactggag    60
cctgaagatt ttgcagttta ttactgtcaa cagtatggtt attggtacgc ttttggccag   120
gggaccaagc tggagatcaa acgaactgtg gctgcaccat ctgtcttca               169

<210> SEQ ID NO 31
<211> LENGTH: 19
<212> TYPE: DNA
<213> ORGANISM: Artificial
<220> FEATURE:
<223> OTHER INFORMATION: derived from beta-D-glucuronidase or
      Biomphalaria glabrata; primer sequence GS-FLX-A

<400> SEQUENCE: 31
gcctccctcg cgccatcag                                                 19

<210> SEQ ID NO 32
<211> LENGTH: 19
<212> TYPE: DNA
<213> ORGANISM: Artificial
<220> FEATURE:
<223> OTHER INFORMATION: derived from beta-D-glucuronidase or
      Biomphalaria glabrata; primer sequence GS-FLX-B

<400> SEQUENCE: 32
gccttgccag cccgctcag                                                 19

<210> SEQ ID NO 33
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_1

<400> SEQUENCE: 33
cgactgcacg gtgaccaatg cttctggcgt caggcagcca                          40

<210> SEQ ID NO 34
<211> LENGTH: 40
<212> TYPE: DNA
<213> ORGANISM: Artificial

```
<220> FEATURE:
<223> OTHER INFORMATION: derived from beta-D-glucuronidase; construction
      oligo uidA_2

<400> SEQUENCE: 34
agccatacca cagcttccga tggctgcctg acgccagaag                              40

<210> SEQ ID NO 35
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_3

<400> SEQUENCE: 35
tcggaagctg tggtatggct gtgcaggtcg taaatcactg                              40

<210> SEQ ID NO 36
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_4

<400> SEQUENCE: 36
cttgagcgac acgaattatg cagtgattta cgacctgcac                              40

<210> SEQ ID NO 37
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_5

<400> SEQUENCE: 37
cataattcgt gtcgctcaag gcgcactccc gttctggata                              40

<210> SEQ ID NO 38
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_6

<400> SEQUENCE: 38
gatgtcggcg caaaaaacat tatccagaac gggagtgcgc                              40

<210> SEQ ID NO 39
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_7

<400> SEQUENCE: 39
atgttttttg cgccgacatc ataacggttc tggcaaatat                              40

<210> SEQ ID NO 40
<211> LENGTH: 40
<212> TYPE: DNA
<213> ORGANISM: Artificial
<220> FEATURE:
```

```
<223> OTHER INFORMATION: derived from beta-D-glucuronidase; construction
      oligo uidA_8

<400> SEQUENCE: 40
tgtcaacagc tcatttcaga atatttgcca gaaccgttat                          40

<210> SEQ ID NO 41
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_9

<400> SEQUENCE: 41
tctgaaatga gctgttgaca attaatcatc ggctcgtata                          40

<210> SEQ ID NO 42
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_10

<400> SEQUENCE: 42
ccgctcacaa ttccacacat tatacgagcc gatgattaat                          40

<210> SEQ ID NO 43
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_11

<400> SEQUENCE: 43
atgtgtggaa ttgtgagcgg ataacaattt cacacaggaa                          40

<210> SEQ ID NO 44
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_12

<400> SEQUENCE: 44
ggcggagcat tgaattctgt ttcctgtgtg aaattgttat                          40

<210> SEQ ID NO 45
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_13

<400> SEQUENCE: 45
acagaattca tgctccgcc cagtcgaaac cccaacccga                           40

<210> SEQ ID NO 46
<211> LENGTH: 40
<212> TYPE: DNA
<213> ORGANISM: Artificial
<220> FEATURE:
<223> OTHER INFORMATION: derived from beta-D-glucuronidase; construction
``` oligo uidA_14

<400> SEQUENCE: 46
ccatccagtt ttttaatctc tcgggttggg gtttcgactg                                 40

<210> SEQ ID NO 47
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_15

<400> SEQUENCE: 47
gagattaaaa aactggatgg cctgtgggca tttagcctgg                                 40

<210> SEQ ID NO 48
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_16

<400> SEQUENCE: 48
aatgccgcag ttttcgcgat ccaggctaaa tgcccacagg                                 40

<210> SEQ ID NO 49
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_17

<400> SEQUENCE: 49
atcgcgaaaa ctgcggcatt gatcaacgtt ggtgggaatc                                 40

<210> SEQ ID NO 50
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_18

<400> SEQUENCE: 50
ctcgactttc ctgtagcgca gattcccacc aacgttgatc                                 40

<210> SEQ ID NO 51
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_19

<400> SEQUENCE: 51
tgcgctacag gaaagtcgag cgattgcagt accggggagc                                 40

<210> SEQ ID NO 52
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_20

```
<400> SEQUENCE: 52
tccgcaaact gatcgttaaa gctccccggt actgcaatcg                              40

<210> SEQ ID NO 53
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_21

<400> SEQUENCE: 53
tttaacgatc agtttgcgga tgccgatatt cgcaactatg                              40

<210> SEQ ID NO 54
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_22

<400> SEQUENCE: 54
ctgataccaa acgttccccg catagttgcg aatatcggca                              40

<210> SEQ ID NO 55
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_23

<400> SEQUENCE: 55
cggggaacgt ttggtatcag cgggaagtgt ttataccgaa                              40

<210> SEQ ID NO 56
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_24

<400> SEQUENCE: 56
tgcgctgtcc agcccagcct ttcggtataa acacttcccg                              40

<210> SEQ ID NO 57
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_25

<400> SEQUENCE: 57
aggctgggct ggacagcgca tagtcttacg ctttgatgcc                              40

<210> SEQ ID NO 58
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_26
```

<400> SEQUENCE: 58
actttgccat agtgggtcac ggcatcaaag cgtaagacta    40

<210> SEQ ID NO 59
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_27

<400> SEQUENCE: 59
gtgacccact atggcaaagt gtgggtgaac aaccaggaag    40

<210> SEQ ID NO 60
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_28

<400> SEQUENCE: 60
gcctccctga tgttccatca cttcctggtt gttcacccac    40

<210> SEQ ID NO 61
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_29

<400> SEQUENCE: 61
tgatggaaca tcagggaggc tacactccct ttgaagcaga    40

<210> SEQ ID NO 62
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_30

<400> SEQUENCE: 62
caatcacata cggggtcaca tctgcttcaa agggagtgta    40

<210> SEQ ID NO 63
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_31

<400> SEQUENCE: 63
tgtgaccccg tatgtgattg cgggcaaatc agtgaggatt    40

<210> SEQ ID NO 64
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_32

<400> SEQUENCE: 64
tcgttgttga cgcacacggt aatcctcact gatttgcccg          40

<210> SEQ ID NO 65
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_33

<400> SEQUENCE: 65
accgtgtgcg tcaacaacga actgaactgg cagacaatac          40

<210> SEQ ID NO 66
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_34

<400> SEQUENCE: 66
cgtgataacc ataccgggcg gtattgtctg ccagttcagt          40

<210> SEQ ID NO 67
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_35

<400> SEQUENCE: 67
cgcccggtat ggttatcacg gacgagaacg gcaaaaagaa          40

<210> SEQ ID NO 68
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_36

<400> SEQUENCE: 68
agtcgtgaaa gtacgactgt tcttttttgc cgttctcgtc          40

<210> SEQ ID NO 69
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_37

<400> SEQUENCE: 69
acagtcgtac tttcacgact tttttaacta tgccggcatt          40

<210> SEQ ID NO 70
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_38

<400> SEQUENCE: 70
tacagcataa ccgagcggtg aatgccggca tagttaaaaa          40

<210> SEQ ID NO 71
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_39

<400> SEQUENCE: 71
caccgctcgg ttatgctgta tacgaccccg aatacctggg          40

<210> SEQ ID NO 72
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_40

<400> SEQUENCE: 72
cactacggtg atatcatcga cccaggtatt cggggtcgta          40

<210> SEQ ID NO 73
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_41

<400> SEQUENCE: 73
tcgatgatat caccgtagtg acacacgtgg cgcaagattg          40

<210> SEQ ID NO 74
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_42

<400> SEQUENCE: 74
aatccacact cgcatgattg caatcttgcg ccacgtgtgt          40

<210> SEQ ID NO 75
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_43

<400> SEQUENCE: 75
caatcatgcg agtgtggatt ggcaagtcgt ggcgaatggc          40

<210> SEQ ID NO 76
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_44

<400> SEQUENCE: 76
cttagttcta cgcttacatc gccattcgcc acgacttgcc          40

<210> SEQ ID NO 77
<211> LENGTH: 40
<212> TYPE: DNA
<213> ORGANISM: Artificial
<220> FEATURE:
<223> OTHER INFORMATION: derived from beta-D-glucuronidase; construction oligo uidA_45

<400> SEQUENCE: 77
gatgtaagcg tagaactaag ggatgcggat cagcaagtgg                                    40

<210> SEQ ID NO 78
<211> LENGTH: 40
<212> TYPE: DNA
<213> ORGANISM: Artificial
<220> FEATURE:
<223> OTHER INFORMATION: derived from beta-D-glucuronidase; construction oligo uidA_46

<400> SEQUENCE: 78
ggtaccctgg ccggttgcta ccacttgctg atccgcatcc                                    40

<210> SEQ ID NO 79
<211> LENGTH: 40
<212> TYPE: DNA
<213> ORGANISM: Artificial
<220> FEATURE:
<223> OTHER INFORMATION: derived from beta-D-glucuronidase; construction oligo uidA_47

<400> SEQUENCE: 79
tagcaaccgg ccagggtacc agcggtacct tgcaagtggt                                    40

<210> SEQ ID NO 80
<211> LENGTH: 40
<212> TYPE: DNA
<213> ORGANISM: Artificial
<220> FEATURE:
<223> OTHER INFORMATION: derived from beta-D-glucuronidase; construction oligo uidA_48

<400> SEQUENCE: 80
gttgccacag atgaggattc accacttgca aggtaccgct                                    40

<210> SEQ ID NO 81
<211> LENGTH: 40
<212> TYPE: DNA
<213> ORGANISM: Artificial
<220> FEATURE:
<223> OTHER INFORMATION: derived from beta-D-glucuronidase; construction oligo uidA_49

<400> SEQUENCE: 81
gaatcctcat ctgtggcaac ctggagaagg ctatctgtat                                    40

<210> SEQ ID NO 82
<211> LENGTH: 40
<212> TYPE: DNA
<213> ORGANISM: Artificial
<220> FEATURE:
<223> OTHER INFORMATION: derived from beta-D-glucuronidase; construction oligo uidA_50

<400> SEQUENCE: 82
ttggccgtaa cgcacagctc atacagatag ccttctccag                                    40

<210> SEQ ID NO 83
<211> LENGTH: 40
<212> TYPE: DNA
<213> ORGANISM: Artificial
<220> FEATURE:
<223> OTHER INFORMATION: derived from beta-D-glucuronidase; construction oligo uidA_51

<400> SEQUENCE: 83
gagctgtgcg ttacggccaa atctcagacg gaatgcgaca          40

<210> SEQ ID NO 84
<211> LENGTH: 40
<212> TYPE: DNA
<213> ORGANISM: Artificial
<220> FEATURE:
<223> OTHER INFORMATION: derived from beta-D-glucuronidase; construction oligo uidA_52

<400> SEQUENCE: 84
gcccacgcga agaggataga tgtcgcattc cgtctgagat          40

<210> SEQ ID NO 85
<211> LENGTH: 40
<212> TYPE: DNA
<213> ORGANISM: Artificial
<220> FEATURE:
<223> OTHER INFORMATION: derived from beta-D-glucuronidase; construction oligo uidA_53

<400> SEQUENCE: 85
tctatcctct tcgcgtgggc attagatcag tagccgtgaa          40

<210> SEQ ID NO 86
<211> LENGTH: 40
<212> TYPE: DNA
<213> ORGANISM: Artificial
<220> FEATURE:
<223> OTHER INFORMATION: derived from beta-D-glucuronidase; construction oligo uidA_54

<400> SEQUENCE: 86
taatcaggaa ctgttcgcct ttcacggcta ctgatctaat          40

<210> SEQ ID NO 87
<211> LENGTH: 40
<212> TYPE: DNA
<213> ORGANISM: Artificial
<220> FEATURE:
<223> OTHER INFORMATION: derived from beta-D-glucuronidase; construction oligo uidA_55

<400> SEQUENCE: 87
aggcgaacag ttcctgatta accacaagcc gttctacttt          40

<210> SEQ ID NO 88
<211> LENGTH: 40
<212> TYPE: DNA
<213> ORGANISM: Artificial
<220> FEATURE:
<223> OTHER INFORMATION: derived from beta-D-glucuronidase; construction oligo uidA_56

<400> SEQUENCE: 88
tcatggcgac caaaaccggt aaagtagaac ggcttgtggt          40

```
<210> SEQ ID NO 89
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_57

<400> SEQUENCE: 89
accggttttg gtcgccatga agacgctgat ctgcgcggca                              40

<210> SEQ ID NO 90
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_58

<400> SEQUENCE: 90
caggacgttg tcaaagcctt tgccgcgcag atcagcgtct                              40

<210> SEQ ID NO 91
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_59

<400> SEQUENCE: 91
aaggctttga caacgtcctg atggtgcatg atcatgcgct                              40

<210> SEQ ID NO 92
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_60

<400> SEQUENCE: 92
tggcccctat ccaatccatg agcgcatgat catgcaccat                              40

<210> SEQ ID NO 93
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_61

<400> SEQUENCE: 93
catggattgg atagggggcca acagctatcg tacttcccac                             40

<210> SEQ ID NO 94
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_62

<400> SEQUENCE: 94
atctcttcgg catacgggta gtgggaagta cgatagctgt                              40

<210> SEQ ID NO 95
```

<211> LENGTH: 40
<212> TYPE: DNA
<213> ORGANISM: Artificial
<220> FEATURE:
<223> OTHER INFORMATION: derived from beta-D-glucuronidase; construction oligo uidA_63

<400> SEQUENCE: 95
tacccgtatg ccgaagagat gttagattgg gcggacgaac        40

<210> SEQ ID NO 96
<211> LENGTH: 40
<212> TYPE: DNA
<213> ORGANISM: Artificial
<220> FEATURE:
<223> OTHER INFORMATION: derived from beta-D-glucuronidase; construction oligo uidA_64

<400> SEQUENCE: 96
atcgatcacg actatgccat gttcgtccgc ccaatctaac        40

<210> SEQ ID NO 97
<211> LENGTH: 40
<212> TYPE: DNA
<213> ORGANISM: Artificial
<220> FEATURE:
<223> OTHER INFORMATION: derived from beta-D-glucuronidase; construction oligo uidA_65

<400> SEQUENCE: 97
atggcatagt cgtgatcgat gaaacagctg ccgtggggtt        40

<210> SEQ ID NO 98
<211> LENGTH: 40
<212> TYPE: DNA
<213> ORGANISM: Artificial
<220> FEATURE:
<223> OTHER INFORMATION: derived from beta-D-glucuronidase; construction oligo uidA_66

<400> SEQUENCE: 98
caatgcctag tgaaaggtta aaccccacgg cagctgtttc        40

<210> SEQ ID NO 99
<211> LENGTH: 40
<212> TYPE: DNA
<213> ORGANISM: Artificial
<220> FEATURE:
<223> OTHER INFORMATION: derived from beta-D-glucuronidase; construction oligo uidA_67

<400> SEQUENCE: 99
taacctttca ctaggcattg ggttcgaagc cggcaacaaa        40

<210> SEQ ID NO 100
<211> LENGTH: 40
<212> TYPE: DNA
<213> ORGANISM: Artificial
<220> FEATURE:
<223> OTHER INFORMATION: derived from beta-D-glucuronidase; construction oligo uidA_68

<400> SEQUENCE: 100
tcactgtaca gttctttcgg tttgttgccg gcttcgaacc        40

<210> SEQ ID NO 101
<211> LENGTH: 40

```
<212> TYPE: DNA
<213> ORGANISM: Artificial
<220> FEATURE:
<223> OTHER INFORMATION: derived from beta-D-glucuronidase; construction
      oligo uidA_69

<400> SEQUENCE: 101
ccgaaagaac tgtacagtga ggaagcagtc aacggagaaa                               40

<210> SEQ ID NO 102
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_70

<400> SEQUENCE: 102
ctgcagatgt gcctgttgag tttctccgtt gactgcttcc                               40

<210> SEQ ID NO 103
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_71

<400> SEQUENCE: 103
ctcaacaggc acatctgcag gcgataaagg aactgattgc                               40

<210> SEQ ID NO 104
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_72

<400> SEQUENCE: 104
acggatggtt cttatcgcgc gcaatcagtt cctttatcgc                               40

<210> SEQ ID NO 105
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_73

<400> SEQUENCE: 105
gcgcgataag aaccatccgt ccgtcgtgat gtggagcata                               40

<210> SEQ ID NO 106
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_74

<400> SEQUENCE: 106
cgcgtatctg gttcattcgc tatgctccac atcacgacgg                               40

<210> SEQ ID NO 107
<211> LENGTH: 40
<212> TYPE: DNA
```

<213> ORGANISM: Artificial
<220> FEATURE:
<223> OTHER INFORMATION: derived from beta-D-glucuronidase; construction oligo uidA_75

<400> SEQUENCE: 107
gcgaatgaac cagatacgcg tcctcaagga gctagggaat                          40

<210> SEQ ID NO 108
<211> LENGTH: 40
<212> TYPE: DNA
<213> ORGANISM: Artificial
<220> FEATURE:
<223> OTHER INFORMATION: derived from beta-D-glucuronidase; construction oligo uidA_76

<400> SEQUENCE: 108
ttccgcgagc ggagcaaaat attccctagc tccttgagga                          40

<210> SEQ ID NO 109
<211> LENGTH: 40
<212> TYPE: DNA
<213> ORGANISM: Artificial
<220> FEATURE:
<223> OTHER INFORMATION: derived from beta-D-glucuronidase; construction oligo uidA_77

<400> SEQUENCE: 109
attttgctcc gctcgcggaa gctaccagaa aactagatcc                          40

<210> SEQ ID NO 110
<211> LENGTH: 40
<212> TYPE: DNA
<213> ORGANISM: Artificial
<220> FEATURE:
<223> OTHER INFORMATION: derived from beta-D-glucuronidase; construction oligo uidA_78

<400> SEQUENCE: 110
cgcaagtaat cgggcgagtg ggatctagtt ttctggtagc                          40

<210> SEQ ID NO 111
<211> LENGTH: 40
<212> TYPE: DNA
<213> ORGANISM: Artificial
<220> FEATURE:
<223> OTHER INFORMATION: derived from beta-D-glucuronidase; construction oligo uidA_79

<400> SEQUENCE: 111
cactcgcccg attacttgcg tcaacgtgat gttttgcgat                          40

<210> SEQ ID NO 112
<211> LENGTH: 40
<212> TYPE: DNA
<213> ORGANISM: Artificial
<220> FEATURE:
<223> OTHER INFORMATION: derived from beta-D-glucuronidase; construction oligo uidA_80

<400> SEQUENCE: 112
ctaatggtgt cggtatgcgc atcgcaaaac atcacgttga                          40

<210> SEQ ID NO 113
<211> LENGTH: 40
<212> TYPE: DNA
<213> ORGANISM: Artificial

<220> FEATURE:
<223> OTHER INFORMATION: derived from beta-D-glucuronidase; construction oligo uidA_81

<400> SEQUENCE: 113
gcgcataccg acaccattag cgacctgttt gatgtgctgt                40

<210> SEQ ID NO 114
<211> LENGTH: 40
<212> TYPE: DNA
<213> ORGANISM: Artificial
<220> FEATURE:
<223> OTHER INFORMATION: derived from beta-D-glucuronidase; construction oligo uidA_82

<400> SEQUENCE: 114
accgtaatag cggttcaggc acagcacatc aaacaggtcg                40

<210> SEQ ID NO 115
<211> LENGTH: 40
<212> TYPE: DNA
<213> ORGANISM: Artificial
<220> FEATURE:
<223> OTHER INFORMATION: derived from beta-D-glucuronidase; construction oligo uidA_83

<400> SEQUENCE: 115
gcctgaaccg ctattacggt tggtatgtac agtcagggga                40

<210> SEQ ID NO 116
<211> LENGTH: 40
<212> TYPE: DNA
<213> ORGANISM: Artificial
<220> FEATURE:
<223> OTHER INFORMATION: derived from beta-D-glucuronidase; construction oligo uidA_84

<400> SEQUENCE: 116
ctttctccgc agtttccaga tcccctgact gtacatacca                40

<210> SEQ ID NO 117
<211> LENGTH: 40
<212> TYPE: DNA
<213> ORGANISM: Artificial
<220> FEATURE:
<223> OTHER INFORMATION: derived from beta-D-glucuronidase; construction oligo uidA_85

<400> SEQUENCE: 117
tctggaaact gcggagaaag tactggagaa agagctgcta                40

<210> SEQ ID NO 118
<211> LENGTH: 40
<212> TYPE: DNA
<213> ORGANISM: Artificial
<220> FEATURE:
<223> OTHER INFORMATION: derived from beta-D-glucuronidase; construction oligo uidA_86

<400> SEQUENCE: 118
tggagtttct cctgccaagc tagcagctct ttctccagta                40

<210> SEQ ID NO 119
<211> LENGTH: 40
<212> TYPE: DNA
<213> ORGANISM: Artificial
<220> FEATURE:

```
<223> OTHER INFORMATION: derived from beta-D-glucuronidase; construction
      oligo uidA_87

<400> SEQUENCE: 119
gcttggcagg agaaactcca tcagccgatt attatcacgg                              40

<210> SEQ ID NO 120
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_88

<400> SEQUENCE: 120
tagggtgtct accccatatt ccgtgataat aatcggctga                              40

<210> SEQ ID NO 121
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_89

<400> SEQUENCE: 121
aatatggggt agacaccta gcaggtctcc atagcatgta                               40

<210> SEQ ID NO 122
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_90

<400> SEQUENCE: 122
cctcagacca catgtccgtg tacatgctat ggagacctgc                              40

<210> SEQ ID NO 123
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_91

<400> SEQUENCE: 123
cacggacatg tggtctgagg aataccagtg tgcctggctg                              40

<210> SEQ ID NO 124
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_92

<400> SEQUENCE: 124
aacacgcgat gatacatatc cagccaggca cactggtatt                              40

<210> SEQ ID NO 125
<211> LENGTH: 40
<212> TYPE: DNA
<213> ORGANISM: Artificial
<220> FEATURE:
<223> OTHER INFORMATION: derived from beta-D-glucuronidase; construction
``` oligo uidA_93

<400> SEQUENCE: 125
gatatgtatc atcgcgtgtt tgatagggtc tcagccgtgg                                                    40

<210> SEQ ID NO 126
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_94

<400> SEQUENCE: 126
gttccaaacc tgctcaccca ccacggctga gaccctatca                                                    40

<210> SEQ ID NO 127
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_95

<400> SEQUENCE: 127
tgggtgagca ggtttggaac tttgcggact ttgcaacgtc                                                    40

<210> SEQ ID NO 128
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_96

<400> SEQUENCE: 128
ccacacgcaa aatcccttga gacgttgcaa agtccgcaaa                                                    40

<210> SEQ ID NO 129
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_97

<400> SEQUENCE: 129
tcaagggatt ttgcgtgtgg gcgggaacaa gaaaggcatt                                                    40

<210> SEQ ID NO 130
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_98

<400> SEQUENCE: 130
ggcttgcgat ctctggtgaa aatgcctttc ttgttcccgc                                                    40

<210> SEQ ID NO 131
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_99

<210> SEQ ID NO 132
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_100

<400> SEQUENCE: 132
ccccgtccag cgcttctgca atagaaaagc ggcgcttttc                          40

<210> SEQ ID NO 133
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_101

<400> SEQUENCE: 133
tgcagaagcg ctggacgggg atgaattttg gcgaaaaacc                          40

<210> SEQ ID NO 134
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_102

<400> SEQUENCE: 134
gttgtttacc gccctgctgg ggttttttcgc caaaattcat                         40

<210> SEQ ID NO 135
<211> LENGTH: 40
<212> TYPE: DNA
<213> ORGANISM: Artificial
<220> FEATURE:
<223> OTHER INFORMATION: derived from beta-D-glucuronidase; construction
      oligo uidA_103

<400> SEQUENCE: 135
ccagcagggc ggtaaacaac atcaccatca ccatcactaa                          40

<210> SEQ ID NO 136
<211> LENGTH: 20
<212> TYPE: DNA
<213> ORGANISM: Artificial
<220> FEATURE:
<223> OTHER INFORMATION: derived from beta-D-glucuronidase; construction
      oligo uidA_104

<400> SEQUENCE: 136
ttagtgatgg tgatggtgat                                                20

<210> SEQ ID NO 137
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_1

<400> SEQUENCE: 137
ggggacaagt ttgtacaaaa aagcaggctt cgaaggagat                              40

<210> SEQ ID NO 138
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_2

<400> SEQUENCE: 138
aggacgaaca tcatggttct atctccttcg aagcctgctt                              40

<210> SEQ ID NO 139
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_3

<400> SEQUENCE: 139
agaaccatga tgttcgtcct taagggatcc gtcgtccaag                              40

<210> SEQ ID NO 140
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_4

<400> SEQUENCE: 140
gatgctcaac aggacgaatg cttggacgac ggatcccgta                              40

<210> SEQ ID NO 141
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_5

<400> SEQUENCE: 141
cattcgtcct gttgagcatc gtctgcctcg aaatcaccat                              40

<210> SEQ ID NO 142
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_6

<400> SEQUENCE: 142
acctgacacc gtcgtctgct atggtgattt cgaggcagac                              40

<210> SEQ ID NO 143
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_7

<400> SEQUENCE: 143
agcagacgac ggtgtcaggt atgtgaacgc tgagtggaag            40

<210> SEQ ID NO 144
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_8

<400> SEQUENCE: 144
tcttgggatt gttctggacg cttccactca gcgttcacat            40

<210> SEQ ID NO 145
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_9

<400> SEQUENCE: 145
cgtccagaac aatcccaaga aggtaggcac tctagaacgg            40

<210> SEQ ID NO 146
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_10

<400> SEQUENCE: 146
gttgtcctct aacctcctag ccgttctaga gtgcctacct            40

<210> SEQ ID NO 147
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_11

<400> SEQUENCE: 147
ctaggaggtt agaggacaac tctgaggaag tcgcatgctc            40

<210> SEQ ID NO 148
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_12

<400> SEQUENCE: 148
gtcggaactt cacttccgta gagcatgcga cttcctcaga            40

<210> SEQ ID NO 149
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_13

<400> SEQUENCE: 149

```
tacggaagtg aagttccgac agagagctcc tgccgagtac                           40
```

<210> SEQ ID NO 150
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_14

<400> SEQUENCE: 150

```
gccttcttga tcttgttagc gtactcggca ggagctctct                           40
```

<210> SEQ ID NO 151
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_15

<400> SEQUENCE: 151

```
gctaacaaga tcaagaaggc aaaggacaag ctgcggagac                           40
```

<210> SEQ ID NO 152
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_16

<400> SEQUENCE: 152

```
atcgtcgaac tgagattcca gtctccgcag cttgtccttt                           40
```

<210> SEQ ID NO 153
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_17

<400> SEQUENCE: 153

```
tggaatctca gttcgacgat tgccagcagg aaaacgacag                           40
```

<210> SEQ ID NO 154
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_18

<400> SEQUENCE: 154

```
gttggatcag cctgtccttc ctgtcgtttt cctgctggca                           40
```

<210> SEQ ID NO 155
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_19

<400> SEQUENCE: 155

```
gaaggacagg ctgatccaac tccaagcaaa cctcaccgat                           40
```

```
<210> SEQ ID NO 156
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_20

<400> SEQUENCE: 156
gttacgagcc tgtggatggt atcggtgagg tttgcttgga                              40

<210> SEQ ID NO 157
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_21

<400> SEQUENCE: 157
accatccaca ggctcgtaac cgactctgac attcaggcac                              40

<210> SEQ ID NO 158
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_22

<400> SEQUENCE: 158
agtagcccag gatgacctaa gtgcctgaat gtcagagtcg                              40

<210> SEQ ID NO 159
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_23

<400> SEQUENCE: 159
ttaggtcatc ctgggctact ttgaccgctg gtgctgatgg                              40

<210> SEQ ID NO 160
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_24

<400> SEQUENCE: 160
tgttaccgaa gttgttccgt ccatcagcac cagcggtcaa                              40

<210> SEQ ID NO 161
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_25

<400> SEQUENCE: 161
acggaacaac ttcggtaaca acttcgtgct gtggctactg                              40
```

<210> SEQ ID NO 162
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_26

<400> SEQUENCE: 162
cttatgttcg ggatcgtgtt cagtagccac agcacgaagt         40

<210> SEQ ID NO 163
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_27

<400> SEQUENCE: 163
aacacgatcc cgaacataag ggagcgtttc gagaagttca         40

<210> SEQ ID NO 164
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_28

<400> SEQUENCE: 164
ttcatcgctc tggtgagcgt tgaacttctc gaaacgctcc         40

<210> SEQ ID NO 165
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_29

<400> SEQUENCE: 165
acgctcacca gagcgatgaa gccctcaaga acgacaacga         40

<210> SEQ ID NO 166
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_30

<400> SEQUENCE: 166
gcttcacctg cttcacgaat tcgttgtcgt tcttgagggc         40

<210> SEQ ID NO 167
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_31

<400> SEQUENCE: 167
attcgtgaag caggtgaagc tgatcgttgg tggactgcag         40

-continued

```
<210> SEQ ID NO 168
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_32

<400> SEQUENCE: 168
tcgaggttgt cgatgaagct ctgcagtcca ccaacgatca                              40

<210> SEQ ID NO 169
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_33

<400> SEQUENCE: 169
agcttcatcg acaacctcga aaaccctggt cagctgcaag                              40

<210> SEQ ID NO 170
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_34

<400> SEQUENCE: 170
agccaacctt tcgatcgtag cttgcagctg accagggttt                              40

<210> SEQ ID NO 171
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_35

<400> SEQUENCE: 171
ctacgatcga aaggttggct tccgtacacc tcaagatgag                              40

<210> SEQ ID NO 172
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_36

<400> SEQUENCE: 172
attccagacc aatggtaggc ctcatcttga ggtgtacgga                              40

<210> SEQ ID NO 173
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_37

<400> SEQUENCE: 173
gcctaccatt ggtctggaat acttcaggcc tctgcaagag                              40

<210> SEQ ID NO 174
```

```
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_38

<400> SEQUENCE: 174
gcaacgtact gtgcaatgtt ctcttgcaga ggcctgaagt                     40

<210> SEQ ID NO 175
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_39

<400> SEQUENCE: 175
aacattgcac agtacgttgc tagcgctctg ggtgtgggtg                     40

<210> SEQ ID NO 176
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_40

<400> SEQUENCE: 176
tttaggagct gcgtcatctg cacccacacc cagagcgcta                     40

<210> SEQ ID NO 177
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_41

<400> SEQUENCE: 177
cagatgacgc agctcctaaa gcttgggaac gtctcctgaa                     40

<210> SEQ ID NO 178
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_42

<400> SEQUENCE: 178
tgaggacctc gttgaaagcg ttcaggagac gttcccaagc                     40

<210> SEQ ID NO 179
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_43

<400> SEQUENCE: 179
cgctttcaac gaggtcctca acagcttcgc caactacaac                     40

<210> SEQ ID NO 180
<211> LENGTH: 40
```

```
<212> TYPE: DNA
<213> ORGANISM: Artificial
<220> FEATURE:
<223> OTHER INFORMATION: derived from Biomphalaria glabrata;
      construction oligo BgHb_44

<400> SEQUENCE: 180
tccgtatcgc tcagtccgat gttgtagttg gcgaagctgt                             40

<210> SEQ ID NO 181
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_45

<400> SEQUENCE: 181
atcggactga gcgatacgga caaagtagcc cttcagagca                             40

<210> SEQ ID NO 182
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_46

<400> SEQUENCE: 182
agcggttaac ctagaccaac tgctctgaag ggctactttg                             40

<210> SEQ ID NO 183
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_47

<400> SEQUENCE: 183
gttggtctag gttaaccgct ggtgcagacg gtaagagaaa                             40

<210> SEQ ID NO 184
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_48

<400> SEQUENCE: 184
gcaccaacct gacaccagca tttctcttac cgtctgcacc                             40

<210> SEQ ID NO 185
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_49

<400> SEQUENCE: 185
tgctggtgtc aggttggtgc tgtggatgtt caacaacgtc                             40

<210> SEQ ID NO 186
<211> LENGTH: 40
<212> TYPE: DNA
```

```
<213> ORGANISM: Artificial
<220> FEATURE:
<223> OTHER INFORMATION: derived from Biomphalaria glabrata;
      construction oligo BgHb_50

<400> SEQUENCE: 186
aacctctcac gcatgttcgg gacgttgttg aacatccaca                          40

<210> SEQ ID NO 187
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_51

<400> SEQUENCE: 187
ccgaacatgc gtgagaggtt caccaagttc aacgcacgac                          40

<210> SEQ ID NO 188
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_52

<400> SEQUENCE: 188
cttgagtgct tcgtctgact gtcgtgcgtt gaacttggtg                          40

<210> SEQ ID NO 189
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_53

<400> SEQUENCE: 189
agtcagacga agcactcaag accgacgcag aattcctgaa                          40

<210> SEQ ID NO 190
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_54

<400> SEQUENCE: 190
cgatgattgc gtctacctgc ttcaggaatt ctgcgtcggt                          40

<210> SEQ ID NO 191
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_55

<400> SEQUENCE: 191
gcaggtagac gcaatcatcg gtggtttcga gaccctgatc                          40

<210> SEQ ID NO 192
<211> LENGTH: 40
<212> TYPE: DNA
<213> ORGANISM: Artificial
```

<220> FEATURE:
<223> OTHER INFORMATION: derived from Biomphalaria glabrata;
      construction oligo BgHb_56

<400> SEQUENCE: 192
tctgcgtcgt tgaggttgtt gatcagggtc tcgaaaccac                            40

<210> SEQ ID NO 193
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_57

<400> SEQUENCE: 193
aacaacctca acgacgcaga cctcttgctg aacagactag                            40

<210> SEQ ID NO 194
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_58

<400> SEQUENCE: 194
gtgttcgtca gccagactct ctagtctgtt cagcaagagg                            40

<210> SEQ ID NO 195
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_59

<400> SEQUENCE: 195
agagtctggc tgacgaacac ctcgaaaaga agccagcgat                            40

<210> SEQ ID NO 196
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_60

<400> SEQUENCE: 196
gaccgaagta gttgctggag atcgctggct tcttttcgag                            40

<210> SEQ ID NO 197
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_61

<400> SEQUENCE: 197
ctccagcaac tacttcggtc ctctccagaa gaacatccac                            40

<210> SEQ ID NO 198
<211> LENGTH: 40
<212> TYPE: DNA
<213> ORGANISM: Artificial
<220> FEATURE:

```
<223> OTHER INFORMATION: derived from Biomphalaria glabrata;
      construction oligo BgHb_62

<400> SEQUENCE: 198
agggtaccct cgatgaagag gtggatgttc ttctggagag                    40

<210> SEQ ID NO 199
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_63

<400> SEQUENCE: 199
ctcttcatcg agggtaccct caactttggg agtgactcag                    40

<210> SEQ ID NO 200
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_64

<400> SEQUENCE: 200
agtccaagct ctagcttcgt ctgagtcact cccaaagttg                    40

<210> SEQ ID NO 201
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_65

<400> SEQUENCE: 201
acgaagctag agcttggact cacttggtcg gagcgttgaa                    40

<210> SEQ ID NO 202
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_66

<400> SEQUENCE: 202
cgtggtcctt gatgaccttg ttcaacgctc cgaccaagtg                    40

<210> SEQ ID NO 203
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_67

<400> SEQUENCE: 203
caaggtcatc aaggaccacg ctatccacaa cctgggtttg                    40

<210> SEQ ID NO 204
<211> LENGTH: 40
<212> TYPE: DNA
<213> ORGANISM: Artificial
<220> FEATURE:
<223> OTHER INFORMATION: derived from Biomphalaria glabrata;
``` construction oligo BgHb_68

<400> SEQUENCE: 204
gcgtctctgt ctatgtcgga caaacccagg ttgtggatag                                40

<210> SEQ ID NO 205
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_69

<400> SEQUENCE: 205
tccgacatag acagagacgc tctggtctcg tcatggaatc                                40

<210> SEQ ID NO 206
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_70

<400> SEQUENCE: 206 tcctgccta ccggtcaatt gattccatga cgagaccaga                                 40

<210> SEQ ID NO 207
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_71

<400> SEQUENCE: 207
aattgaccgg tagggcagga ggtagtcgaa acgcaggtac                                40

<210> SEQ ID NO 208
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_72

<400> SEQUENCE: 208
gcatccacag cacgaggtta gtacctgcgt ttcgactacc                                40

<210> SEQ ID NO 209
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_73

<400> SEQUENCE: 209
taacctcgtg ctgtggatgc tcgaaaacgt gcctaacatg                                40

<210> SEQ ID NO 210
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_74

<400> SEQUENCE: 210
aacttcgaga actggtcacg catgttaggc acgttttcga                                40

<210> SEQ ID NO 211
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_75

<400> SEQUENCE: 211
cgtgaccagt tctcgaagtt caacgctagg cagtccgacg                                40

<210> SEQ ID NO 212
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_76

<400> SEQUENCE: 212
agcgtccttt ctcaggttat cgtcggactg cctagcgttg                                40

<210> SEQ ID NO 213
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_77

<400> SEQUENCE: 213
ataacctgag aaaggacgct gagttcgtgc gacaagttga                                40

<210> SEQ ID NO 214
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_78

<400> SEQUENCE: 214
ccagacctcc cgtaatcagg tcaacttgtc gcacgaactc                                40

<210> SEQ ID NO 215
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_79

<400> SEQUENCE: 215
cctgattacg ggaggtctgg aatcactcgt cgacaacgtg                                40

<210> SEQ ID NO 216
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_80

<400> SEQUENCE: 216
tgcaggaaga ttgggttgtt cacgttgtcg acgagtgatt          40

<210> SEQ ID NO 217
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_81

<400> SEQUENCE: 217
aacaacccaa tcttcctgca ggaagctctg gttagactcg          40

<210> SEQ ID NO 218
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_82

<400> SEQUENCE: 218
caggttaagg tgagcatctg cgagtctaac cagagcttcc          40

<210> SEQ ID NO 219
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_83

<400> SEQUENCE: 219
cagatgctca ccttaacctg aagcctaggg tgggtcttga          40

<210> SEQ ID NO 220
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_84

<400> SEQUENCE: 220
tctgcagtgg accaaagtac tcaagaccca ccctaggctt          40

<210> SEQ ID NO 221
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_85

<400> SEQUENCE: 221
gtactttggt ccactgcaga ggtacataca cgcctacatc          40

<210> SEQ ID NO 222
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_86

<400> SEQUENCE: 222
gatactccga gtgccttttc gatgtaggcg tgtatgtacc         40

<210> SEQ ID NO 223
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_87

<400> SEQUENCE: 223
gaaaaggcac tcggagtatc ggcagattcc gcagctccaa         40

<210> SEQ ID NO 224
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_88

<400> SEQUENCE: 224
aagcaagtcg gtccatgctc ttggagctgc ggaatctgcc         40

<210> SEQ ID NO 225
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_89

<400> SEQUENCE: 225
gagcatggac cgacttgctt accgctttca acaacgtcct         40

<210> SEQ ID NO 226
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_90

<400> SEQUENCE: 226
gatggtgatg cctgtccttc aggacgttgt tgaaagcggt         40

<210> SEQ ID NO 227
<211> LENGTH: 40
<212> TYPE: DNA
<213> ORGANISM: Artificial
<220> FEATURE:
<223> OTHER INFORMATION: derived from Biomphalaria glabrata;
      construction oligo BgHb_91

<400> SEQUENCE: 227
gaaggacagg catcaccatc accatcacta ggacccagct         40

<210> SEQ ID NO 228
<211> LENGTH: 41
<212> TYPE: DNA
<213> ORGANISM: Artificial
<220> FEATURE:
<223> OTHER INFORMATION: derived from Biomphalaria glabrata;
      construction oligo BgHb_92

<400> SEQUENCE: 228

```
ggggaccact tgtacaaga aagctgggtc ctagtgatgg t                   41
```

<210> SEQ ID NO 229
<211> LENGTH: 2080
<212> TYPE: DNA
<213> ORGANISM: Escherichia coli

<400> SEQUENCE: 229

```
cgactgcacg gtgaccaatg cttctggcgt caggcagcca tcggaagctg tggtatggct    60
gtgcaggtcg taaatcactg cataattcgt gtcgctcaag gcgcactccc gttctggata   120
atgtttttg cgccgacatc ataacggttc tggcaaatat tctgaaatga gctgttgaca   180
attaatcatc ggctcgtata atgtgtggaa ttgtgagcgg ataacaattt cacacaggaa   240
acagaattca atgctccgcc cagtcgaaac cccaacccga gagattaaaa aactggatgg   300
cctgtgggca tttagcctgg atcgcgaaaa ctgcggcatt gatcaacgtt ggtgggaatc   360
tgcgctacag gaaagtcgag cgattgcagt accggggagc tttaacgatc agtttgcgga   420
tgccgatatt cgcaactatg cggggaacgt ttggtatcag cgggaagtgt ttataccgaa   480
aggctgggct ggacagcgca tagtcttacg ctttgatgcc gtgacccact atggcaaagt   540
gtgggtgaac aaccaggaag tgatggaaca tcagggaggc tacactccct ttgaagcaga   600
tgtgacccg tatgtgattg cgggcaaatc agtgaggatt accgtgtgcg tcaacaacga   660
actgaactgg cagacaatac cgcccggtat ggttatcacg gacgagaacg gcaaaaagaa   720
acagtcgtac tttcacgact tttttaacta tgccggcatt caccgctcgg ttatgctgta   780
tacgaccccg aatacctggg tcgatgatat caccgtagtg acacacgtgg cgcaagattg   840
caatcatgcg agtgtggatt ggcaagtcgt ggcgaatggc gatgtaagcg tagaactaag   900
ggatgcggat cagcaagtgg tagcaaccgg ccagggtacc agcggtacct tgcaagtggt   960
gaatcctcat ctgtggcaac tggagaagg ctatctgtat gagctgtgcg ttacggccaa  1020
atctcagacg gaatgcgaca tctatcctct tcgcgtgggc attagatcag tagccgtgaa  1080
aggcgaacag ttcctgatta accacaagcc gttctacttt accggttttg gtcgccatga  1140
agacgctgat ctgcgcggca aaggcttga caacgtcctg atggtgcatg atcatgcgct  1200
catggattgg atagggcca acagctatcg tacttcccac tacccgtatg ccgaagagat  1260
gttagattgg gcggacgaac atggcatagt cgtgatcgat gaaacagctg ccgtgggtt  1320
taacctttca ctaggcattg ggttcgaagc cggcaacaaa ccgaaagaac tgtacagtga  1380
ggaagcagtc aacggagaaa ctcaacaggc acatctgcag gcgataaagg aactgattgc  1440
gcgcgataag aaccatccgt ccgtcgtgat gtggagcata gcgaatgaac cagatacgcg  1500
tcctcaagga gctagggaat attttgctcc gctcgcggaa gctaccagaa aactagatcc  1560
cactcgcccg attacttgcg tcaacgtgat gttttgcgat gcgcataccg acaccattag  1620
cgacctgttt gatgtgctgt gcctgaaccg ctattacggt tggtatgtac agtcagggga  1680
tctggaaact gcggagaaag tactgagaa agagctgcta gcttggcagg agaaactcca  1740
tcagccgatt attatcacgg aatatggggt agacacccta gcaggtctcc atagcatgta  1800
cacggacatg tggtctgagg aataccagtg tgcctggctg gatatgtatc atcgcgtgtt  1860
tgatagggtc tcagccgtgg tgggtgagca ggtttggaac tttgcggact tgcaacgtc   1920
tcaagggatt ttgcgtgtgg cgggaacaa gaaaggcatt ttcaccagag atcgcaagcc  1980
gaaaagcgcc gcttttctat tgcagaagcg ctggacgggg atgaatttg gcgaaaaacc  2040
ccagcagggc ggtaaacaac atcaccatca ccatcactaa                       2080
```

<210> SEQ ID NO 230
<211> LENGTH: 1861
<212> TYPE: DNA
<213> ORGANISM: Biomphalaria glabrata

<400> SEQUENCE: 230

```
ggggacaagt tgtacaaaa aagcaggctt cgaaggagat agaaccatga tgttcgtcct      60
taagggatcc gtcgtccaag cattcgtcct gttgagcatc gtctgcctcg aaatcaccat     120
agcagacgac ggtgtcaggt atgtgaacgc tgagtggaag cgtccagaac aatcccaaga    180
aggtaggcac tctagaacgg ctaggaggtt agaggacaaa tctgaggaag tcgcatgctc    240
tacggaagtg aagttccgac agagagctcc tgccgagtac gctaacaaga tcaagaaggc    300
aaaggacaag ctgcggagac tggaatctca gttcgacgat tgccagcagg aaaacgacag    360
gaaggacagg ctgatccaac tccaagcaaa cctcaccgat accatccaca ggctcgtaac    420
cgactctgac attcaggcac ttaggtcatc ctgggctact ttgaccgctg gtgctgatgg    480
acggaacaac ttcggtaaca acttcgtgct gtggctactg aacacgatcc cgaacataag    540
ggagcgtttc gagaagttca cgctcacca gagcgatgaa gccctcaaga acgacaacga    600
attcgtgaag caggtgaagc tgatcgttgg tggactgcag agcttcatcg acaacctcga    660
aaaccctggt cagctgcaag ctacgatcga aaggttggct tccgtacacc tcaagatgag    720
gcctaccatt ggtctggaat acttcaggcc tctgcaagag aacattgcac agtacgttgc    780
tagcgctctg ggtgtgggtg cagatgacgc agctcctaaa gcttgggaac gtctcctgaa    840
cgcttttcaac gaggtcctca acagcttcgc caactacaac atcggactga gcgatacgga    900
caaagtagcc cttcagagca gttggtctag gttaaccgct ggtgcagacg gtaagagaaa    960
tgctggtgtc aggttggtgc tgtggatgtt caacaacgtc ccgaacatgc gtgagaggtt   1020
caccaagttc aacgcacgac agtcagacga agcactcaag accgacgcag aattcctgaa   1080
gcaggtagac gcaatcatcg gtggtttcga gaccctgatc aacaacctca acgacgcaga   1140
cctcttgctg aacagactag agagtctggc tgacgaacac ctcgaaaaga agccagcgat   1200
ctccagcaac tacttcggtc ctctccagaa gaacatccac ctcttcatcg agggtaccct   1260
caactttggg agtgactcag acgaagctag agcttggact cacttggtcg agcgttgaa    1320
caaggtcatc aaggaccacg ctatccacaa cctgggtttg tccgacatag acagagacgc   1380
tctggtctcg tcatggaatc aattgaccgg tagggcagga ggtagtcgaa acgcaggtac   1440
taacctcgtc ctgtggatgc tcgaaaacgt gcctaacatg cgtgaccagt tctcgaagtt   1500
caacgctagg cagtccgacg ataacctgag aaaggacgct gagttcgtgc gacaagttga   1560
cctgattacg ggaggtctgg aatcactcgt cgacaacgtg aacaacccaa tcttcctgca   1620
ggaagctctg gttagactcg cagatgctca ccttaacctg aagcctaggg tgggtcttga   1680
gtactttggt ccactgcaga ggtacataca cgcctacatc gaaaaggcac tcggagtatc   1740
ggcagattcc gcagctccaa gagcatggac cgacttgctt accgctttca caacgtcct    1800
gaaggacagg catcaccatc accatcacta ggacccagct ttcttgtaca agtggtccc    1860
c                                                                    1861
```

<210> SEQ ID NO 231
<211> LENGTH: 394
<212> TYPE: DNA
<213> ORGANISM: Artificial
<220> FEATURE:

<223> OTHER INFORMATION: derived from Biomphalaria glabrata; BgHb_A

<400> SEQUENCE: 231

| | | | | | |
|---|---|---|---|---|---|
| gcctccctcg | cgccatcagg | ctcttctggg | gacaagtttg | tacaaaaaag | caggcttcga | 60 |
| aggagataga | accatgatgt | tcgtccttaa | gggatccgtc | gtccaagcat | tcgtcctgtt | 120 |
| gagcatcgtc | tgcctcgaaa | tcaccatagc | agacgacggt | gtcaggtatg | tgaacgctga | 180 |
| gtggaagcgt | ccagaacaat | cccaagaagg | taggcactct | agaacggcta | ggaggttaga | 240 |
| ggacaactct | gaggaagtcg | catgctctac | ggaagtgaag | ttccgacaga | gagctcctgc | 300 |
| cgagtacgct | aacaagatca | agaaggcaaa | ggacaagctg | cggagactgg | aatctcagtt | 360 |
| cgacgatcga | agagcctgag | cgggctggca | aggc | | | 394 |

<210> SEQ ID NO 232
<211> LENGTH: 394
<212> TYPE: DNA
<213> ORGANISM: Artificial
<220> FEATURE:
<223> OTHER INFORMATION: derived from Biomphalaria glabrata; BgHb_B

<400> SEQUENCE: 232

| | | | | | |
|---|---|---|---|---|---|
| gcctccctcg | cgccatcagg | ctcttcttac | ggaagtgaag | ttccgacaga | gagctcctgc | 60 |
| cgagtacgct | aacaagatca | agaaggcaaa | ggacaagctg | cggagactgg | aatctcagtt | 120 |
| cgacgattgc | cagcaggaaa | acgacaggaa | ggacaggctg | atccaactcc | aagcaaacct | 180 |
| caccgatacc | atccacaggc | tcgtaaccga | ctctgacatt | caggcactta | ggtcatcctg | 240 |
| ggctactttg | accgctggtg | ctgatggacg | gaacaacttc | ggtaacaact | tcgtgctgtg | 300 |
| gctactgaac | acgatcccga | acataaggga | gcgtttcgag | aagttcaacg | ctcaccagag | 360 |
| cgatgaacga | agagcctgag | cgggctggca | aggc | | | 394 |

<210> SEQ ID NO 233
<211> LENGTH: 394
<212> TYPE: DNA
<213> ORGANISM: Artificial
<220> FEATURE:
<223> OTHER INFORMATION: derived from Biomphalaria glabrata; BgHb_C

<400> SEQUENCE: 233

| | | | | | |
|---|---|---|---|---|---|
| gcctccctcg | cgccatcagg | ctcttctacg | gaacaacttc | ggtaacaact | tcgtgctgtg | 60 |
| gctactgaac | acgatcccga | acataaggga | gcgtttcgag | aagttcaacg | ctcaccagag | 120 |
| cgatgaagcc | ctcaagaacg | acaacgaatt | cgtgaagcag | gtgaagctga | tcgttggtgg | 180 |
| actgcagagc | ttcatcgaca | acctcgaaaa | ccctggtcag | ctgcaagcta | cgatcgaaag | 240 |
| gttggcttcc | gtacacctca | agatgaggcc | taccattggt | ctggaatact | tcaggcctct | 300 |
| gcaagagaac | attgcacagt | acgttgctag | cgctctgggt | gtgggtgcag | atgacgcagc | 360 |
| tcctaaacga | agagcctgag | cgggctggca | aggc | | | 394 |

<210> SEQ ID NO 234
<211> LENGTH: 394
<212> TYPE: DNA
<213> ORGANISM: Artificial
<220> FEATURE:
<223> OTHER INFORMATION: derived from Biomphalaria glabrata; BgHb_D

<400> SEQUENCE: 234

| | | | | | |
|---|---|---|---|---|---|
| gcctccctcg | cgccatcagg | ctcttctgcc | taccattggt | ctggaatact | tcaggcctct | 60 |
| gcaagagaac | attgcacagt | acgttgctag | cgctctgggt | gtgggtgcag | atgacgcagc | 120 |

```
tcctaaagct tgggaacgtc tcctgaacgc tttcaacgag gtcctcaaca gcttcgccaa    180
ctacaacatc ggactgagcg atacggacaa agtagcccct cagagcagtt ggtctaggtt    240
aaccgctggt gcagacggta agagaaatgc tggtgtcagg ttggtgctgt ggatgttcaa    300
caacgtcccg aacatgcgtg agaggttcac caagttcaac gcacgacagt cagacgaagc    360
actcaagcga agagcctgag cgggctggca aggc                                394

<210> SEQ ID NO 235
<211> LENGTH: 394
<212> TYPE: DNA
<213> ORGANISM: Artificial
<220> FEATURE:
<223> OTHER INFORMATION: derived from Biomphalaria glabrata; BgHb_E

<400> SEQUENCE: 235
gcctccctcg cgccatcagg ctcttcttgc tggtgtcagg ttggtgctgt ggatgttcaa     60
caacgtcccg aacatgcgtg agaggttcac caagttcaac gcacgacagt cagacgaagc    120
actcaagacc gacgcagaat tcctgaagca ggtagacgca atcatcggtg gtttcgagac    180
cctgatcaac aacctcaacg acgcagacct cttgctgaac agactagaga gtctggctga    240
cgaacacctc gaaaagaagc cagcgatctc cagcaactac ttcggtcctc tccagaagaa    300
catccacctc ttcatcgagg gtaccctcaa ctttgggagt gactcagacg aagctagagc    360
ttggactcga agagcctgag cgggctggca aggc                                394

<210> SEQ ID NO 236
<211> LENGTH: 394
<212> TYPE: DNA
<213> ORGANISM: Artificial
<220> FEATURE:
<223> OTHER INFORMATION: derived from Biomphalaria glabrata; BgHb_F

<400> SEQUENCE: 236
gcctccctcg cgccatcagg ctcttctctc cagcaactac ttcggtcctc tccagaagaa     60
catccacctc ttcatcgagg gtaccctcaa ctttgggagt gactcagacg aagctagagc    120
ttggactcac ttggtcggag cgttgaacaa ggtcatcaag gaccacgcta tccacaacct    180
gggtttgtcc gacatagaca gagacgctct ggtctcgtca tggaatcaat tgaccggtag    240
ggcaggaggt agtcgaaacg caggtactaa cctcgtgctg tggatgctcg aaaacgtgcc    300
taacatgcgt gaccagttct cgaagttcaa cgctaggcag tccgacgata acctgagaaa    360
ggacgctcga agagcctgag cgggctggca aggc                                394

<210> SEQ ID NO 237
<211> LENGTH: 394
<212> TYPE: DNA
<213> ORGANISM: Artificial
<220> FEATURE:
<223> OTHER INFORMATION: derived from Biomphalaria glabrata; BgHb_G

<400> SEQUENCE: 237
gcctccctcg cgccatcagg ctcttcttaa cctcgtgctg tggatgctcg aaaacgtgcc     60
taacatgcgt gaccagttct cgaagttcaa cgctaggcag tccgacgata acctgagaaa    120
ggacgctgag ttcgtgcgac aagttgacct gattacggga ggtctggaat cactcgtcga    180
caacgtgaac aacccaatct tcctgcagga agctctggtt agactcgcag atgctcacct    240
taacctgaag cctagggtgg gtcttgagta ctttggtcca ctgcagaggt acatacacgc    300
```

```
ctacatcgaa aaggcactcg gagtatcggc agattccgca gctccaagag catggaccga    360
cttgcttcga agagcctgag cgggctggca aggc                                394
```

<210> SEQ ID NO 238
<211> LENGTH: 235
<212> TYPE: DNA
<213> ORGANISM: Artificial
<220> FEATURE:
<223> OTHER INFORMATION: derived from Biomphalaria glabrata; BgHb_H

<400> SEQUENCE: 238

```
gcctccctcg cgccatcagg ctcttctgta ctttggtcca ctgcagaggt acatacacgc     60
ctacatcgaa aaggcactcg gagtatcggc agattccgca gctccaagag catggaccga    120
cttgcttacc gctttcaaca acgtcctgaa ggacaggcat caccatcacc atcactagga    180
cccagctttc ttgtacaaag tggtccccg aagagcctga gcgggctggc aaggc          235
```

<210> SEQ ID NO 239
<211> LENGTH: 394
<212> TYPE: DNA
<213> ORGANISM: Artificial
<220> FEATURE:
<223> OTHER INFORMATION: derived from beta-D-glucuronidase; UidA_A

<400> SEQUENCE: 239

```
gcctccctcg cgccatcagg ctcttctcga ctgcacggtg accaatgctt ctggcgtcag     60
gcagccatcg gaagctgtgg tatggctgtg caggtcgtaa atcactgcat aattcgtgtc    120
gctcaaggcg cactcccgtt ctggataatg ttttttgcgc cgacatcata acggttctgg    180
caaatattct gaaatgagct gttgacaatt aatcatcggc tcgtataatg tgtggaattg    240
tgagcggata acaatttcac acaggaaaca gaattcaatg ctccgcccag tcgaaacccc    300
aacccgagag attaaaaaac tggatggcct gtgggcattt agcctggatc gcgaaaactg    360
cggcattcga agagcctgag cgggctggca aggc                                394
```

<210> SEQ ID NO 240
<211> LENGTH: 394
<212> TYPE: DNA
<213> ORGANISM: Artificial
<220> FEATURE:
<223> OTHER INFORMATION: derived from beta-D-glucuronidase; UidA_B

<400> SEQUENCE: 240

```
gcctccctcg cgccatcagg ctcttctaca gaattcaatg ctccgcccag tcgaaacccc     60
aacccgagag attaaaaaac tggatggcct gtgggcattt agcctggatc gcgaaaactg    120
cggcattgat caacgttggt gggaatctgc gctacaggaa agtcgagcga ttgcagtacc    180
ggggagcttt aacgatcagt ttgcggatgc cgatattcgc aactatgcgg ggaacgtttg    240
gtatcagcgg gaagtgttta taccgaaagg ctgggctgga cagcgcatag tcttacgctt    300
tgatgccgtg acccactatg gcaaagtgtg ggtgaacaac caggaagtga tggaacatca    360
gggaggccga agagcctgag cgggctggca aggc                                394
```

<210> SEQ ID NO 241
<211> LENGTH: 394
<212> TYPE: DNA
<213> ORGANISM: Artificial
<220> FEATURE:
<223> OTHER INFORMATION: derived from beta-D-glucuronidase; UidA_C

<400> SEQUENCE: 241

```
gcctccctcg cgccatcagg ctcttctagg ctgggctgga cagcgcatag tcttacgctt      60
tgatgccgtg acccactatg gcaaagtgtg ggtgaacaac caggaagtga tggaacatca     120
gggaggctac actcccttttg aagcagatgt gaccccgtat gtgattgcgg gcaaatcagt    180
gaggattacc gtgtgcgtca acaacgaact gaactggcag acaataccgc ccggtatggt    240
tatcacggac gagaacggca aaagaaaca gtcgtacttt cacgactttt ttaactatgc     300
cggcattcac cgctcggtta tgctgtatac gaccccgaat acctgggtcg atgatatcac    360
cgtagtgcga agagcctgag cgggctggca aggc                                394
```

```
<210> SEQ ID NO 242
<211> LENGTH: 394
<212> TYPE: DNA
<213> ORGANISM: Artificial
<220> FEATURE:
<223> OTHER INFORMATION: derived from beta-D-glucuronidase; UidA_D

<400> SEQUENCE: 242
gcctccctcg cgccatcagg ctcttctaca gtcgtacttt cacgactttt ttaactatgc     60
cggcattcac cgctcggtta tgctgtatac gaccccgaat acctgggtcg atgatatcac    120
cgtagtgaca cacgtggcgc aagattgcaa tcatgcgagt gtggattggc aagtcgtggc    180
gaatggcgat gtaagcgtag aactaaggga tgcggatcag caagtggtag caaccggcca    240
gggtaccagc ggtaccttgc aagtggtgaa tcctcatctg tggcaacctg gagaaggcta    300
tctgtatgag ctgtgcgtta cggccaaatc tcagacggaa tgcgacatct atcctcttcg    360
cgtgggccga agagcctgag cgggctggca aggc                                394
```

```
<210> SEQ ID NO 243
<211> LENGTH: 394
<212> TYPE: DNA
<213> ORGANISM: Artificial
<220> FEATURE:
<223> OTHER INFORMATION: derived from beta-D-glucuronidase; UidA_E

<400> SEQUENCE: 243
gcctccctcg cgccatcagg ctcttctgaa tcctcatctg tggcaacctg gagaaggcta     60
tctgtatgag ctgtgcgtta cggccaaatc tcagacggaa tgcgacatct atcctcttcg    120
cgtgggcatt agatcagtag ccgtgaaagg cgaacagttc ctgattaacc acaagccgtt    180
ctactttacc ggttttggtc gccatgaaga cgctgatctg cgcggcaaag ctttgacaa     240 cgtcctgatg gtgcatgatc atgcgctcat ggattggata ggggccaaca gctatcgtac    300
ttcccactac ccgtatgccg aagagatgtt agattgggcg gacgaacatg gcatagtcgt    360
gatcgatcga agagcctgag cgggctggca aggc                                394
```

```
<210> SEQ ID NO 244
<211> LENGTH: 394
<212> TYPE: DNA
<213> ORGANISM: Artificial
<220> FEATURE:
<223> OTHER INFORMATION: derived from beta-D-glucuronidase; UidA_F

<400> SEQUENCE: 244
gcctccctcg cgccatcagg ctcttctcat ggattggata ggggccaaca gctatcgtac     60
ttcccactac ccgtatgccg aagagatgtt agattgggcg gacgaacatg gcatagtcgt    120
gatcgatgaa acagctgccg tggggtttaa cctttcacta ggcattgggt tcgaagccgg    180
```

```
caacaaaccg aaagaactgt acagtgagga agcagtcaac ggagaaactc aacaggcaca      240
tctgcaggcg ataaaggaac tgattgcgcg cgataagaac catccgtccg tcgtgatgtg      300
gagcatagcg aatgaaccag atacgcgtcc tcaaggagct agggaatatt ttgctccgct      360
cgcggaacga agagcctgag cgggctggca aggc                                  394

<210> SEQ ID NO 245
<211> LENGTH: 394
<212> TYPE: DNA
<213> ORGANISM: Artificial
<220> FEATURE:
<223> OTHER INFORMATION: derived from beta-D-glucuronidase; UidA_G

<400> SEQUENCE: 245
gcctccctcg cgccatcagg ctcttctgcg cgataagaac catccgtccg tcgtgatgtg       60
gagcatagcg aatgaaccag atacgcgtcc tcaaggagct agggaatatt ttgctccgct      120
cgcggaagct accagaaaac tagatcccac tcgcccgatt acttgcgtca acgtgatgtt      180
ttgcgatgcg cataccgaca ccattagcga cctgtttgat gtgctgtgcc tgaaccgcta      240
ttacggttgg tatgtacagt caggggatct ggaaactgcg gagaaagtac tggagaaaga      300
gctgctagct tggcaggaga aactccatca gccgattatt atcacggaat atggggtaga      360
caccctacga agagcctgag cgggctggca aggc                                  394

<210> SEQ ID NO 246
<211> LENGTH: 274
<212> TYPE: DNA
<213> ORGANISM: Artificial
<220> FEATURE:
<223> OTHER INFORMATION: derived from beta-D-glucuronidase; UidA_H

<400> SEQUENCE: 246
gcctccctcg cgccatcagg ctcttcttct ggaaactgcg gagaaagtac tggagaaaga       60
gctgctagct tggcaggaga aactccatca gccgattatt atcacggaat atggggtaga      120
caccctagca ggtctccata gcatgtacac ggacatgtgg tctgaggaat accagtgtgc      180
ctggctggat atgtatcatc gcgtgtttga tagggtctca gccgtggtgg gtgagcaggt      240
ttggaaccga agagcctgag cgggctggca aggc                                  274

<210> SEQ ID NO 247
<211> LENGTH: 334
<212> TYPE: DNA
<213> ORGANISM: Artificial
<220> FEATURE:
<223> OTHER INFORMATION: derived from beta-D-glucuronidase; UidA_I

<400> SEQUENCE: 247
gcctccctcg cgccatcagg ctcttctcac ggacatgtgg tctgaggaat accagtgtgc       60
ctggctggat atgtatcatc gcgtgtttga tagggtctca gccgtggtgg gtgagcaggt      120
ttggaacttt gcggactttg caacgtctca agggattttg cgtgtgggcg ggaacaagaa      180
aggcattttc accagagatc gcaagccgaa aagcgccgct tttctattgc agaagcgctg      240
gacggggatg aattttggcg aaaaacccca gcagggcggt aaacaacatc accatcacca      300
tcactaacga agagcctgag cgggctggca aggc                                  334

<210> SEQ ID NO 248
<211> LENGTH: 196
<212> TYPE: DNA
<213> ORGANISM: Artificial
```

```
<220> FEATURE:
<223> OTHER INFORMATION: derived from beta-D-glucuronidase or
      Biomphalaria glabrata; >FL3SQ3101APQNV

<400> SEQUENCE: 248
gctcttctgt actttggtcc actgcagagg tacatacacg cctacatcga aaaggcactc      60
ggagtatcgg cagattccgc agctccaaga gcatggaccg acttgcttac cgctttcaac     120
aacgtcctga aggacaggca tctaccatca ccatcactag gacccagctt tcttgtacaa     180
agtggtcccc cgaaga                                                     196

<210> SEQ ID NO 249
<211> LENGTH: 193
<212> TYPE: DNA
<213> ORGANISM: Artificial
<220> FEATURE:
<223> OTHER INFORMATION: derived from beta-D-glucuronidase or
      Biomphalaria glabrata; >FL3SQ3101APG7U

<400> SEQUENCE: 249
gctcttctgt actttggtcc actgcagagg tacatacacg ctacatcgaa aggcactcgg      60
agtatcggca gattccgcag ctccaagagc atggaccgac ttgcttaccg ctttcaacaa     120
cgtcctgaag gacaggcatc accatcacca tcactaggac ccagctttct tgtacaaagt    180
ggtcccccga aga                                                        193
```